United States Patent [19]

Hudspeth et al.

[11] Patent Number: 4,743,585

[45] Date of Patent: May 10, 1988

[54] RENIN INHIBITORS

[75] Inventors: James P. Hudspeth; James S. Kaltenbronn; Elizabeth A. Lunney; Joseph T. Repine; W. Howard Roark; Michael A. Stier; Francis J. Tinney; Peter W. K. Woo, all of Ann Arbor, Mich.; Ernest D. Nicolaides, Ramona, Calif.

[73] Assignee: Warner-Lambert Company, Morris Plains, N.J.

[21] Appl. No.: 920,330

[22] Filed: Nov. 21, 1986

[51] Int. Cl.$^4$ .................. A61K 37/02; C07K 5/08; C07K 5/10; C07K 7/06

[52] U.S. Cl. .................. 514/17; 514/18; 530/332; 530/323; 530/330; 530/331; 530/329

[58] Field of Search ............... 530/324, 330, 317, 328, 530/329; 514/18

[56] References Cited

U.S. PATENT DOCUMENTS

| | | | |
|---|---|---|---|
| 4,384,994 | 5/1983 | Veber et al. | 530/330 |
| 4,424,207 | 1/1984 | Szelke et al. | 530/327 |
| 4,470,971 | 9/1984 | Boger et al. | 530/328 |
| 4,477,440 | 10/1984 | Boger et al. | 530/328 |
| 4,477,441 | 10/1984 | Boger et al. | 530/328 |
| 4,478,826 | 10/1984 | Veber et al. | 530/328 |
| 4,479,941 | 10/1984 | Veber et al. | 530/328 |
| 4,485,099 | 11/1984 | Boger et al. | 530/317 |
| 4,548,926 | 10/1985 | Matsueda et al. | 514/18 |
| 4,595,677 | 6/1986 | Riniker et al. | 530/330 |
| 4,609,641 | 9/1986 | Evans et al. | 514/18 |
| 4,609,643 | 9/1986 | Szelke et al. | 530/329 |
| 4,618,600 | 10/1986 | Johnson et al. | 530/324 |
| 4,629,724 | 12/1986 | Ryono et al. | 530/330 |
| 4,636,491 | 1/1987 | Bock et al. | 514/18 |
| 4,650,661 | 3/1987 | Szelke et al. | 530/323 |
| 4,652,551 | 3/1987 | Luly et al. | 530/331 |
| 4,661,473 | 4/1987 | Boger et al. | 530/332 |
| 4,663,310 | 5/1987 | Bock et al. | 530/330 |
| 4,665,052 | 5/1987 | Boger | 530/317 |
| 4,665,055 | 5/1987 | Evans | 514/18 |
| 4,665,193 | 5/1987 | Ryono et al. | 546/256 |
| 4,668,663 | 5/1987 | Boger | 530/328 |
| 4,668,769 | 5/1987 | Hoover | 530/330 |
| 4,668,770 | 5/1987 | Boger et al. | 530/329 |

FOREIGN PATENT DOCUMENTS

WO84/00032  2/1984  PCT Int'l Appl. .

OTHER PUBLICATIONS

Charles M. Deber, Victor J. Hruby & Kenneth D. Kopple, Peptides–Structure & Function, Jun. 2–28, 1985, p. 745.

*Primary Examiner*—Delbert R. Phillips
*Attorney, Agent, or Firm*—Elizabeth M. Anderson

[57] ABSTRACT

The invention concerns novel renin-inhibitory peptides which are useful for treating renin associated hypertension and for treating hyperaldosteronism. Novel intermediates, processes for preparing both the intermediates and the novel peptides, pharmaceutical compositions, and methods of treatment are included.

8 Claims, No Drawings

RENIN INHIBITORS

BACKGROUND OF THE INVENTION

Renin is a natural enzyme which is released into the blood from the kidney. It cleaves its natural substrate, angiotensinogen, releasing a decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

The present invention concerns novel peptides which inhibit renin. The present invention is also concerned with pharmaceutical compositions containing the novel peptides, methods of treating renin-associated hypertension and of treating hyperaldosteronism, and methods for preparing the novel peptides.

U.S. Pat. No. 4,479,941 covers certain renin-inhibitory peptides of the formula $$A-B-B-D-N(H)-C(=O)-CH(NH-...)-... \quad (I)$$

wherein:
A is hydrogen;

$$R^3-O-CH_2-C(=O)-;\ R^3-CH_2-O-C(=O)-;$$
$$R^3-O-C(=O)-;\ R^3-(CH_2)_n-C(=O)-;$$

where n is 0 to 5 and $R^3$ has the same meaning as set out further below, and may additionally be hydrogen;

B is absent; glycyl; sarcosyl; or

[structure with $R^1$, $CH_2$, N-H, C=O]

D is absent; or

[structure with Z, N, C=O]

where Z is $(CH_2)_n$ and n is 1 or 2; or —S—;

$R^1$ is hydrogen; $C_{1-4}$ alkyl, hydroxy $C_{1-4}$ alkyl; phenyl, phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

$R^2$ is hydrogen $C_{1-4}$; alkyl; phenyl; phenyl mono-substituted with a member selected from the group consisting of methyl, trifluoromethyl, hydroxy, methoxy, fluoro, chloro, bromo, and iodo; or indolyl;

$R^3$ is $C_{3-6}$ alkyl; $C_{3-7}$ cycloalkyl; phenyl; or $C_{3-7}$ cycloalkyl or phenyl mono-substituted with a member selected from the group consisting of methyl, trifluoromethyl, hydroxy, methoxy, fluoro, chloro, bromo, and iodo;

$R^4$ is hydrogen; or $$\begin{array}{c} CH-R^5 \\ | \\ R^2 \end{array}$$

where $R^5$ is hydrogen; $C_{1-14}$ alkyl; hydroxy; or $C_{3-7}$ cycloalkyl; and E is $$-Y-(CH_2)_n-R_6 \quad (1)$$

where
Y is —NH— or —O—;
n is 0 to 5; and
$R^6$ is hydrogen; hydroxy; $C_{1-4}$ alkyl; $C_{3-7}$ cycloalkyl; aryl; aryl substituted with up to five members independently selected from the group consisting of $C_{1-6}$ alkyl, trifluoromethyl, hydroxy, $C_{1-4}$ alkoxy, amino, mono- or di-$C_{1-4}$ alkylamino, and halo; amino; mono-, di-, or tri-$C_{1-4}$ alkylamino; guanidyl; heterocyclic; or heterocyclic substituted with up to five members independently selected from the group consisting of $C_{1-6}$ alkyl, hydroxy, trifluoromethyl; $C_{1-4}$ alkoxy, halo, aryl, aryl $C_{1-4}$ alkylamino;

$$-Y-(CH_2)_n-CH\begin{pmatrix} (CH_2)_m-R^6 \\ \left(\begin{array}{c} CH-(CH_2)_l-R_a^6 \\ | \\ OH \end{array}\right)_k \end{pmatrix} \quad (2)$$

where
Y is as defined above;
n is 0 or 1;
k is 0 or 1;
l is 1 to 4;
m is 1 to 4; and $R^6$ and $R_\alpha^6$ may be the same or different and have the same meaning as $R^6$ above and $R_\alpha^6$ may additionally be

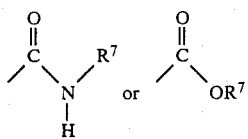

where $R^7$ is hydrogen or $C_{1-3}$ alkyl; or

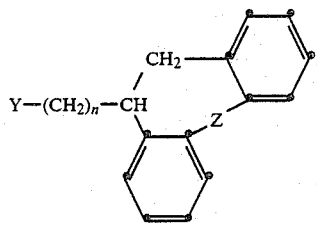

(3)

where
Y is as defined above;
n is 0 or 1; and
Z is (a) 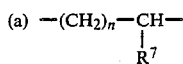

where
n is 0 or 1; and
$R^7$ is as defined above; or (b) 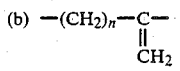

where n is 0 or 1;
wherein all of the asymmetric carbon atoms have an S configuration, except for those in the B, D, and E substituents, which may have an S or R configuration; and a pharmaceutically acceptable salt thereof.

PCT application No. 84/00032 relates to certain renin inhibiting peptides of the formula

X-D-E-A-B-Z-W wherein
X = H or N-protecting gp.;
D = absent or aromatic or lipophilic aminoacyl both opt. reduced at CO;
E = absent or aromatic aminoacyl or basic aminoacyl, both opt. N($\alpha$)-alkylated and/or reduced at CO;
A = a gp. of formula (III) or (IV):

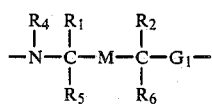 (III)

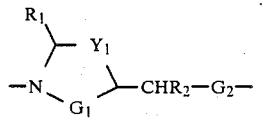 (IV)

$R_4$-$R_6$ = H, alkyl, $(CH_2)_nOH$ or $(CH_2)_nNH_2$;
n = 2, 3 or 4;
$G_1$ and $G_2$ = $(CH_2)$—$(CH_2)_m$, $(CH_2)_mCO$ or $CO(CH_2)_m$;
m = 0–3;
$R_1$ and $R_2$ = alkyl, arylmethyl, lipophilic gp. or H;
M = (i) $CH(OH)(CH_2)_{m'}$, (ii) $CH(NH_2)(CH_2)_{m'}$, (iii) $CH_2(CH_2)_{m'}$, (iv) $CO(CH_2)_{m'}$, (v) $(CH_2)_{m'}NX$ or (vi) $CH(NH_2)(CH_2)_{m'}CONH$;
m' = 0–2;
provided that (i) when M is (i), (iii) or (iv) and m' = 1, then 2–4 of D, E, B and Z are present; and when M is (v) and m' = 1, then 3 or 4 of D, E, B and Z are present; and
(2) when M is (i), (ii) or (iv), then $R_5$ and $R_6$ are H, and when M is (iii) or (v), then if one of $R_4$-$R_7$ is $(CH_2)_nOH$ or $(CH_2)_nNH_2$, the others are H or alkyl;
$Y_1$ = CO, $CH_2$, CH(OH), $CH(NH_2)$ or $CH_2NR_3$;
B = absent or lipophilic or aromatic aminoacyl both opt. N($\alpha$)-alkylated and/or reduced at CO;
Z = absent or aromatic aminoacyl or lipophilic aminoacyl both opt. N($\alpha$)-alkylated and/or reduced at CO;
W = OH or other terminal gp., $OR_3$, $NH_2$, $NHR_3$, $N(R_3)_2$ or a N-heterocyclic 5- or 6-membered ring contg. 1–3N, O or S and opt. unsatd. and opt. substd. by $R_3$ or $R_3CH_2$;
or Z—W = gp. of formula (V):

 (V)

L = NH, O or $NR_3$;
Q = H, 1-4C alkyl, aryl, imidazol-4-yl or indol-3-yl.

SUMMARY OF THE INVENTION

The present invention relates to novel peptides of the formula

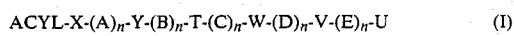 (I)

and the pharmaceutically acceptable acid addition salts thereof wherein acyl, X, A, n, Y, B, T, C, W, D, V, E, and U are defined herein below. The peptides are modified as isosteres in that one or more groups linking two amino acids in the peptide chain X-Y-T-W-V-U may be replaced by a group or groups selected from A, B, C, D, or E.

The present invention further relates to novel peptides of the formula

 (II)

and the pharmaceutically acceptable acid addition salts thereof wherein acyl, X, A, n, B, STA, ALA, STA, E, and U are as defined hereinbelow. The peptides are modified as isosteres in that one or more groups linking two amino acids in the peptide chain X-Y-STA-ALA-STA-U may be replaced by a group or groups selected from A, B, or E.

The present invention also includes a pharmaceutical composition comprising an effective amount of an above modified peptide of formula I or II in admixture with a pharmaceutically acceptable carrier or excipient, and a method for treating renin-associated hypertension in a patient suffering therefrom comprising administering to said patient the above pharmaceutical composition in unit dosage form.

Further the present invention also includes a pharmaceutical composition comprising an effective amount of an above modified peptide of formula I or II in admixture with a pharmaceutically acceptable carrier or excipient, and a method for treating hyperaldosteronism in a patient suffering therefrom comprising administering to said patient the above pharmaceutical composition in unit dosage form.

The present invention also includes novel intermediates used to prepare the novel peptides.

DETAILED DESCRIPTION

The following table provides a dictionary of the terms used in the description of the present invention.

TABLE I

| Abbreviated Designation | Amino Acid |
|---|---|
| ARG | L-arginine |
| ARG (NO₂) | L-nitroarginine |
| CYCLOHEXYLALA | Cyclohexylalanine |
| CYSTA, CYCLOTINE | 4($\underline{S}$)—amino-3($\underline{S}$)—hydroxy-5-cyclohexanepentanoic acid |
| GLY | Glycine |
| HIS | L-histidine |
| HIS(BOM) | Histidinebenzyloxymethyl |
| HOMOPHE | Homophenylalanine |
| ILE | L-isoleucine |
| LEU | L-leucine |
| (Me⁵)PHE | Pentamethylphenylalanine |
| NAPHTHYLALA | 1-Naphthylalanine |
| ORN | L-ornithine |
| ORN(PHT) | L-Ornithine (phthalolyl) |
| PHE | L-phenylalanine |
| PHGLY | Phenylglycine |
| PHSTA, BENZTINE | 4($\underline{S}$)—Amino-3($\underline{S}$)—hydroxy-5-phenylpentanoic acid |
| STA | Statine |
| TRP | L-tryptophan |
| VAL | L-valine |
| Protecting Groups | |
| BOC | Tert-butyloxycarbonyl |
| IBU | Isobutyryl |
| IVA | Isovaleryl |
| NVA | n-Valeryl |
| Z | Benzyloxycarbonyl |
| Amides with | |
| —NHCH₂Ph | Benzylamine |
| 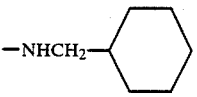 | Cyclohexylmethylamine |
| 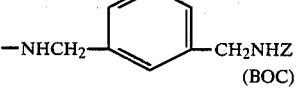 | m-xylene-di-amine (Z or BOC) |
| 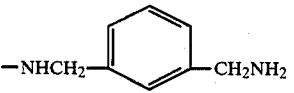 | m-xylene-di-amine |
| —NH₂ | Ammonia |
| 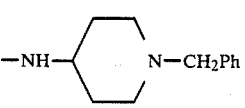 | 4-Amino-N—benzyl-piperidine |

TABLE I-continued

| Abbreviated Designation | Amino Acid |
|---|---|
| 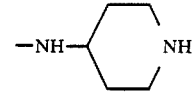 | 4-Aminopiperidine |
| 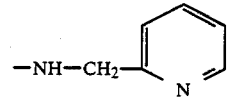 | 2-Aminomethylpyridine |
| 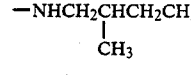 | 2-Methylbutylamine |
| Esters with | |
| —OCH₃ | Methanol |
| —OC₂H₅ | Ethanol |

The peptides of the present invention are represented by the formula $$\text{ACYL-X-(A)}_n\text{-Y-(B)}_n\text{-T-(C)}_n\text{-W-(D)}_n\text{-V-(E)}_n\text{-U} \quad (I)$$

and the pharmaceutically acceptable acid addition salts thereof, wherein
 n is 0 or 1, and the compound must contain at least 1 link where n is 1,
 acyl is BOC, NVA, Z, IVA, IBU, benzoyl,

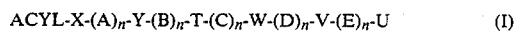
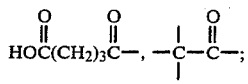

X is PHE, TRP, CYCLOHEXYLALA, NAPHTHYLALA, HOMOPHE, (Me⁵)-PHE, VAL, ILE, or LEU;
Y is absent, PHE, HIS, HIS(BOM), GLY, PHGLY, LEU, VAL, ILE, ORN, ORN(PHT), ARG, or ARG(NO₂);
T is STA, PHSTA, CYSTA, LEU, CYCLOHEXYLALA or PHE;
W is absent, LEU, GLY, or ILE;
V is absent, LEU, or ILE;
U is

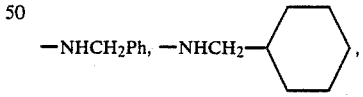

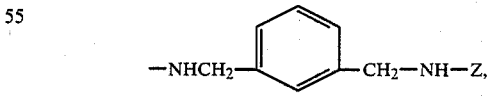

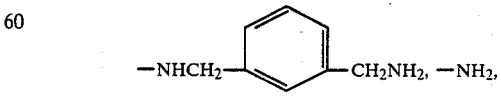

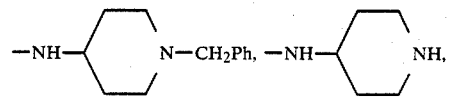

-continued

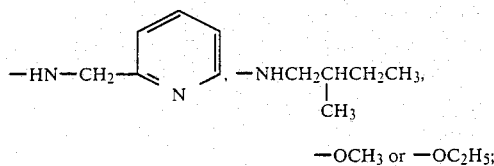

A is

—CH$_2$NH—, —CH$_2$NOH—, —CH$_2$S—, —CH$_2$SO—,

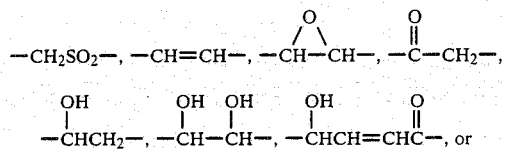

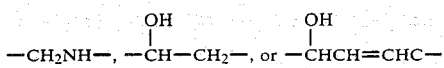

B is —CH$_2$NH—;
C is

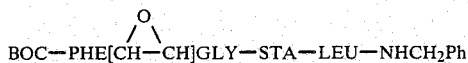

D is —CH$_2$NH—; and
E is —CH$_2$NH—, —CH$_2$NHZ.

Particularly valuable compounds falling within the scope of the present invention include the following compounds and their isomers:

BOC—PHE[CH=CH]GLY—STA—LEU—NHCH$_2$Ph
BOC—PHE[CH=CH]GLY—PHSTA—LEU—NHCH$_2$Ph

IVA—PHE[CH=CH]GLY—STA—LEU—NHCH$_2$Ph
BOC—PHE[CH=CH]GLY—CYSTA—LEU—NHCH$_2$Ph

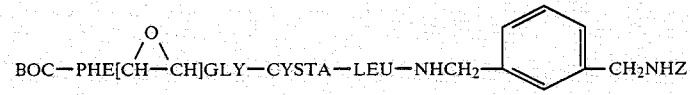

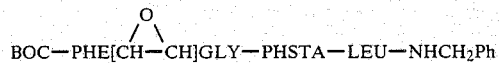

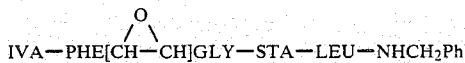

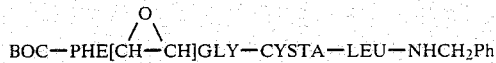

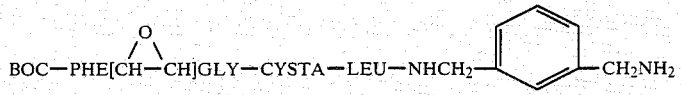

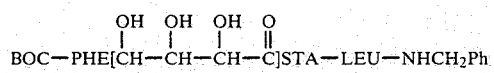

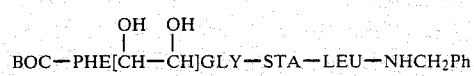

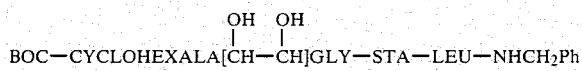

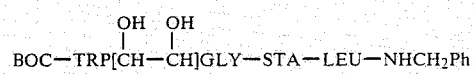

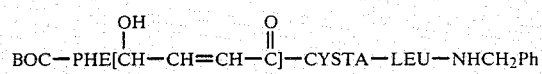

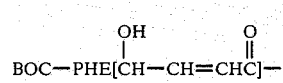

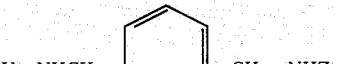

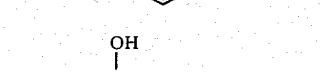

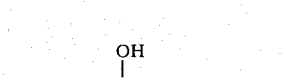

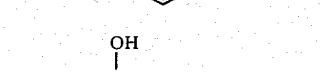

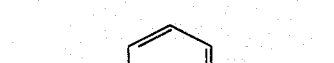

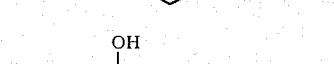

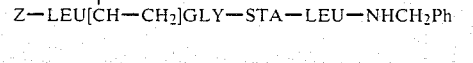

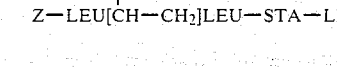

-continued

IVA—PHE—HIS—CYCLOHEXALA[CH(OH)—CH₂]GLY—NHCH₂Ph

IVA—PHE—HIS—CYCLOHEXALA[CH(OH)—CH₂]GLY—LEU—NHCH₂Ph

Z—PHE[CH(OH)—CH₂]PHE—STA—LEU—NHCH₂Ph

BOC—PHE[CH(OH)—CH₂]HIS—STA—LEU—NHCH₂Ph

BOC—PHE[CH(OH)—CH₂]HIS—STA—LEU—NHCH₂Ph (isomer)

IVA—LEU[C(O)—CH₂]PHE—STA—LEU—NHCH₂Ph

Z—LEU[CH(OH)—CH₂]PHE—STA—LEU—NHCH₂Ph

Z—LEU[C(O)—CH₂]PHE—STA—LEU—NHCH₂Ph

BOC—PHE[CH₂CH₂]GLY—STA—LEU—NHCH₂Ph

BOC—PHE[CH₂CH₂]GLY—CYSTA—LEU—NHCH₂—C₆H₄—CH₂NH₂

IVA—PHE[CH₂S]PHE—STA—LEU—NHCH₂Ph

BOC—PHE[CH₂SO]PHE—STA—LEU—NHCH₂Ph

IVA—PHE[CH₂S]GLY—STA—LEU—NHCH₂Ph

HO₂C(CH₂)₃C(O)—PHE[CH₂S]PHE—STA—LEU—NHCH₂Ph

BOC—PHE[C(O)—CH₂]GLY—STA—LEU—NHCH₂Ph

IVA—PHE[C(O)—CH₂]GLY—STA—LEU—NHCH₂Ph

Z—PHE[C(O)—CH₂]PHE—STA—LEU—NHCH₂Ph

BOC—CYCLOHEXYLALA[C(O)—CH₂]LEU—STA—LEU—NHCH₂Ph

IVA—VAL[CH₂NH]VAL—STA—OEt
IVA—VAL[CH₂NH]VAL—STA—LEU—NHCH₂Ph
IVA—PHE—HIS—STA—LEU[CH₂NZ]CH₂Ph
BOC—PHE[CH₂NH]PHE—STA—LEU—NHCH₂Ph

IVA—VAL[CH₂NH]VAL—STA—NHCH₂Ph
BOC—PHE—VAL—STA—LEU[CH₂NZ]CH₂Ph
IVA—PHE—HIS—STA—LEU[CH₂NH]CH₂Ph

BOC—D—PHE(Me⁵)[CH₂NH]HIS—STA—LEU—NH—(piperidine)N—CH₂Ph

BOC—PHE[CH₂NH]HIS(BOM)—STA—LEU—NHCH₂Ph
IVA—PHE—HIS—LEU[CH₂NH]LEU—NHCH₂Ph
BOC—PHE[CH₂NOH]PHE—STA—LEU—NHCH₂Ph
BOC—PHE[CH₂NOH]HIS—STA—LEU—NHCH₂Ph
IVA—ILE[CH₂NH]VAL—STA—LEU—NHCH₂Ph
IVA—ILE[CH₂NH]ILE—STA—LEU—NHCH₂Ph

BOC—PHE[CH₂NH]HIS—STA—LEU—NHCH₂Ph
IVA—PHE—HIS[CH₂NH]STA—LEU—NHCH₂Ph
BOC—CYCLOHEXYLALA[CH₂NH]HIS—STA—LEU—NHCH₂Ph
IVA—PHE—HIS—CYCLOHEXYLALA[CH₂NH]LEU—NHCH₂Ph
IVA—ILE[CH₂NH]VAL—STA—LEU—NHCH₂Ph (isomer)
BOC—PHE[CH₂NH]HIS—PHSTA—LEU—NHCH₂Ph IVA—PHE—HIS—LEU[CH(OH)—CH₂]LEU—NHCH₂Ph

Z—NAPHTHYLALA—HIS—CYCLOHEXYLALA[CHOHCH₂]GLY—NH—CH₂CH(CH₃)CH₂CH₃

IVA—PHE—HIS—CYCLOHEXYLALA[CH(OH)—CH₂]LEU—NHCH₂Ph

BOC—CYCLOHEXYLALA[CH(OH)—CH₂]LEU—STA—LEU—NHCH₂Ph

IVA—PHE—HIS—CYCLOHEXYLALA[CHOHCH₂]GLY—NHCH₂—C₆H₄—CH₂NH₂

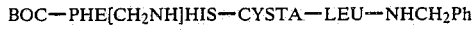

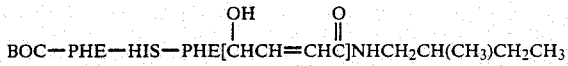

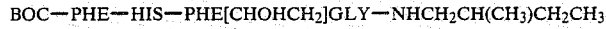

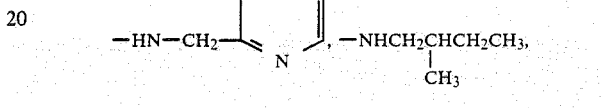

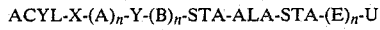

Other peptides of the present invention are represented by formula

ACYL-X-(A)$_n$-Y-(B)$_n$-STA-ALA-STA-(E)$_n$-U  (II)

and the pharmaceutically acceptable acid addition salts thereof wherein n is 0 or 1, and the compound must contain at least 1 link where n is 1, acyl is BOC, NVA, Z, IVA, IBU, benzoyl,

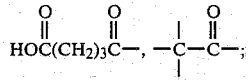

X is PHE, TRP, CYCLOHEXYLALA, NAPHTHYLALA, HOMOPHE, (Me$^5$)-PHE, VAL, ILE, or LEU;

Y is absent, PHE, HIS, HIS(BOM), GLY, PHGLY, LEU, VAL, ILE, ORN, ORN(PHT), ARG, or ARG(NO$_2$);

T is STA, PHSTA, CYSTA, LEU, or CYCLOHEXYLALA;

W is absent, LEU, GLY, or ILE;

V is absent, LEU, or ILE;

U is

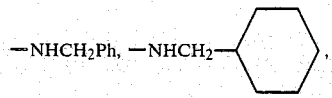

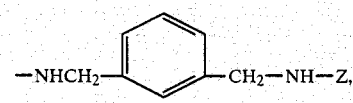

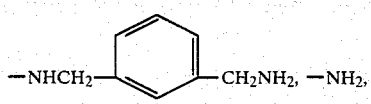

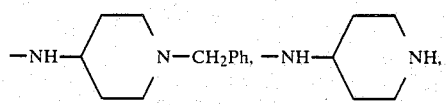

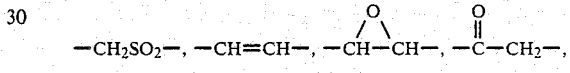

-OCH$_3$ or -OC$_2$H$_5$;

A is

-CH$_2$NH-, -CH$_2$NHOH-, -CH$_2$S-, -CH$_2$SO-,

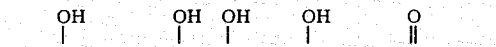

B is -CH$_2$NH-; and

E is -CH$_2$NH-, -CH$_2$NZ.

Particularly preferred compounds falling within the scope of the present invention include the following compounds and their isomers:

BOC—PHE[CH=CH]GLY—STA—ALA—STA—NHCH$_2$Ph
BOC—PHE[CH=CH]PHE—STA—ALA—STA—NHCH$_2$Ph
IVA—PHE[CH$_2$S]PHE—STA—ALA—STA—NHCH$_2$Ph
IVA—PHE[CH$_2$SO$_2$]PHE—STA—ALA—STA—NHCH$_2$Ph
IVA—PHE[CH$_2$SO]PHE—STA—ALA—STA—NHCH$_2$Ph
BOC—PHE[CH$_2$SO$_2$]PHE—STA—ALA—STA—NHCH$_2$Ph
BOC—PHE[CH$_2$SO]PHE—STA—ALA—STA—NHCH$_2$Ph $$\text{PhC}\overset{\overset{O}{\|}}{-}\text{PHE}[\overset{\overset{O}{\|}}{C}-\text{CH}_2]\text{GLY—STA—ALA—STA—NHCH}_2\text{Ph}$$

$$\text{BOC—PHE}[\overset{\overset{O}{\|}}{C}-\text{CH}_2]\text{GLY—STA—ALA—STA—NHCH}_2\text{Ph}$$

IVA—VAL[CH$_2$NH]VAL—STA—ALA—STA—NHCH$_2$Ph
BOC—PHE[CH$_2$NH]PHE—STA—ALA—STA—NHCH$_2$Ph
BOC—PHE[CH$_2$NH]HIS—STA—ALA—STA—NHCH$_2$Ph
BOC—LEU[CH$_2$O]PHGLY—STA—ALA—STA—NHCH$_2$Ph.

The compounds include solvates and hydrates and pharmaceutically acceptable acid addition salts of the basic compounds of formulae I and II above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicyclic, malic, gluconic, fumaric, succinic, ascorbic, maleic, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular isostere and the particular final product desired. Others were prepared by novel processes detailed below. These processes are not intended to be exhaustive.

Compounds as represented by Examples 16, 17, and 18 were made by a novel process as shown in the following scheme.

dihydroxy isosteres by reaction with osmium tetroxide in dioxane.

Compounds of the type in Example 15 were produced by a unique process represented by

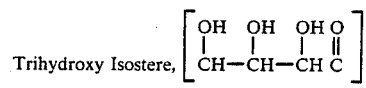

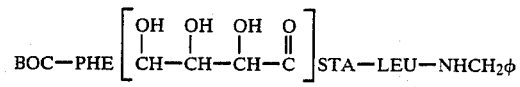

Here the compound containing the double bond was treated with osmium tetroxide in dioxane to produce the corresponding trihydroxyisostere.

Examples 19, 20, and 21, were prepared by a unique, alternate route for compounds of the hydroxy double bond type. These compounds were then reduced with Raney nickel to give compounds as in Examples 22, 23, and 24.

The following scheme represents this unique process:

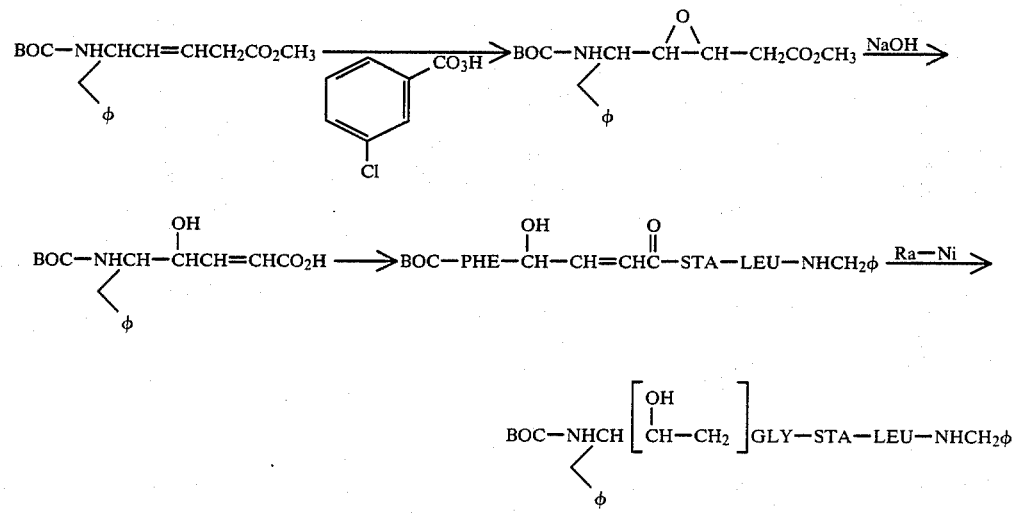

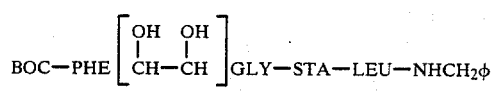

The isosteres defined by i.e. A containing the C=C functional group were converted to the corresponding The phenylhex-2-enoic acid, methyl ester was treated with meta-chloroperbenzoic acid to form the corresponding epoxide. This epoxide was reacted with a strong base to give the corresponding 4-hydroxyphenylhex-2-enoic acid. That compound is reacted with HCl.STA-LEU-NHCH$_2$Ph in N,N-dimethylformamide to give the desired corresponding hydroxy double bond isostere.

These isosteres were hydrogenated with Raney nickel, as in Examples 22, 23, and 24 to give the corresponding hydroxyethylene isosteres.

Compounds of the type in Example 49 were prepared by the novel process as shown in the following scheme.

Process Flow Sheet For [C(=O)—CH$_2$] and [CH(OH)—CH$_2$] Isosteres

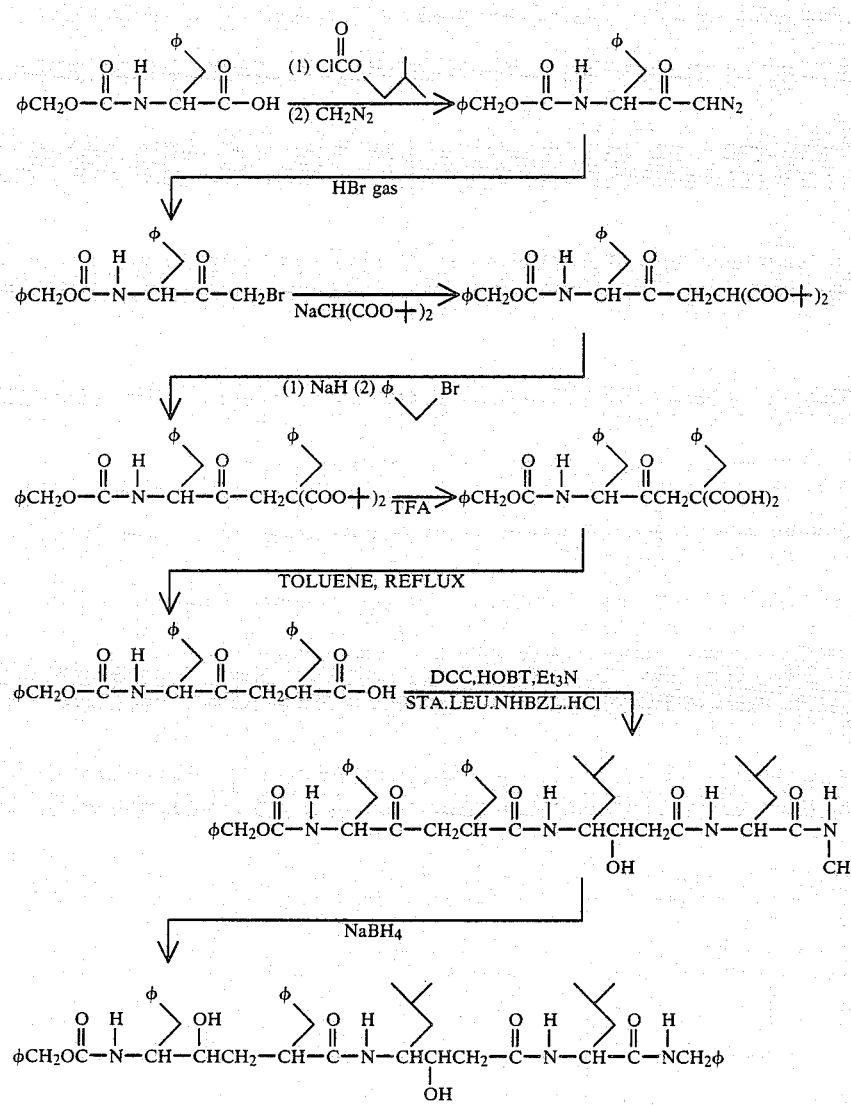

Example 67 was prepared by a unique one-step process which was represented by the following scheme:

METHYLENEHYDROXYAMINO ISOSTERE [CH$_2$NOH]

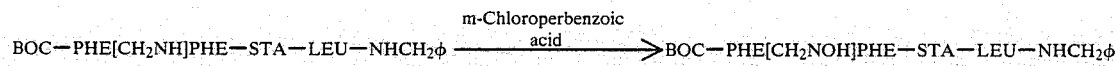

The secondary amine is oxidized to the hydroxylamine using meta-chloroperbenzoic acid in dichloromethane. The reaction is carried out at ambient temperature.

The compounds of the present invention are useful for treating renin-associated hypertension and hyperaldsteronism.

Pharmaceutical compositions which comprise an effective amount of the compound in combination with a pharmaceutically acceptable carrier are part of the present invention. An important aspect of the present invention is a method of treating renin associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldeosteronism in a mammal which comprises administering a pharmaceutical composition containing an effective amount of a compound of the invention in combination with a pharmaceutically acceptable carrier to the mammal.

The present invention also includes novel intermediates used in making the novel peptides of the present invention.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

| Example Number | Activity ($IC_{50}$) |
| --- | --- |
| 1 | $8.2 \times 10^{-6}$ |
| 2 | $1.2 \times 10^{-5}$ |
| 3 | $7.0 \times 10^{-6}$ |
| 4 | $1.3 \times 10^{-5}$ |
| 5 | $9.2 \times 10^{-6}$ |
| 6 | $1.3 \times 10^{-6}$ |
| 7 | $2.0 \times 10^{-5}$ |
| 8 | $8.0 \times 10^{-6}$ |
| 9 | $1.2 \times 10^{-6}$ |
| 10 | $2.9 \times 10^{-5}$ |
| 11 | $4.4 \times 10^{-6}$ |
| 12 | $5.3 \times 10^{-7}$ |
| 13 | $2.6 \times 10^{-6}$ |
| 14 | $3.2 \times 10^{-7}$ |
| 15 | $1.1 \times 10^{-5}$ |
| 16 | $1.4 \times 10^{-6}$ |
| 17 | $6.5 \times 10^{-6}$ |
| 18 | $2.3 \times 10^{-6}$ |
| 19 | $2.1 \times 10^{-6}$ |
| 20 | $9.0 \times 10^{-8}$ |
| 21 | $4.7 \times 10^{-7}$ |
| 22 | $6.4 \times 10^{-7}$ |
| 23 | $6.1 \times 10^{-8}$ |
| 24 | $2.2 \times 10^{-8}$ |
| 25 | $4.0 \times 10^{-6}$ |
| 26 | $6.7 \times 10^{-6}$ |
| 27 | $2.5 \times 10^{-7}$ |
| 28 | $1.4 \times 10^{-8}$ |
| 29 | $3.7 \times 10^{-6}$ |
| 30 | $3.0 \times 10^{-5}$ |
| 31 | $7.8 \times 10^{-7}$ |
| 32 | $7.1 \times 10^{-6}$ |
| 33 | $8.4 \times 10^{-6}$ |
| 34 | $1.1 \times 10^{-5}$ |
| 35 | $2.3 \times 10^{-5}$ |
| 36 | $6.3 \times 10^{-5}$ |
| 37 | $7.4 \times 10^{-6}$ |
| 38 | $1.5 \times 10^{-6}$ |
| 39 | $3.0 \times 10^{-5}$ |
| 40 | $2.0 \times 10^{-6}$ |
| 41 | $1.8 \times 10^{-5}$ |
| 42 | $5.6 \times 10^{-6}$ |
| 43 | $5.4 \times 10^{-6}$ |
| 44 | $3.0 \times 10^{-5}$ |
| 45 | $1.8 \times 10^{-5}$ |
| 46 | $2.1 \times 10^{-5}$ |
| 47 | $2.6 \times 10^{-5}$ |
| 48 | $3.0 \times 10^{-5}$ |
| 49 | $2.3 \times 10^{-5}$ |
| 50 | $3.0 \times 10^{-5}$ |
| 51 | $2.6 \times 10^{-5}$ |
| 52 | $1.8 \times 10^{-5}$ |
| 53 | $2.8 \times 10^{-5}$ |
| 54 | $3.0 \times 10^{-5}$ |
| 55 | $1.5 \times 10^{-5}$ |
| 56 | $1.6 \times 10^{-5}$ |
| 57 | $3.0 \times 10^{-6}$ |
| 58 | $1.9 \times 10^{-6}$ |
| 59 | $5.6 \times 10^{-6}$ |
| 60 | $4.2 \times 10^{-6}$ |
| 61 | $3.0 \times 10^{-5}$ |
| 62 | $1.6 \times 10^{-5}$ |
| 63 | $2.1 \times 10^{-5}$ |
| 64 | $3.8 \times 10^{-6}$ |
| 65 | $7.7 \times 10^{-6}$ |
| 66 | $3.5 \times 10^{-6}$ |
| 67 | $1.8 \times 10^{-5}$ |
| 68 | $1.0 \times 10^{-5}$ |
| 69 | $6.5 \times 10^{-6}$ |
| 70 | $2.8 \times 10^{-7}$ |
| 71 | $3.0 \times 10^{-5}$ |

-continued

| Example Number | Activity ($IC_{50}$) |
| --- | --- |
| 72 | $1.8 \times 10^{-5}$ |
| 73 | $3.0 \times 10^{-5}$ |
| 74 | $3.8 \times 10^{-6}$ |
| 75 | $2.0 \times 10^{-5}$ |
| 76 | $7.4 \times 10^{-7}$ |
| 77 | $1.6 \times 10^{-6}$ |
| 78 | $2.4 \times 10^{-7}$ |
| 79 | $3.8 \times 10^{-6}$ |
| 80 | $2.1 \times 10^{-6}$ |
| 81 | $5.4 \times 10^{-8}$ |
| 82 | $1.2 \times 10^{-7}$ |
| 83 | $2.0 \times 10^{-7}$ |
| 84 | $1.4 \times 10^{-6}$ |
| 85 | $7.5 \times 10^{-8}$ |

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg of body weight per day or perferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples are provided to enable one skilled in the art to practice the present invention. These examples are not intended in any way to limit the scope of the invention but are illustrative thereof.

EXAMPLE 1

BOC-PHE[CH=CH]GLY-STA-ALA-STA-NHCH$_2$Ph

A solution of 250 mg (0.5 mmole) of STA-ALA-STA-NHCH$_2$Ph, 155 mg (0.5 mmole) of [S-(E)]-5-[[(1,1-dimethylethoxy)carbonyl]amino]-6-phenyl-3-hexenoic acid (J. Chem. Soc. 799 (1980)), and 68 mg (0.5 mmole) of hydroxybenzotriazole in 15 ml of N,N-dimethylformamide was cooled in ice and treated rapidly with a solution of 106 mg (0.5 mmole) of N,N'-dicyclohexylcarbodiimide in 5 ml of N,N-dimethylformamide. After one hour at 0°, the mixture was allowed to stir at room temperature overnight. The solvent was then removed under reduced pressure and the residue taken up in ethyl acetate. The precipitated N,N'-dicyclohexylurea was filtered off and the filtrate was washed with 1N HCl, saturated NaHCO$_3$, and then saturated NaCl. Drying over MgSO$_4$ and removal of the solvent under reduced pressure gave 340 mg of crude product. After chromatography on silica gel, eluting with CHCl$_3$—MeOH (19/1) there was obtained 240 mg of pure product, [5S-[5R*,6R*,9R*,13R*,14R*-(E),20R*]]-5,13-dihydroxy-9-methyl-6,14-bis(2-methylpropyl)-3,8,11,16-tetraoxo-1-phenyl-20-(phenylmethyl)-2,7,10,15,21-pentaazadocos-18-en-22-oic acid, 1,1-dimethylethyl ester. This compound could also be designated as BOC-PHE[CH=CH]GLY-STA-ALA-STA-NHCH$_2$Ph.

Calcd. for C$_{43}$H$_{65}$N$_5$O$_8$·0.3CH$_2$Cl$_2$ (MW 805.47): C, 64.56; H, 8.21; N, 8.70. Found: C, 64.42; H, 8.29; N, 8.79.

The structure was also confirmed by NMR and MS spectroscopy.

EXAMPLE 2

BOC-PHE[CH=CH]PHE-STA-ALA-STA-NHCH$_2$Ph

A solution of 291 mg (0.59 mmole) of STA-ALA-STA-NHCH$_2$Ph, 233 mg (0.59 mmole) of (E)-α-[3-[[(1,1-dimethylethoxy)carbonyl]amino]-4-phenyl-1-butenyl]benzenepropanoic acid (J. Chem. Soc. 799 (1980)), and 80 mg (0.59 mmole) of hydroxybenzotriazole in 15 ml of N,N-dimethylformamide was cooled in ice and treated rapidly with a solution of 123 mg (0.59 mmole) of N,N'-dicyclohexylcarbodiimide in 5 ml of N,N-dimethylformamide. After one hour at 0°, the mixture was allowed to stir at room temperature overnight. The solvent was then removed under reduced pressure and the residue taken up in ethyl acetate. The precipitated N,N'-dicyclohexylurea was filtered off and the filtrate was washed with 1N HCl, saturated NaHCO$_3$, then saturated NaCl. Drying over MgSO$_4$ and removal of the solvent under reduced pressure gave 450 mg of crude product. After chromatography on silica gel, eluting with CHCl$_3$—MeOH (19/1) there was obtained 300 mg of pure product, (E)-5,13-dihydroxy-9-methyl-6,14-bis(2-methylpropyl)-3,8,11,16-tetraoxo-1-phenyl-17,20-bis(phenylmethyl)-2,7,10,15,21-pentaazadocos-18-en-22-oic acid, 1,1-dimethylethyl ester. This compound could also be designated as BOC-PHE[CH=CH]PHE-STA-ALA-STA-NHCH$_2$Ph.

Calcd. for C$_{50}$H$_{71}$N$_5$O$_8$ (MW 870.11): C, 69.01; H, 8.23; N, 8.05. Found: C, 68.82; H, 8.12; N, 7.91.

The structure was also confirmed by NMR and MS spectroscopy. The compound has an $[\alpha]_D^{23} = -34.4°$ (C, 1.11, CH$_3$OH).

EXAMPLE 3

BOC-PHE[CH=CH]GLY-STA-LEU-NHCH$_2$Ph

A solution of 400 mg (0.97 mmole) of the hydrochloride salt of STA-LEU-NHCH$_2$Ph, 295 mg (0.97 mmole) of [S-(E)]-5-[[(1,1-dimethylethoxy)carbonyl]amino]-6-phenyl-3-hexenoic acid (J. Chem. Soc. 799 (1980)), and 131 mg (0.97 mmole) of hydroxybenzotriazole in 25 ml of N,N-dimethylformamide was cooled in ice and 0.14 ml (0.97 mmole) of triethylamine added followed by a solution of 202 mg (0.97 mmole) of N,N'-dicyclohexylcarbodiimide in 5 ml of N,N-dimethylformamide. After 0.5 hour at 0°, the mixture was allowed to stir at room temperature overnight. The solvent was then removed under reduced pressure and the residue taken up in ethyl acetate. The precipitated N,N'-dicyclohexylurea was filtered off and the filtrate was washed with 1N HCl, saturated NaHCO$_3$, and then with saturated NaCl. Drying over MgSO$_4$ and removal of the solvent under reduced pressure gave 640 mg of crude product. After chromatography on silica gel, eluting with CHCl$_3$—MeOH (32/1) there was obtained 430 mg of pure product, [4S-(4R*,8R*,9R*,13E,15R*)]-8-hydroxy-4,9-bis(2-methylpropyl)-1-phenyl-15-(phenyl-methyl)-3,6,11-trioxo-2,5,10,16-tetraazaheptadec-13-en-17-oic acid, 1,1-dimethylethyl ester. This compound could also be designated as BOC-PHE[CH=CH]GLY-STA-LEU-NHCH$_2$Ph.

Calcd. for C$_{38}$H$_{56}$N$_4$O$_6$.0.3H$_2$O (MW 670.26): C, 68.09; H, 8.51; N, 8.36. Found: C, 68.12; H, 8.62; N, 8.38.

The structure was also confimred by NMR and MS spectroscopy. The compound had an $[\alpha]_D^{23} = -25.6°$ (C, 1.04, CH$_3$OH).

EXAMPLE 4

IVA-PHE[CH=CH]GLY-STA-LEU-NHCH$_2$Ph

A solution of 290 mg (1.0 mmole) of [S-(E)]-5-[(3-methyl-1-oxobutyl)amino]-6-phenyl-3-hexenoic acid, 414 mg (1.0 mmole) of HCL.STA-LEU-NHCH$_2$Ph, and 136 mg (1.0 mmole) of hydroxybenzotriazole in 20 ml of N,N-dimethylformamide was cooled in ice and treated with 0.14 ml (1.0 mmole) of triethylamine followed by a solution of 209 mg (1.0 mmole) of N,N'-dicyclohexylcarbodiimide in 5 ml of N,N-dimethylformamide. After one hour at 0°, the mixture was allowed to stir at room temperature overnight. The solvent was then removed under reduced pressure and the residue taken up in ethyl acetate. The precipitated N,N'-dicyclohexylurea was filtered off and the filtrate was extracted with 1N HCl, H$_2$O, saturated NaHCO$_3$, then saturated NaCl. Drying over MgSO$_4$ and removal of the solvent under reduced pressure gave 520 mg of a foam. After chromatography on silica gel, eluting with CHCl$_3$—CH$_3$OH (24/1) there was obtained 340 mg of pure product, [3S-[N(R*),3R*,4R*(3E,5R*)]]-3--hydroxy-6-methyl-4-[[5-[(3-methyl-1-oxobutyl)amino]-1-oxo-6-phenyl-3-hexenyl]amino]-N-[3-methyl-1-[[(phenylmethyl)amino]carbonyl]butyl]heptanamide. This compound could also be designated as IVA-PHE[CH=CH]GLY-STA-LEU-NHCH$_2$Ph.

Calcd. for C$_{38}$H$_{56}$N$_4$O$_5$ (MW 648.86): C, 70.34; H, 8.70; N, 8.64. Found: C, 70.44; H, 8.61; N, 8.54.

The structure was also confirmed by NMR and MS spectroscopy.

EXAMPLE 5

BOC-PHE[CH=CH]GLY-PHSTA-LEU-NHCH$_2$Ph

A solution of 190 mg (0.42 mmole) of PHSTA-LEU-NHCH$_2$Ph.HCl, 129 mg (0.42 mmole) of BOC-PHE[CH=CH]GLY and 57.3 mg (0.42 mmole) of hydroxybenzotriazole in 10 ml of N,N-dimethylformamide was treated with 0.06 ml (0.42 mmole) of triethylamine and then cooled to 0°. A solution of 87.3 mg (0.42 mmole) of N,N'-dicyclohexylcarbodiimide in 5 ml of N,N'-dimethylformamide was added and the solution was kept at 0° for one hour and then allowed to warm to room temperature overnight. The solvent was removed under reduced pressure, the residue was dissolved in ethyl acetate, and the precipitated N,N'-dicyclohexylurea filtered off. This solution was washed with 1N HCl, saturated NaHCO$_3$ and saturated NaCl, dried and the solvent was removed under reduced pressure to give 0.28 g of a solid. The solid was chromatographed on silica gel eluting with chloroform-methanol (98/2), the appropriate fractions were combined to give 0.22 g (74%) of BOC-PHE[CH=CH]GLY-PHSTA-LEU-NHCH$_2$Ph, 2,5,10,16-tetraazaheptadec-13-en-17-oic acid, 8-hydroxy-4-(2-methylpropyl)-3,6,11-trioxo-1-phenyl-9,15-bis(phenyl-methyl)-,1,1-dimethyl ester, as a white solid.

Calcd. for C$_{41}$H$_{54}$N$_4$O$_6$.0.2CHCl$_3$ (MW 722.75): C, 68.46; H, 7.56; N, 7.75. Found: C, 68.04; H, 7.73; N, 7.52.

EXAMPLE 6

BOC-PHE[CH=CH]GLY-CYSTA-LEU-NHCH$_2$Ph

A solution of 300 mg (0.98 mmole) of BOC-PHE[CH=CH]GLY, 446 mg (0.98 mmole) of CYSTA-LEU-NHCH$_2$Ph.HCl and 132 mg (0.98 mmole) of hydroxybenzotriazole in 15 ml of N,N-dimethylformamide was cooled to 0° and 0.137 ml (0.98 mmole) of triethylamine was added. After 10 minutes a solution of 202 mg (0.98 mmole) of N,N'-dicyclohexylcarbodiimide in 5 ml of N,N-dimethylformamide was added, the solution was maintained at 0° for one hour and then allowed to warm to room temperature overnight. The solvent was removed under reduced pressure, the residue was brought up in ethyl acetate, and the precipitated N,N'-dicyclohexylurea filtered off. The organic solution was washed with 1N HCl, saturated NaHCO$_3$, saturated NaCl and dried. The solvent was removed under reduced pressure to yield 0.72 g of a brown solid. The solid was chromatographed on silica gel eluting with chloroform-methanol (98/2). The appropriate fractions were combined to afford 0.510 g (73.3%) of BOC-PHE[CH=CH]GLY-CYSTA-LEU-NHCH$_2$Ph, Calcd. for C$_{41}$H$_{60}$N$_4$O$_6$.0.1CHCl$_3$ (MW 716.86). C, 68.85; H, 8.45, N, 7.82. Found: C, 68.71; H, 8.66, N, 7.66. $[\alpha]_D^{25} = -23.1°$ (C, 1.2, MeOH).

EXAMPLE 7

BOC-TRP[CH=CH]GLY-STA-LEU-NHCH$_2$Ph

A solution of 861 mg (2.5 mmole) of [S-(E)]-5-[[(1,1-dimethylethoxy)carbonyl]amino]-6-(3-indolyl)-3-hexenoic acid, 1.035 g (2.5 mmole) of STA-LEU-NHCH$_2$Ph.HCl, 1.035 g (2.5 mmole) of hydroxybenzotriazole in 30 ml of N,N-dimethylformamide was cooled in ice and treated with 0.35 ml (2.5 mmole) of triethylamine followed by a solution of 521 mg (2.5 mmole) of N,N'-dicyclohexylcarbodiimide in 5 ml of N,N-dimethylformamide. After stirring at 0° for one hour, the solution was allowed to stir at room temperature overnight. The solvent was removed under reduced pressure and the residue taken up in ethyl acetate. The precipitated N,N'-dicyclohexylurea was filtered off and the filtrate extracted with 1N citric acid, water, saturated NaHCO$_3$, then saturated NaCl. Drying over MgSO$_4$ and removal of the solvent under reduced pressure left 1.76 g of crude product. After chromatography on silica gel, eluting with chloroform-methanol (24/1) there was obtained 1.25 g of product, [4S-(4R*,8R*,9R*,-13E,15R*)]-8-hydroxy-15-(1H-indol-3-ylmethyl)-4,9-bis(2-methylpropyl)-3,6,11-trioxo-1-phenyl-2,5,10-16-tetraazaheptadec-13-en-17-oic acid, 1,1-dimethylethyl ester. The compound could also be designated as BOC-TRP[CH=CH]GLY-STA-LEU-NHCH$_2$Ph.

Calcd. for C$_{40}$H$_{57}$N$_5$O$_6$.0.4CHCl$_3$ (MW 751.65): C, 64.55; H, 7.70; N, 9.32. Found: C, 64.31; H, 7.77; N, 9.22.

The structure was confirmed by NMR and MS spectroscopy.

EXAMPLE 8

A solution of 366 mg (1.2 mmole) of BOC-PHE[CH=CH]GLY, 750 mg (1.2 mmole) of

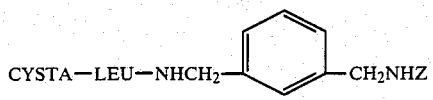

and 162 mg (1.2 mmole) of hydroxybenzotriazole in 15 ml N,N-dimethylformamide was cooled to 0° and 0.167 ml (1.2 mmole) of triethylamine was added. After ten minutes a solution of 248 mg (1.2 mmole) of dicyclohexylcarbodiimide in 5 ml of N,N-dimethylformamide was added, the mixture was kept at 0° for one hour and then allowed to warm to room temperature overnight. The solvent was removed under reduced pressure, the residue was dissolved in ethyl acetate, and the precipitated N,N'-dicyclohexylurea filtered off. The organic solution was washed with 1N HCl, H₂O, saturated NaHCO₃ and saturated NaCl. The solution was dried and the solvent was removed under reduced pressure to yield 1.12 g of a foam. After chromatography on silica gel, eluting with chloroform-methanol (99/1), the appropriate fractions were combined and concentrated to afford 0.76 g (72.4%)

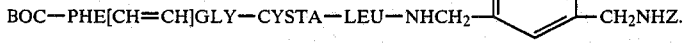

Calcd. for $C_{50}H_{69}N_5O_8.0.6CHCl_3$ (MW 939.72): C, 64.67; H, 7.47; N, 7.45. Found: C, 64.39; H, 7.27; N, 7.36.

EXAMPLE 9

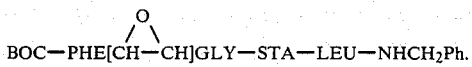

A solution of 870 mg (1.3 mmole) of BOC-PHE[CH=CH]GLY-STA-LEU-NHCH₂Ph in 20 ml of dichloromethane was treated with 409 mg (2.0 mmole) of m-chloroperbenzoic acid and allowed to stir at room temperature for 3 days. The solution was diluted with dichloromethane and washed with 10% Na₂SO₃, H₂O, saturated NaHCO₃, then saturated NaCl. Drying over MgSO₄ and removal of the solvent under reduced pressure gave 800 mg of crude product. After chromatography on silica gel, eluting with CHCl₃-MeOH (32/1) there was obtained 620 mg of pure product, [1-[3-[2-[[2-hydroxy-1-(2-methylpropyl)-4-[[3-methyl-1-[[(phenylmethyl)amino]carbonyl]butyl]amino]-4-oxabutyl]amino]-2-oxoethyl]-2-oxiranyl]-2-phenylethyl]carbamic acid, 1,1-dimethylethyl ester. This compound could also be designated as

Calcd. for $C_{38}H_{56}N_4O_7.0.15CHCl_3$ (MW 698.77): C, 65.57; H, 8.10; N, 8.02. Found: C, 65.23; H, 8.18; N, 8.44.

The structure was also confirmed by NMR and MS spectroscopy. The stereochemistry at the epoxide is unknown.

EXAMPLE 10

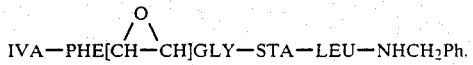

A solution of 260 mg (0.4 mmole) of IVA-PHE[CH=CH]GLY-STA-LEU-NHCH₂Ph in 10 ml of dichloromethane was treated with 125 mg (0.6 mmole) of m-chloroperbenzoic acid and left stirring at room temperature for 3 days. The solution was then diluted with dichloromethane and washed two times with a 10% solution of sodium bisulfite, 1N HCl, 1N NaOH, then saturated NaCl. Drying over MgSO₄ and removal of the solvent under reduced pressure left 260 mg of crude epoxide. After chromatography on silica gel, eluting with CHCl₃—CH₃OH (32/1) there was obtained 100 mg of pure product, N-[2-hydroxy-4-[[3-methyl-1-[[(phenylmethyl)amino]carbonyl]butyl]amino]-1-(2-methylpropyl)butyl]-3-[1-[(3-methyl-1-oxobutyl)amino]-2-phenylethyl)oxiraneacetamide. This compound could also be designated as

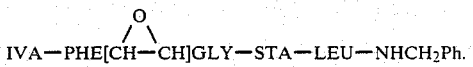

Calcd. for $C_{38}H_{56}N_4O_6.0.1CHCl_3$ (MW 676.80): C, 67.61; H, 8.36; N, 8.28. Found: C, 67.43; H, 7.89; N, 8.14.

The structure was also confirmed by NMR and MS spectroscopy. The stereochemistry at the epoxide is unknown.

EXAMPLE 11

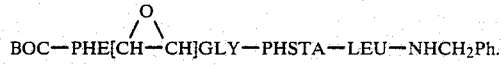

A solution of 180 mg (0.258 mmole) of BOC-PHE[CH=CH]GLY-PHSTA-LEU-NHCH₂Ph, in 10 ml of dichloromethane was treated with 88.9 mg (0.516 mmole) of m-chloroperbenzoic acid for two days at room temperature. The solution was diluted with dichloromethane and washed with 10% Na₂SO₃, 1N HCl, saturated NaHCO₃ and saturated NaCl. The solution was dried and the solvent was removed under reduced pressure to give 0.15 g (81.5%) of a whitish semi-solid,

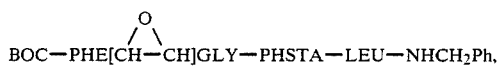

[1-[3-[2-[2-hydroxy-4[[3-methyl-1-[[(phenylmethyl)amino]carbonyl]butyl]amino]-4-oxo-1-(phenylmethyl)butyl]amino]-2-oxoethyl]oxyinanyl]-2-phenylethyl]carbamic acid-1,1-dimethyl ester.

Calcd. for $C_{41}H_{54}N_4O_7 \cdot 0.7CH_2Cl_2$ (MW 774.33): C, 64.68; H, 7.21; N, 7.24. Found: C, 64.61; H, 7.50; N, 7.25.

EXAMPLE 12

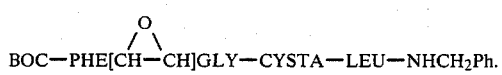

A solution of 450 mg (0.638 mmole) of BOC-PHE[CH=CH]GLY-CYSTA-LEU-NHCH$_2$Ph in 20 ml of CH$_2$Cl$_2$ was treated with 256 mg (1.27 mmole) of m-chloroperbenzoic acid. After 2 days, the solution was diluted with dichloromethane and washed with 10% Na$_2$SO$_3$, 1N HCl, saturated NaHCO$_3$ and saturated NaCl. The solution was dried and the solvent was removed under reduced pressure to afford 0.42 g of a foam. The foam was chromatographed over silica gel eluting with chloroform-methanol (97/3). The appropriate fractions were combined to give 0.290 g (63.04%) of

[1-[3-[2-[[1-(cyclohexylmethyl)-2-hydroxy-4-[[3-methyl-1-[[(phenylmethyl)amino]carbonyl]butyl]-amino]-4-oxobutyl]amino]-2-oxoethyl]oxiranyl]-2-phenylethyl]carbamic acid, 1,1-dimethylethyl ester, as an oil.

Calcd. for $C_{41}H_{60}N_4O_7 \cdot 0.7CHCl_3$ (MW 804.49): C, 62.25; H, 7.61; N, 6.96. Found: C, 61.94; H, 7.64; N, 6.90.

EXAMPLE 13

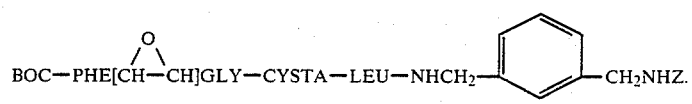

A solution of 480 mg (0.55 mmole) of

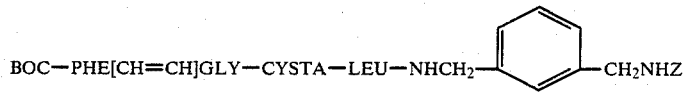

in 20 ml of dichloromethane was treated with 240 mg (1.1 mmole) of m-chloroperbenzoic acid for 2 days. The solution was diluted with dichloromethane and washed with 10% Na$_2$SO$_3$, 1N HCl, saturated NaHCO$_3$, saturated NaCl and dried. The solvent was removed under reduced pressure to afford 0.40 g (81.79%) of

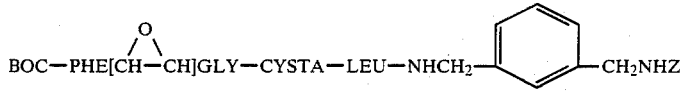

as a foam.

Calcd. for $C_{50}H_{69}N_5O_9 \cdot 0.25CH_2Cl_2$ (MW 905.32): C, 66.35; H, 7.70; N, 7.69. Found: C, 66.36; H, 7.52; N, 7.38.

EXAMPLE 14

A solution of 310 mg (0.35 mmole) of

in methanol was treated with a spatula tip of 10% Pd/C and placed under a hydrogen atmosphere. The reaction was followed by TLC. When the reaction was complete, the solution was filtered on Celite and the solvent was removed under reduced pressure to give 0.31 g (100%) of

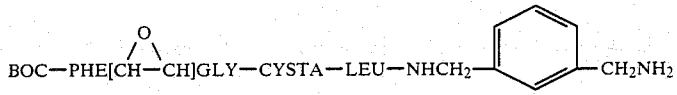

Calcd. for C₄₂H₆₃N₅O₇.0.9CHCl₃ (MW 857.41): C, 60.09; H, 7.51; N, 8.16. Found: C, 59.73; H, 7.51; N, 8.06.

EXAMPLE 15

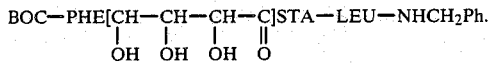

A solution of 620 mg (0.91 mmole) of

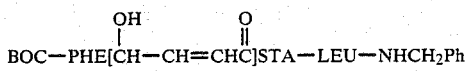

in 20 ml of tetrahydrofuran was treated with 12 ml (0.94 mmole) of a solution of 1 g osmium tetroxide in 50 ml of dioxane and allowed to stir at room temperature for 4 days. The dark solution was then treated with hydrogen sulfide gas and filtered. Removal of the solvent under reduced pressure gave 660 mg of crude product. After chromatography on silica gel, eluting with CHCl₃—CH₃OH (19/1) there was obtained 430 mg of pure product, 5,6-dideoxy-5-[[(1,1-dimethylethoxy)carbonyl]amino]-N-[2-hydroxy-4-[[3-methyl-1-[[(phenylmethyl)amino]carbonyl]butyl]amino]-1-(2-methylpropyl)-4-oxobutyl]-6-phenylhexonamide. This compound could also be designated as BOC—PHE[CH—CH—CH—C]STA—LEU—NHCH₂Ph.
        |   |   |   ||
        OH  OH  OH  O Calcd. for C₃₈H₅₈N₄O₉.0.25CHCl₃ (MW 744.72): C, 61.68; H, 7.88; N, 7.52. Found: C, 61.81; H, 7.92; N, 7.43.

The structure was also confirmed by NMR and MS spectroscopy. The stereochemistry at the vicinal hydroxyls is unknown.

EXAMPLE 16

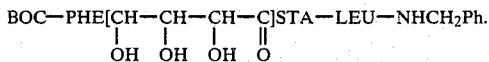

A solution of 500 mg (0.75 mmole) of BOC-PHE[CH=CH]GLY-STA-LEU-NHCH₂Ph in 10 ml of dioxane was treated with 11 ml (0.9 mmole) of a 2% solution of osmium tetroxide in dioxane and allowed to stir at room temperature for 3 days. The dark solution was then saturated with H₂S gas and filtered. After removal of the solvent under reduced pressure, the residue was chromatographed on silica gel, eluting with CHCl₃—MeOH (19/1). There was obtained 280 mg of pure product, 2,5,6-trideoxy-5-[[(1,1-dimethylethoxy)carbonyl]amino]-N-[2-hydroxy-4-[[3-methyl-1-[[(phenylmethyl)amino]carbonyl]butyl]amino]-1-(2-methylpropyl)-4-oxobutyl]-6-phenylhexonamide. This compound could also be designated as BOC—PHE[CH—CH]GLY—STA—LEU—NHCH₂Ph.
        |   |
        OH  OH Calcd. for C₃₈H₅₈N₄O₈.0.3CHCl₃ (MW 734.69): C, 62.61; H, 8.00; N, 7.64. Found: C, 62.68; H, 8.10; N, 7.31.

The structure was also confirmed by NMR and MS spectroscopy. The stereochemistry at the vicinal hydroxyls is unknown.

EXAMPLE 17

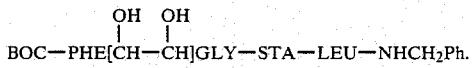

A solution of 600 mg (1.92 mmole) of [S-(E)]-5-[[(1,1-dimethylethoxy)carbonyl]amino]-6-cyclohexyl-3-hexenoic acid, 798 mg (1.92 mmole) of HCL.STA-LEU-NHCH₂Ph and 261 mg (1.92 mmole) of hydroxybenzotriazole in 20 ml of N,N-dimethylformamide was cooled in ice and treated with 0.27 ml (1.92 mmole) of triethylamine followed by a solution of 398 mg (1.92 mmole) of N,N'-dicyclohexylcarbodiimide in 5 ml of N,N-dimethylformamide. After stirring at 0° for 0.5 hour, the solution was allowed to stir at room temperature overnight. The solvent was then removed under reduced pressure and the residue taken up in ethyl acetate. The precipitated N,N'-dicyclohexylurea was filtered off and the filtrate extracted with 1N HCl, water, saturated NaHCO₃, then saturated NaCl. Drying over MgSO₄ and removal of the solvent under reduced pressure left 1.37 g of crude product. After chromatography on silica gel, eluting with CHCl₃—CH₃OH (32/1) there was obtained 840 mg of product, [4S-(4R*,8R*,9R*,13E,15R*)]-15-(cyclohexylmethyl)-8-hydroxy-4,9-bis(2-methylpropyl)-3,6,11-trioxo-1-phenyl-2,5,10,16-tetraaza-13-heptadecen-17-oic acid, 1,1-dimethylethyl ester. The compound could also be designated as BOC-CYCLOHEXYLALA[CH=CH]GLY-STA-LEU-NHCH₂Ph.

Calcd. for C₃₈H₆₂N₄O₆ (MW 670.91): C, 68.02; H, 9.32; N, 8.35. Found: C, 68.05; H, 9.34; N, 8.48.

The structure was confirmed by NMR and MS spectroscopy.

A solution of 320 mg (0.477 mmole) of BOC-CYCLOHEXYLALA[CH=CH]GLY-STA-LEU-NHCH₂Ph in 10 ml dioxane was treated with 7.5 ml (0.572 mmole) of a 2% solution of osmium tetroxide in dioxane. After stirring at room temperature for 3 days, the dark solution was treated with hydrogen sulfide gas and filtered. The solvent was removed under reduced pressure leaving 330 mg of a dark oil. After chromatography on silica gel, eluting with CHCl₃—CH₃OH (32/1) there was obtained 220 mg of product, 15-(cyclohexylmethyl)-8,13,14-trihydroxy-4,9-bis(2-methylpropyl)-3,6,11-trioxo-1-phenyl-2,5,10,16-tetraazaheptadecan-17-oic acid, 1,1-dimethylethyl ester. The compound could also be designated as

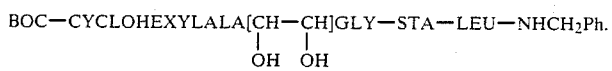

Calcd. for C$_{38}$H$_{64}$N$_4$O$_8$·0.25CHCl$_3$ (MW 734.77): C, 62.52; H, 8.81; N, 7.63. Found: C, 62.55; H, 8.88; N, 7.71.

The structure was also confirmed by NMR and MS spectroscopy. The stereochemistry of the vicinal hydroxyls is not known.

EXAMPLE 18

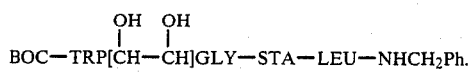

A solution of 570 mg (0.81 mmole) of BOC-TRP[CH=CH]GLY-STA-LEU-NHCH$_2$Ph in 16 ml of dioxane was treated with 14 ml (0.97 mmole) of a 2% solution of osmium tetroxide in dioxane. After stirring at room temperature for 3 days, the dark solution was treated with hydrogen sulfide gas and filtered. The solvent was removed under reduced pressure leaving 520 mg of crude product. After chromatography on silica gel, eluting with chloroform-methanol (19/1) there was obtained 260 mg of product, 8,13,14-trihydroxy-15-(1H-indol-3-ylmethyl)-4,9-bis-(2-methylpropyl)-3,6,11-trioxo-1-phenyl-2,5,10,16-tetraazaheptadecan-17-oic acid, 1,1-dimethylethyl ester. The compound also be designated as

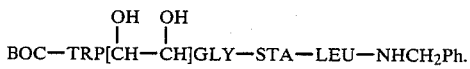

Calcd. for C$_{40}$H$_{59}$N$_5$O$_8$·0.35CHCl$_3$ (MW 779.70): C, 62.15; H, 7.67; N, 8.98. Found: C, 62.03; H, 7.64; N, 8.74.

The structure was confirmed by NMR and MS spectroscopy.

EXAMPLE 19

A solution of 323 mg (1.0 mmole) of (E)-N-[(tert-butyloxy)carbonyl]-5-amino-4-hydroxy-6-phenylhex-2-enoic acid, [J. Org. Chem. 50, 5399 (1985)], 416 mg (1.0 mmole) of HCl.STA-LEU-NHCH$_2$Ph, and 136 mg (1.0 mmole) of hydroxybenzotriazole in 15 ml of N,N-dimethylformamide was cooled in ice and 0.14 ml (1.0 mmole) of triethylamine added followed by a solution of 210 mg (1.0 mmole) of N,N'-dicyclohexylcarbodiimide in 5 ml of N,N-dimethylformamide. The solution was kept at 0° for 0.5 hour, then at room temperature overnight. The solvent was removed under pressure and the residue taken up in ethyl acetate. The precipitated N,N'-dicyclohexylurea was filtered off and the filtrate was washed with 1N HCl, saturated NaHCO$_3$, then saturated NaCl. Drying over MgSO$_4$ and removal of the solvent under reduced pressure gave 630 mg of crude product. After chromatography on silica gel, eluting with CHCl$_3$—CH$_3$OH (19/1) there was obtained 360 mg of a white solid. Recrystallization from CH$_3$OH/H$_2$O gave 325 mg of pure product, mp 207°–210°. The compound was named (E)-8,14-dihydroxy-4,9-bis(2-methylpropyl)-3,6,11-trioxo-1-phenyl-15-(phenylmethyl)-2,5,10,16-tetraazaheptadec-12-en-17-oic acid, 1,1-dimethylethyl ester. The compound could also be designated as

Calcd. for C$_{38}$H$_{56}$N$_4$O$_7$ (MW 680.86): C, 67.03; H, 8.29; N, 8.23. Found: C, 67.09; H, 8.16; N, 7.93.

The structure was also confirmed by NMR and MS spectroscopy.

EXAMPLE 20

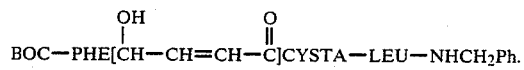

A solution of 134 mg (0.416 mmole) of (E)-N-[(tert-butyloxy)carbonyl]-5-amino-4-hydroxy-6-phenylhex-2-enoic acid, [J. Org. Chem. 50: 5399 (1985)], 189 mg (0.416 mmole) of CYSTA-LEU-NHCH$_2$Ph, hydrochloride and 56 mg (0.416 mmole) of hydroxybenzotriazole in 10 ml of N,N-dimethylformamide was cooled to 0° and 0.058 ml (0.416 mmole) of triethylamine was added. After 10 minutes a solution of 86 mg (0.416 mmole) of N,N'-dicyclohexylcarbodiimide in 5 ml of N,N-dimethylformamide was added, the solution was kept at 0° for one hour and then allowed to warm to room temperature overnight. The solvent was removed under reduced pressure and the residue was dissolved in ethyl acetate. The precipitated N,N'-dicyclohexylurea was filtered off and the organic solution was washed with 1N HCl, saturated NaHCO$_3$ and saturated NaCl. After drying, the solvent was removed under reduced pressure to yield 0.38 g of a solid. The solid was chromatographed on silica gel eluting with chloroform-methanol (97/3). The appropriate fractions were combined to afford 0.16 g (53.3%) of

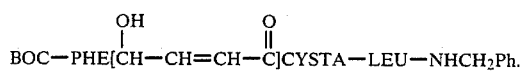

Calcd. for C$_{41}$H$_{60}$N$_4$O$_7$·0.25CHCl$_3$ (MW 750.77): C, 65.99; H, 8.09; N, 7.46. Found: C, 66.00; H, 7.89; N, 7.35.

EXAMPLE 21

A solution of 363 mg (1.1 mmole) of (E)-N-[(tert-butyloxy)carbonyl]-5-amino-4-hydroxy-6-phenylhex-2-enoic acid, 698 mg (1.1 mmole)

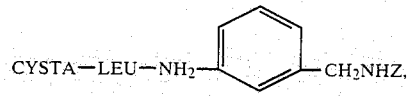

hydrochloride, and 133 mg (1.1 mmole) of hydroxybenzotriazole in 15 ml of N,N-dimethylformamide was cooled to 0° and 0.15 ml (1.1 mmole) of triethylamine was added. After ten minutes a solution of 233 mg (1.1 mmole) of N,N'-dicyclohexylcarbodiimide in 15 ml N,N-dimethylformamide was added, the solution was kept at 0° for an additional hour and then it was allowed to warm to room temperature overnight. The solvent was removed under reduced pressure and the residue was dissolved in ethyl acetate. The precipitated N,N'-dicyclohexylurea was filtered off and the organic solution was washed with 1N HCl, saturated NaHCO₃ and saturated NaCl. After drying the solvent was removed under reduced pressure to afford 0.65 g of a foam. The foam was chromatographed on silica gel, eluting with chloroform-methanol (97/3). The appropriate fractions were combined and concentrated to give 0.28 g (28%) of

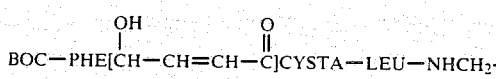

Calcd. for $C_{50}H_{69}N_5O_9 \cdot 0.45 CHCl_3$ (MW 937.82): C, 64.61; H, 7.46; N, 7.47. Found: C, 64.36; H, 7.28; N, 7.53.

EXAMPLE 22

A solution of 753 mg (1.1 mmole) of

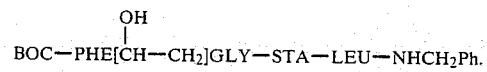

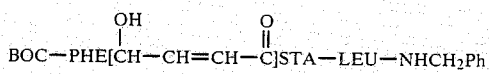

in 75 ml of methanol and containing a trace of Raney nickel as catalyst was reduced at 24°, 50 p.s.i. The material was filtered and the methanol removed under reduced pressure. Dichloromethane was added and the solvent removed under reduced pressure giving 694 mg of pure product, [4S-(4R*,8R*,9R*,15R*)]-8,14-dihydroxy-4,9-bis(2-methylpropyl)-3,6,11-trioxo-1-phenyl-15-(phenylmethyl)-2,5,10,16-tetraazaheptadecan-17-oic acid, 1,1-dimethylethyl ester. The compound could also be designated,

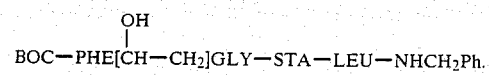

$[\alpha]_D^{23} = -35.1°$ (C, 0.92, CH₃OH).

Calcd. for $C_{38}H_{58}N_4O_7$ (MW 682.88): C, 66.83; H, 8.56; N, 8.21. Found: C, 66.57; H, 8.38; N, 8.14.

The structure was also confirmed by NMR and MS spectroscopy.

EXAMPLE 23

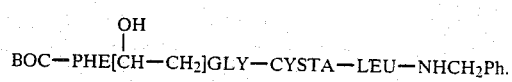

A solution of 100 mg (0.14 mmole) of

in 75 ml of methanol was treated with a trace of Raney-Ni and shaken under a hydrogen atmosphere. The solvent was removed under reduced pressure to give 0.12 g of an oil. After chromatography on silica gel, eluting with CHCl₃/MeOH (98/2) there was obtained 70 mg (70%) of the product.

Analysis Calcd.: C, 58.51; H, 7.35; N, 6.47. Found: C, 58.22; H, 7.49; N, 6.55.

EXAMPLE 24

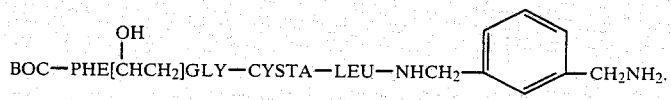

To a solution of 130 mg (0.147 mmole) of

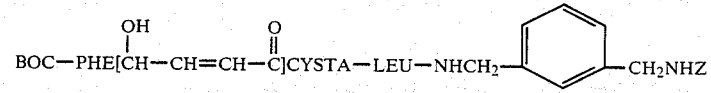

in 20 ml of methanol was added a spatula tip of 20% Pd/C and the solution was placed under a hydrogen atmosphere. The reaction was followed by TLC and after the appropriate time the mixture was filtered through Celite. The solvent was removed under reduced pressure to give 0.100 g (90%) of

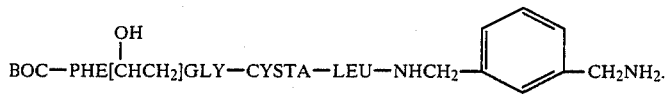

Calcd. for C₄₂H₆₅N₅O₇.0.5CHCl₃ (MW 811.67): C, 62.89; H, 8.15; N, 8.63. Found: C, 62.86; H, 8.03; N, 8.53.

EXAMPLE 25

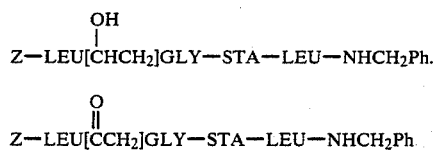

(0.1 g) was dissolved in ethanol and cooled to 0°. Sodium borohydride (0.05 g) was added and the mixture was stirred for three hours at 25°. Acetic acid and water 1:1 were added to the mixture. The mixture was taken up into ethyl acetate, washed with sodium bicarbonate, brine, and then dried over sodium sulfate. The solvent was filtered and evaporated. The residue was dissolved in dichloromethane, filtered and evaporated to give the product 0.1 g, 2,5,10,16-tetraazaheptadecan-17-oic acid, 8,14-dihydroxy-4,9,15-tris(2-methylpropyl)-3,6,11-trioxo-1-phenyl-, phenylmethyl ester; (4S,8S,9S,14R,S,15S). The compound could also be designated as Z—LEU[CHCH₂]GLY—STA—LEU—NHCH₂Ph.

Calcd. for C₃₈H₅₈N₄O₇.0.2CH₂Cl₂ (MW 699.86): C, 65.55; H, 8.41; N, 8.01. Found: C, 65.53; H, 6.36; N, 7.78.

EXAMPLE 26

Z—LEU[CCH₂]LEU—STA—LEU—NHCH₂Ph (with O double bond)

(0.15 g) was dissolved in ethanol (10 ml) and cooled to 0°. Sodium borohydride (0.02 g) was added and the mixture was allowed to warm to 25° and stir for two hours. Acetic acid and water 1:1 was added and the mixture was extracted with ethyl acetate and sodium bicarbonate. The organic phase was washed with brine, dried over sodium sulfate, filtered and evaporated. The residue was eluted on silica gel with ethyl acetate to give 0.2 g, 2,5,10,16-tetraazaheptadecan-17-oic acid, 8,14-dihydroxy-4,9,12,15-tetrakis(2-methylpropyl)-3,6,11-trioxo-1-phenyl-, phenylmethyl ester; (centers at 4, 9, 15 are L; centers at 12, 14 are unknown). This compound could also be designated as Z—LEU[CHCH₂]LEU—STA—LEU—NHCH₂Ph.

Calcd. for C₄₂H₆₆N₄O₇.0.2CH₂Cl₂ (MW 755.97): C, 67.04; H, 8.85; N, 7.41. Found: C, 67.34; H, 8.92; N, 7.26.

EXAMPLE 27

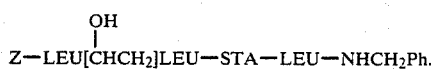

(0.5 g) was dissolved in 80% acetic acid/water (20 ml) and heated on a steam bath for 5 minutes. The mixture was allowed to slowly cool to 25°. The solvent was exaporated and the residue was extracted with chloroform and sodium carbonate. The organic layer was washed with brine, dried with sodium sulfate, filtered and evaporated. The residue was eluted from silica gel with chloroform then 10% methanol/ethyl acetate to give 0.3 g of the desired material, L-histidinamide,N-(3-methyl-1-oxobutyl)-L-phenylalanyl-N-[1-(cyclohexylmethyl)-2-hydroxy-5-oxo-5-[(phenylmethyl)amino]pentyl]; (center 1 is S; center 2 is R,S). This compound could also be designated as

Calcd. for C₃₉H₅₄N₆O₅.2H₂O (MW 722.90): C, 64.79; H, 8.09; N, 11.63. Found: C, 64.46; H, 7.72; N, 11.63.

EXAMPLE 28

(0.4 g) was dissolved in 80% acetic acid/water and heated on a steam bath for 5 minutes. The mixture was allowed to slowly cool to 25°. The solvent was evaporated and the residue was extracted with ethyl acetate and sodium carbonate. The organic layer was washed with brine, dried over sodium sulfate, filtered and evaporated. The residue was eluted from silica gel with chloroform and then 10% methanol/ethyl acetate to give 0.3 g of product, L-histidinamide,N-(3-methyl-1-oxobutyl)-L-phenylalanyl-N-L-1-(cyclohexylmethyl)-2-hydroxy-5-oxo-5-[[1-[[(phenylmethyl)amine]carbonyl]-3-methylbutyl]amino]pentyl] (center 1 is S; center 2 is R,S). This compound could also be designated as

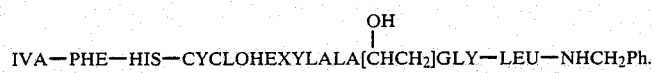

Calcd. for $C_{45}H_{65}N_7O_6.2.5H_2O$ (MW 845.07): C, 63.95; H, 8.35; N, 11.60. Found: C, 63.83; H, 7.96; N, 11.55.

EXAMPLE 29

Z-PHE[CHOHCH2]PHE-STA-LEU-NHCH2Ph 1.05 g Z-PHE[COCH2]PHE-STA-LEU-NHCH2Ph was dissolved in 10 ml absolute ethanol, to which was charged 0.3 g sodium borohydride. After stirring at 25° for two hours, glacial acetic acid was added until pH reached 5.0. The mixture was filtered, the solid washed with methanol and dried in vacuo, giving 0.50 g of the first isomer.

The second isomer was obtained by stripping the filtrate to a solid, 1.15 g, which was triturated with ethyl acetate. The suspension was filtered, and a solid was precipitated from the filtrate by addition of hexane. This solid was filtered, washed with hexane and dried in vacuo to a white solid, 0.26 g, similar to the first isomer by spectroscopic and chromatographic analyses. Both the first and second isomers were recombined and spectral and elemental analyses verified the mixture to be Z-PHE[CHOHCH2]PHE-STA-LEU-NHCH2Ph. $[\alpha]_D^{23} = -20.3°$ (C, 1.06, MeOH).

EXAMPLE 30

BOC-PHE[CHOHCH2]HIS-STA-LEU-NHCH2Ph 1.04 g of BOC-PHE[CHOHCH2]HIS(TRT)-STA-LEU-NHCH2Ph, slow isomer, was dissolved in 35 ml 80% glacial acetic acid, heated on the steam bath for 15 minutes and allowed to cool to 25° over one hour. The solution was stripped and the residue taken up in water. The pH was adjusted to 9.0 with 1N NaOH, extracted two times with ethyl acetate, the organic phase washed with saturated sodium chloride solution, and dried over anhydrous magnesium sulfate. The MgSO4 was filtered off, and a solid was precipitated from the filtrate by addition of ethyl ether. The solid was filtered, washed with ethyl ether and dried in vacuo to a white solid, 0.46 g, 58.5%. Another crop was obtained by concentrating the filtrate, 0.14 g, 18% yield. Both crops were combined and chromatographed on 15 g silica gel, eluting with a gradient from 1 to 5% methanol in chloroform. The fractions containing the product were combined, stripped to a residue and redissolved in ethyl acetate. The solution was precipitated by the addition of ethyl ether, filtered, and the solid was dried in vacuo to a white solid, 0.40 g, 51% yield. Spectral and elemental analyses confirmed the structure BOC-PHE[CHOHCH2]HIS-STA-LEU-NHCH2Ph, $[\alpha]_D^{23} = -43.5°$ (C, 1.1, MeOH).

EXAMPLE 31

BOC-PHE[CHOHCH2]HIS-STA-LEU-NHCH2Ph 0.90 g of BOC-PHE[CHOHCH2]HIS(TRT)-STA-LEU-NHCH2Ph, (fast isomer) was dissolved in 25 ml 80% acetic acid, heated by steam bath for three minutes, and allowed to cool to room temperature over two hours. The solution was stripped and water added, which was again stripped to an oil. The oil was dissolved in ethyl acetate and water, and the pH was adjusted to 9.0 with 1N NaOH. The organic phase was washed with saturated sodium chloride solution, dried over anhydrous magnesium sulfate, filtered, and stripped to a foam. The foam was chromatographed on 15 g silica gel, eluting with a gradient of 1.5 to 5% methanol in chloroform. The fractions containing the desired product were combined and stripped to a foam, dissolved in ethyl acetate, and precipitated as a solid in three crops by addition of ethyl ether. The solid was filtered, washed with ethyl ether and dried in vacuo to a white solid, 0.37 g, 54% yield. Spectral and elemental analyses confirm the structure as BOC-PHE[CHOHCH2]HIS-STA-LEU-NHCH2Ph, $[\alpha]_D^{\approx} = -14.3°$ (C, 1.13, MeOH).

EXAMPLE 32

To a 4.5 ml methanolic solution containing 166 mg of

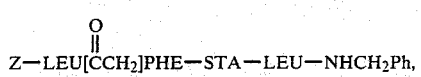

fast isomer, 93.7 mg of isovaleric anhydride, and 26.3 mg of isovaleric acid (99%), was added 19.4 mg of 20% palladium on barium sulfate which had been reduced with hydrogen in methanol. The mixture was hydrogenated for 115 min, then filtered through Celite and washed with methanol, and the filtrate and washing were allowed to stand at room temperature for 1.5 days and evaporated to dryness. The residue was chromatographed over 2.0 g of silica gel, and the product was eluted with 2% methanol in chloroform. Evaporation and drying in high vacuum gave 153.5 mg of product, mp 188°–192°. The structure was confirmed by elemental analyses and FAB mass spectrum.

EXAMPLE 33

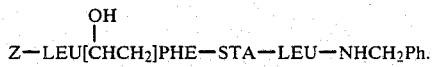

A solution of

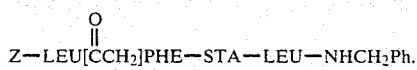

fast isomer, in 5 ml of tetrahydrofuran and 6.4 ml of ethanol was stirred at 0°, and 22.4 mg of sodium borohydride was added. After 1 day at 0°, 169 mg of glacial acetic acid was added dropwise with stirring in an ice bath, and the solution was evaporated in vacuo and dried in high vacuum to a solid. The solid was partitioned between 15 ml of chloroform and 0.7 ml of water. The chloroform layer was washed with saturated sodium chloride, dried with anhydrous sodium sulfate, and evaporated to 238 mg of a foam. The foam was chromatographed over 1.14 g of silica gel and eluted with chloroform containing up to 2% methanol, to give, after evaporation and drying in high vacuum, 225 mg of product. The structure of the product was confirmed by elemental analyses and physical data.

EXAMPLE 34

A solution of 852 mg of

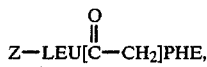

286 mg of hydroxybenzotriazole monohydrate, and 857 mg of STA-LEU-NHCH2Ph.HCl in 12 ml N,N-dimethylformamide was stirred in an ice bath, and 216 mg of triethylamine in 4 ml of N,N-dimethylformamide was added dropwise. The solution became cloudy after 15-20 min, and 441 mg of N,N'-dicyclohexylcarbodiimide was added. The reaction mixture was stirred at 0° for about one hour, then allowed to warm up gradually to room temperature. After 3.5 days the mixture was evaporated in vacuo to 3.08 g of syrup. A solution of the syrup in chloroform was washed with 1M citric acid, saturated sodium chloride solution, saturated sodium bicarbonate, then saturated sodium chloride. Drying over sodium sulfate and evaporating the solvent in vacuo gave 2.17 g of residue. The residue was chromatographed over 22 g of silica gel. Elution with CHCl3 and CHCl3—EtOAc (3/1) separated the product into a fact and a slow moving diastereomer. The structures of both components were confirmed by elemental analyses and spectral data. The fast isomer showed mp 67°-75°, and $[\alpha]_D^{23} = -23.5°$ (C, 1.0, methanol). The slow isomer showed up 65°-70°, and $[\alpha]_D^{23} = -51.5°$ (C, 1.1, methanol).

EXAMPLE 35

BOC-PHE[CH2CH2]GLY-STA-LEU-NHCH2Ph

A solution of 400 mg (0.97 mmole) of HCl.STA-LEU-NHCH2Ph, 297 mg (0.97 mmole) of BOC-PHE[CH2CH2]GLY and 131 mg (0.97 mmole) of hydroxybenzotriazole in 25 ml of N,N-dimethylformamide was cooled in ice and treated with 0.14 ml (0.97 mmole) of triethylamine followed by a solution of 202 mg (0.97 mmole) of N,N'-dicyclohexylcarbodiimide in 5 ml of N,N-dimethylformamide. After one hour at 0°, the mixture was allowed to stir at room temperature overnight. The solvent was then removed under reduced pressure and the residue taken up in ethyl acetate. The N,N'-dicyclohexylurea was filtered off, and the filtrate washed with 1N HCl, saturated NaHCO3, H2O, and saturated NaCl. Drying over MgSO4 and removal of the solvent under reduced pressure gave 600 mg of crude product as a foam. After chromatography on silica gel, eluting with CHCl3—MeOH (32/1), there was obtained 420 mg of pure product, [4S-(4R*,8R*,9R*,15R*)]-8-hydroxy-4,9-bis(2-methylpropyl)-3,6,11-trioxo-1-phenyl-15-(phenylmethyl)-2,5,10,16-tetraazaheptadecan-17-oic acid, 1,1-dimethylethyl ester. This compound could also be designated as BOC-PHE[CH2CH2]GLY-STA-LEU-NHCH2Ph.

Calcd. for C38H58N4O6.0.2CHCl3 (MW 690.75): C, 66.42; H, 8.49; N, 8.11. Found: C, 66.75; H, 8.47; N, 7.73. $[\alpha]_D^{23} = -23.4°$ (C, 0.93, CH3OH).

The structure was also confirmed by NMR and MS spectroscopy.

EXAMPLE 36

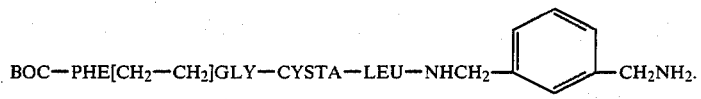

A solution of 150 mg (0.17 mmole) of

in 20 ml of methanol was treated with a spatula tip of 10% Pd/C and placed under a hydrogen atmosphere. The reaction was monitored by TLC and continued until complete. After filtering through Celite the solvent was removed under reduced pressure to afford 0.14 g (100%) of

Calcd. for C42H65N5O6.0.6CHCl3 (MW 807.61): C, 63.35; H, 8.19; N, 8.67. Found: C, 63.49; H, 8.49; N, 8.69.

EXAMPLE 37

IVA-PHE[CH₂s]PHE-STA-ALA-STA-NHCH₂Ph

A mixture of 0.49 g of IVA-PHE[CH₂S]PHE, 0.68 g of STA-ALA-STA-NHCH₂Ph, 0.17 g of hydroxybenzotriazole, and 0.5 ml of triethylamine in 80 ml of a 5/3 mixture of CH₂Cl₂/DMF was cooled to 0° and treated with 0.27 g of N,N'-dicyclohexylcarbodiimide. After stirring at 0° for 1 h, the mixture was allowed to warm to room temperature overnight. The solvent was removed under reduced pressure and the residue taken up in CH₂Cl₂. After filtering off the N,N'-dicyclohexylurea, the solution was washed with 10% Na₂CO₃, then saturated NaCl. After drying over MgSO₄, concentration of the filtrate gave crude product. Chromatography on silica gel, eluting with CH₂Cl₂/CH₃OH (19/1) gave 0.63 g (59%) of the product, N-[ 2-hydroxy-4-[[2-[[2-hydroxy-1-(2-methylpropyl)-4- -oxo-4-[(phenylmethyl)amino]butyl]amino]-1-methyl-2- oxoethyl]amino]-1-(2-methylpropyl)-4-oxobutyl]-α-[[2- [(3-methyl-1-oxobutyl)amino]-3-phenylpropyl]thio]-, phenylpropanamide.

EXAMPLE 38

IVA-PHE[CH₂SO₂]PHE-STA-ALA-STA-NHCH₂Ph

A solution of 0.4 g IVA-PHE[CH₂S]PHE-STA-ALA-STA-NHCH₂Ph in 50 ml CHCl₃ was treated with 0.4 g of m-chloroperbenzoic acid and stirred at room temperature overnight. The mixture was diluted with CHCl₃ and washed two times with 10% NaHSO₃, then twice with 10% Na₂CO₃. After drying over MgSO₄, the filtrate was concentrated to give the crude product. Chromatography on silica gel, eluting with CH₂Cl₂—MeOH (95/5) gave 0.18 g (44%) of the product, 13,21-dihydroxy-2,17-dimethyl-12,20-bis(2-methylpropyl)-4,10,15,18-tetraoxo-N,6,9-tris(phenylmethyl)-8-thia-5,11,16,19-tetraazatricosan-23-amide-8,8-dioxide.

EXAMPLE 39

IVA-PHE[CH₂S]PHE-STA-LEU-NHCH₂Ph

A mixture of 0.66 g IVA-PHE[CH₂S]PHE, 0.68 g STA-LEU-NHCH₂Ph.HCl, and 0.22 g of hydroxybenzotriazole in CH₂Cl₂—DMF (1/1) was cooled in ice and treated with 0.23 ml of triethylamine followed by 0.34 g of N,N'-dicyclohexylcarbodiimide. The mixture was then allowed to stir at room temperature for 2 days. The solvent was removed under reduced pressure and the residue taken up in ethyl acetate. The precipitated N,N'-dicyclohexylurea was filtered off and the filtrate washed with 10% Na₂CO₃, 1N citric acid, then saturated NaCl. After drying over MgSO₄ and removal of the solvent under reduced pressure, the residue was chromatographed on silica gel using CH₂Cl₂ then CH₂Cl₂—MeOH (9/1) as the eluant. Combining the appropriate fractions gave 0.19 g of the product, 6-hydroxy-17-methyl-2,7-bis(2-methylpropyl)-4,9,15-trioxo-N,10,13-tris(phenylmethyl)-11-thia-3,8,14-triazaoctadecanamide.

EXAMPLE 40

IVA-PHE[CH₂SO]PHE-STA-ALA-STA-NHCH₂Ph

A mixture of 0.27 g of IVA-PHE[CH₂SO]PHE, 0.47 g of STA-ALA-STA-NHCH₂Ph.CF₃CO₂H, and 0.09 g of 1-hydroxybenzotriazole in 40 ml of a 5/3 CH₂Cl₂/DMF solution was cooled in ice and treated with 0.3 ml of triethylamine. A solution of 0.13 g of N,N'-dicyclohexylcarbodiimide in 5 ml of DMF was then added and mixture allowed to stir at room temperature overnight. The solvent was removed under reduced pressure and the residue taken up in ethyl acetate. The precipitated N,N'-dicyclohexylurea was filtered off and the filtrate washed with 1N citric acid, 10% Na₂CO₃, then saturated NaCl. Drying over MgSO₄ and concentrating the filtrate under reduced pressure gave the crude product. Chromatography on silica gel, eluting with CH₂Cl₂—MeOH (97/3) gave 0.24 g of the product, 13,21-dihydroxy-2,17-dimethyl-12,20-bis(2-methylpropyl)-4,10,15,18-tetraoxo-N,6,9-tris(phenylmethyl)-8-thia-5,11,16,19-tetraazatricosan-23-amide-8-oxide.

EXAMPLE 41

BOC-PHE[CH₂SO₂]PHE-STA-ALA-STA-NHCH₂Ph

A solution of 0.3 g BOC-PHE[CH₂S]PHE-STA-ALA-STA-NHCH₂Ph in 15 ml of CH₂Cl₂ was treated with 0.42 g of m-chloroperbenzoic acid and allowed to stir at room temperature for 3 days. The solution was then diluted with CH₂Cl₂ and washed with 10% NaHSO₃, then 10% Na₂CO₃. Drying over MgSO₄ and removing the solvent under reduced pressure gave a foam. After chromatography on silica gel, eluting with CH₂Cl₂—MeOH (95/5), there was obtained 0.25 g of 10,18-dihydroxy-14-methyl-9,17-bis(2-methylpropyl)-7,12,15,20-tetraoxo-22-phenyl-3,6-bis(2-methylpropyl)-7,12,15,20-tetraoxo-22-phenyl-3,6-bis(phenylmethyl)-5-thia-2,8,13,15,21-pentaazadocosanoic acid-1,1-dimethylethyl ester-5,5-dioxide.

EXAMPLE 42

BOC-PHE[CH₂SO]PHE-STA-ALA-STA-NHCH₂Ph

A solution of 0.35 g BOC-PHE[CH₂SO]PHE, 0.59 g STA-ALA-STA-NHCH₂Ph.CF₃CO₂H, and 0.11 g 1-hydroxybenzotriazole in 50 ml of 1:1 CH₂Cl₂/DMF was cooled in ice and treated with 0.25 ml of triethylamine. 0.17 g of N,N'-dicyclohexylcarbodiimide was then added and the mixture allowed to warm to room temperature overnight. The solvent was removed under reduced pressure and the residue taken up in ethyl acetate. The precipitated N,N'-dicyclohexylurea was filtered off and the filtrate extracted with 10% Na₂CO₃, 1N citric acid, then saturated NaCl. After drying over MgSO₄ and removal of the solvent under reduced pressure, there was obtained crude product. Chromatography on silica gel, eluting with CH₂Cl₂—MeOH (98/2) gave 0.66 g (89%) of 10,18-dihydroxy-14-methyl-9,17-bis(2-methylpropyl)-7,12,15-20-tetraoxo-22-phenyl-3,6-bis(phenylmethyl)-5-thia-2,8,13,16,21-pentaazadocosanoic acid-1,1-dimethyl ester-5-oxide.

EXAMPLE 43

BOC-PHE[CH₂SO]PHE-STA-LEU-NHCH₂Ph

A solution of 0.31 g of BOC-PHE[CH₂SO]PHE, 0.3 g STA-LEU-NHCH₂Ph.HCl, and 0.1 g 1-hydroxybenzotriazole in 50 ml of 1:1 CH₂Cl₂/DMF was cooled in ice and treated with 0.1 ml of triethylamine. 0.18 g of N,N'-dicyclohexylcarbodiimide was then added and the solution allowed to warm to room temperature for 2 days. The solvent was then removed under reduced pressure and the residue taken up in ethyl acetate. The precipitated N,N'-dicyclohexylurea was filtered off and the filtrate worked with 1N citric acid, then 10% Na₂CO₃. Drying over MgSO₄ and removing the solvent under reduced pressure gave crude product. After chromatography on silica gel, eluting with CH₂Cl₂—MeOH (98/2) there was obtained 0.35 g (61.6%) of 10-hydroxy-9,14-bis(2-methylpropyl)-7,12,15-trioxo-17-phenyl-3,6-bis(phenylmethyl)-5-thia-2,8,13,16-tetraazaheptadecanoic acid-1,1-dimethyl ethyl ester-5-oxide. Dissolving this solid in ethyl acetate and diluting with hexane gave 0.32 g of the product as a white solid.

EXAMPLE 44

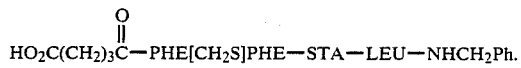

A solution of 0.49 of

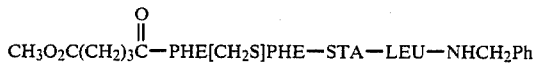

in 10 ml of MeOH was treated with 1.2 ml of 1N NaOH and allowed to stir at room temperature for 3 days. The solvent was removed under reduced pressure and the residue taken up in ethyl acetate. This was washed with 1N citric acid, dried over MgSO₄ 1, and the solvent removed under reduced pressure to give the crude product. This was dissolved in ethyl acetate and diluted with hexane. There was obtained 0.32 g (66%) of the product, 8-hydroxy-4,9-bis(2-methylpropyl)-3,6,11,17-tetraoxo-1-phenyl-12,15-bis(phenylmethyl)-13-thia-2,5,10,16-tetraazaheneicosan-21-oic acid.

EXAMPLE 45

IVA-PHE[CH₂S]GLY-STA-LEU-NHCH₂Ph

A solution of 0.5 g IVA-PHE[CH₂S]GLY, 0.66 g STA-LEU-NHCH₂Ph.HCl, and 0.22 g of 1-hydroxybenzotriazole in 100 ml of 1:1 CH₂Cl₂/DMF was cooled in ice and treated with 0.22 ml of triethylamine. 0.33 g of N,N'-dicyclohexylcarbodiimide was added and the solution allowed to warm to room temperature overnight. The solvent was removed under reduced pressure and the residue taken up in ethyl acetate. The precipitated N,N'-dicyclohexylurea was filtered off and the filtrate washed with 10% Na₂CO₃, 1N citric acid, then dried over MgSO₄. Removal of the solvent under reduced pressure and chromatography of the residue on silica gel, eluting with CH₂Cl₂—MeOH (98/2) gave 1.07 g (94%) of the product, 6-hydroxy-17-methyl-2,7-bis(2-methylpropyl)-4,9,15-trioxo-N, 13-bis(phenylmethyl)-11-thia-3,8,14-triazaoctadecamide.

EXAMPLE 46

A solution of 0.39 g

0.5 g STA-LEU-NHCH₂Ph.HCl, and 0.16 g 1-hydroxybenzotriazole in 50 ml of 1:1 CH₂Cl₂/DMF was cooled in ice and treated with 0.2 ml of triethylamine. 0.25 g of N,N'-dicyclohexylcarbodiimide was then added and the solution allowed to stir at room temperature for 2 days. The solvent was removed under reduced pressure and the residue taken up in ethyl acetate. The precipitated N,N'-dicyclohexylurea was filtered off and the filtrate washed with 1N citric acid, then 10% Na₂CO₃. Drying over MgSO₄ and removal of the solvent under reduced pressure gave the crude product. Chromatography on silica gel, eluting with CH₂Cl₂—MeOH (97/3) gave 0.35 g (43%) of product, 8-hydroxy-4,9-bis(2-methylpropyl)-3,6,11,14-tetraoxo-1-phenyl-15(phenylmethyl)-2,5,10,-16-tetraazaheptadecan-17-oic acid-1,1-dimethylethyl ester.

EXAMPLE 47

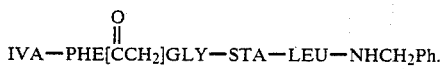

A solution of 0.49 g

0.66 g STA-LEU-NHCH₂Ph.HCl, and 0.22 g of 1-hydroxybenzotriazole in 75 ml of 1:1 CH₂Cl₂/DMF was cooled in ice and treated with 0.3 ml of triethylamine. 0.33 g of N,N'-dicyclohexylcarbodiimide was then added and the solution allowed to stir at room temperature for 2 days. The solvent was removed under reduced pressure and the residue taken up in ethyl acetate. The precipitated N,N'-dicyclohexylurea was filtered off and the filtrate washed with 1N citric acid, then 10% Na₂CO₃. After drying over MgSO₄ and concentrating the filtrate under reduced pressure, the residue was chromatographed on silica gel, eluting with CH₂Cl₂—MeOH (98/2). There was obtained 0.64 g (60%) of the product, N-[2-hydroxy-4-[[3-methyl-1-[[(phenylmethyl)amino]carbonyl]butyl]amino]-1-(2-methylpropyl)-4-oxobutyl]-δ-[(3-methyl-1-oxobutyl)amino]benzenehexanamide. [α]$_D^{23}$ −21.5° (C, 0.55, MeOH).

EXAMPLE 48

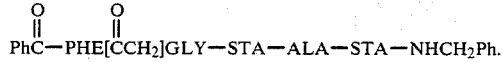

A solution of 0.27 g

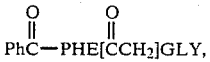

0.5 g STA-ALA-STA-NHCH₂Ph, and 0.11 g of 1-hydroxybenzotriazole in 50 ml of 5:3 CH₂Cl₂/DMF was cooled in ice and treated with 0.2 ml of triethylamine. 0.17 g of N,N'-dicyclohexylcarbodiimide was then added and the solution allowed to stir at room temperature overnight. The solvent was removed under reduced pressure and the residue taken up in CH₂Cl₂. The precipitated N,N'-dicyclohexylurea was filtered off and the residue washed with 10% Na₂CO₃, then 1N citric acid. Drying over MgSO₄, concentrating the filtrate under reduced pressure, and chromatography of the residue on silica gel, eluting with CH₂Cl₂—MeOH (97/3) gave 0.48 g (73%) of the product, 10,18-dihydroxy-14-methyl-9,17-bis(2-methylpropyl)-1,4,7,12,15-pentaoxo-1-phenyl-N, 3-bis(phenylmethyl)-2,8,13,16-tetraazaeicosan-20-amine. [α]$_D^{23}$ = −36.5° (C, 0.57, MeOH).

EXAMPLE 49

Z-PHE[COCH₂]PHE-STA-LEU-NHCH₂Ph 0.78 g of Z-PHE[COCH₂]PHE and 0.25 g 1-hydroxybenzotriazole monohydrate were dissolved in 50 ml methylene chloride and cooled to −5°. A solution of 0.38 g N,N'-dicyclohexylcarbodiimide in 5 ml ethylene chloride was added, followed by a suspension of 0.72 g STA-LEU-NHCH₂Ph.HCl in 10 ml methylene chloride with 0.27 ml triethylamine. The mixture was allowed to slowly warm to 25° while stirring overnight.

The precipitated N,N'-dicyclohexylurea was filtered off, and the solvent removed under reduced pressure. The residue was dissolved in ethyl acetate and washed with 1N citric acid, saturated sodium chloride solution, saturated sodium bicarbonate and saturated sodium chloride solution. The solution was dried over anhydrous magnesium sulfate, filtered and stripped to a foam, 1.42 g. The residue was chromatographed on 90 g silica gel, eluted with 1% methanol in chloroform, and the fractions containing the less polar of the two isomers were combined. Trituration with ethyl ether gave 0.38 g (27%) of product. Spectral and elemental analyses verify the structure as Z-PHE[COCH₂]PHE-STA-LEU-NHCH₂Ph. $[\alpha]_D^{23} = -20.1°$ (C, 1.06, MeOH).

EXAMPLE 50

BOC-PHE[COCH₂]GLY-STA-ALA-STA-NHCH₂Ph

Triethylamine, 73 mg (0.72 mmole), was added to STA-ALA-STA-NHCH₂Ph.TFA, 0.44 g (0.72 mmole) in 25 ml of N,N-dimethylformamide at 0°-5°. This suspension was then added to a mixture of BOC-PHE[COCH₂]GLY, 0.23 g (0.72 mmole) and 1-hydroxybenzotriazole, 0.11 g (0.72 mmole) in 25 ml of N,N-dimethylformamide. This mixture was cooled in ice and 0.149 g (0.72 mmole) of N,N'-dicyclohexylcarbodiimide was added. The mixture was refrigerated overnight, filtered, and the solvent evaporated in vacuo. The residue was taken up in dichloromethane and extracted successively with 10% Na₂CO₃, 10% citric acid, and saturated NaCl. The dichloromethane layer was dried over sodium sulfate, then evaporated in vacuo and the residue purified by chromatography over 200 g of silica gel and eluting with dichloromethane-methanol (95:5) to give 5,13-dihydroxy-9-methyl-6,14-bis(2-methylpropyl)-3,8,11,16,19-pentaoxo-1-phenyl-20-(phenylmethyl)-2,7,10,15,21-pentaazadocosan-22-oic acid, 1,1-dimethylethyl ester; (5S,7S,13S,14S,20RS), 0.3 g, $[\alpha]_D^{25} = -43.7°$ C, 0.27, MeOH).

Calcd. for C₄₃H₆₅N₅O₉.H₂O (MW 814.0): C, 63.44; H, 8.30; N, 8.60. Found: C, 63.67; H, 8.00; H, 8.55.

EXAMPLE 51

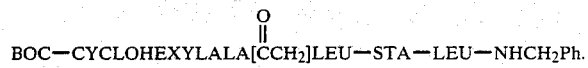

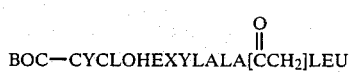

(0.4 g), STA-LEU-NHCH₂Ph.HCl (0.43 g), triethylamine (0.15 ml), and hydroxybenzotriazole (0.14 g) were stirred together in N,N-dimethylformamide (20 ml). The mixture was cooled to 0° and N,N'-dicyclohexylcarbodiimide (0.22 g) was added. The mixture was allowed to slowly warm to 25° and stir for 24 hours. The mixture was filtered and the filtrate was extracted with ethyl acetate and water. The organic phase was washed with water, sodium bicarbonate, and brine. The extract was dried over sodium sulfate, filtered and evaporated. The residue was chromatographed on silica gel eluting with 1:1 ethyl acetate/hexane to give 0.68 g of product. This compound could also be designated as

Calcd. for C₄₂H₇₀N₄O₇ (MW 743.01): C, 67.89; H, 9.50; N, 7.54. Found: C, 67.66; H, 9.32; N, 7.81.

EXAMPLE 52

IVA-VAL[CH₂NH]VAL-STA-ALA-STA-NHCH₂Ph

To a cold solution of 7.2 g (0.043 mole) VAL-OCH₃.HCl in toluene was added 6.0 ml (0.043 mole) of Et₃N. This was added to a solution of 7.9 g (0.043 mole) isovalerylvalinal in toluene containing activated 3 Å molecular sieves. The mixture was stirred at room temperature for 5½ hours then cooled to 5°. MeOH was added followed by 1.8 g (0.047 mole) NaBH₄ and the reaction was stirred in an ice bath. After 25 minutes the mixture was filtered. Citric acid solution was added to the filtrate and the organic solvents were evaporated. The aqueous residue was extracted twice with ethyl acetate. The organic phase was washed with Na₂CO₃ solution and then saline and dried with MgSO₄. The drying agent was removed by filtration and the filtrate was evaporated to give 11.9 g (92%) of a clear colorless oil as product, (S)-N-[3-methyl-2-[(3-methyl-1-oxobutyl)amino]butyl]-L-valine, methyl ester. This compound can also be designated as IVA-VAL[CH₂NH]VAL-OCH₃.

Calcd. for C₁₆H₃₂N₂O₃ (MW 300.43): C, 63.96; H, 10.74; N, 9.32. Found: C, 63.95; H, 10.08; N, 9.23.

To 11.3 g (0.0376 mole) of IVA-VAL[CH₂NH]VAL-OMe in THF was added an aqueous solution of 9.4 g (0.113 mole) NaHCO₃ followed by 7.0 g (0.0413 mole) of benzylchloroformate. The reaction was stirred at room temperature overnight. The THF was evaporated and the aqueous residue extracted with ether. The organic phase was washed with citric acid solution and then salt solution and dried with MgSO₄. The drying agent was filtered and the filtrate was evaporated to give 14.6 g (89.6%) of a colorless oil. The compound is designated as IVA-VAL[CH₂NZ]VAL-OCH₃.

Calcd. for C₂₄H₃₈N₂O₅ (MW 434.56): C, 66.33; H, 8.81; N, 6.44. Found: C, 66.39; H, 8.53; N, 5.98.

14.5 g (0.033 mole) of IVA-VAL[CH₂NZ]VAL-OMe was dissolved in methanol and cooled in an ice bath. To this solution was added 36 ml (0.072 mole) of 2N NaOH and the reaction stirred for 3 days at 5°, then overnight at room temperature. After neutralization with 36 ml 2N HCl, the methanol was evaporated. The aqueous residue was extracted twice with ethyl acetate. The organic phases were combined, washed with citric acid solution, NaCl solution and dried with MgSO$_4$. The drying agent was filtered and the filtrate concentrated to produce 14.5 g of an oil. The product is designated as IVA-VAL[CH$_2$NZ]VAL.

Calcd. for C$_{23}$H$_{36}$N$_2$O$_5$.0.5H$_2$O (MW 429.52): C, 64.31; H, 8.68; N, 6.52. Found: C, 64.45; H, 8.55; N, 6.21.

To a solution of 0.37 g (0.87 mmole) IVA-VAL[CH$_2$NZ]VAL in CH$_2$Cl$_2$ and DMF was added 0.13 g (0.87 mmole) of 1-hydroxybenzotriazole followed by 0.2 g (0.96 mmole) of N,N'-dicyclohexylcarbodiimide.

In a separate flask, a solution of 0.5 g (0.87 mmole) of STA-ALA-STA-NHCH$_2$Ph.HCl in CH$_2$Cl$_2$/DMF was cooled in an ice bath and 0.22 ml (1.6 mmole) of triethylamine added. The two solutions were then combined and left at room temperature overnight. The solvent was removed under reduced pressure and the residue taken up in ethyl acetate. The precipitated N,N'-dicyclohexylurea was filtered off, and the filtrate washed with citric acid solution, Na$_2$CO$_3$ solution, then saline. The organic phase was dried over MgSO$_4$ and concentrated to give 0.7 of crude product. Chromatography on silica gel gave 230 g of pure product, designated as IVA-VAL[CH$_2$NZ]VAL-STA-ALA-STA-NHCH$_2$Ph.

0.20 g (0.22 mmole) of IVA-VAL[CH$_2$NZ]VAL-STA-ATA-STA-NHCH$_2$Ph was dissolved in 100 ml of methanol and 5 ml acetic acid. 20% Pd/C was added and the system was flushed with N$_2$. Hydrogen was bubbled into the mixture at room temperature for one hour. The system was again flushed with N$_2$, the catalyst filtered and the filtrate concentrated. Methylene chloride was added to the residue and the solution was evaporated. This process was repeated a few times. The residue was triturated in ether/petroleum ether to produce 140 mg of product, 5,8,11,16,19-pentaazatricosan-23-amide, 13,2-dihydroxy-2,17-dimethyl-6,9-bis(1-methylethyl)-12,20-bis(2-methylpropyl)-4,10,15,18-tetraoxo-N-(phenylmethyl)-,:6S-(6R*,9R*,12R*,13R*,17R*,20R*,21R*):-,acetate (salt) (2:3). The product can also be designated IVA-VAL[CH$_2$NH]VAL-STA-ALA-STA-NHCH$_2$Ph.

Calcd. for C$_{41}$H$_{72}$N$_6$O$_7$.1.5CH$_3$COOH (MW 851.11): C, 62.09; H, 9.24; H, 9.87. Found: C, 62.03; H, 9.26; N, 9.90.

EXAMPLE 53

IVA-VAL[CH$_2$NH]VAL-STA-OEt 1.1 g (0.0036 mole) of BOC-STA-OEt was treated with 50% trifluoroacetic acid/CH$_2$Cl$_2$ for 15 minutes. The reaction was evaporated, CH$_2$Cl$_2$ added and the solution concentrated again. This process was repeated a few times to remove the trifluoroacetic acid. The residue was then dissolved in CH$_2$Cl$_2$, cooled in an ice bath and 0.50 ml (0.0036 mole) of Et$_3$N was added. In a separate flask a solution of 1.5 g (0.0036 mole) of IVA-VAL[CH$_2$NZ]VAL and 0.56 g (0.0036 mole) of 1-hydroxybenzotriazole in CH$_2$Cl$_2$ and DMF was treated with 0.80 g (0.0039 mole) of N,N'-dicyclohexylcarbodiimide. The solution of STA-OEt was then added and the reaction stirred overnight at room temperature. The reaction was concentrated and the residue taken up in ethyl acetate and filtered. The ethyl acetate solution was washed with citric acid solution, Na$_2$CO$_3$ solution and saline, and dried with MgSO$_4$. After filtering, the solvent was removed to render 2.1 g of an oily product, designated as IVA-VAL[CH$_2$NZ]VAL-STA-OEt.

1.7 g (0.0028 mole) of IVA-VAL[CH$_2$NZ]VAL-STA-OEt was hydrogenated for 6.5 hours in 100 ml acetic acid with 0.4 g 20% Pd/C. After filtration of the reaction the filtrate was concentrated. Na$_2$CO$_3$ solution was added and the product was extracted into ethyl acetate. The organic phase was isolated and washed with saline solution. The ethyl acetate solution was evaporated to give a white solid which was washed with ether, 0.48 g. Heptanoic acid, 3-hydroxy-6-methyl-4-[[3-methyl-2-[[3-methyl-2-[(3-methyl-1-oxobutyl)amino]butyl]amino]-1-oxobutyl]amino]-, ethyl ester, [3S-[3R*,- 4R*[R*[R*[(R*)]]]]-. The product can also be designated as IVA-VAL[CH$_2$NH]VAL-STA-OEt.

Calcd. for C$_{25}$H$_{49}$N$_3$O$_5$ (MW 471.67): C, 63.66; H, 10.47; N, 8.91. Found: C, 64.04; H, 10.76; N, 8.90.

EXAMPLE 54

IVA-VAL[CH$_2$NH]VAL-STA-NHCH$_2$Ph

To a solution of 0.80 g (0.0019 mole) of IVA-VAL[CH$_2$NZ]VAL in CH$_2$Cl$_2$/DMF was added 0.29 g (0.0019 mole) of 1-hydroxybenzotriazole hydrate followed by 0.43 g (0.0021 mole) of N,N'-dicyclohexylcarbodiimide. To the resulting solution was added 0.45 g (0.0017 mole) of STA-NHCH$_2$Ph. The reaction was stirred at room temperature overnight, filtered, and the filtrate concentrated. The residue was taken up in CHCl$_3$ and filtered. The filtrate was chromatographed to give 0.44 g of product, IVA-VAL[CH$_2$NZ]VAL-STA-NHCH$_2$Ph.

To a solution of 0.195 g (0.00029 mole) of IVA-VAL[CH$_2$NZ]VAL-STA-NHCH$_2$Ph in 100 ml methanol and 5 ml of acetic acid was added 20% Pd/C. The system was purged with N$_2$ and hydrogen was bubbled in at room temperature for one hour. The system was again purged with N$_2$. The catalyst was filtered and the filtrate concentrated. The residue was triturated with hexane and the solid was crystallized from ethyl acetate to give IVA-VAL[CH$_2$NH]VAL-STA-NHCH$_2$Ph.

Calcd. for C$_{30}$H$_{52}$N$_4$O$_4$ (MW 532.75): C, 67.63; H, 9.84; N, 10.52. Found: C, 67.30; H, 9.84; N, 10.09.

EXAMPLE 55

IVA-VAL[CH$_2$NH]VAL-STA-LEU-NHCH$_2$Ph

To a solution of 0.5 g (0.0012 mole) of IVA-VAL[CH$_2$NZ]VAL in CH$_2$Cl$_2$/DMF was added 0.18 g (0.0012 mole) of 1-hydroxybenzotriazole hydrate followed by 0.27 g (0.0013 mole) of N,N'-dicyclohexylcarbodiimide. In a separate flask 0.5 g (0.0012 mole) of STA-LEU-NHCH$_2$Ph.HCl was taken up in CH$_2$Cl$_2$/DMF and treated with 0.17 ml (0.0012 mole) Et$_3$N. This was then added to the IVA-VAL[CH$_2$NZ]-VAL solution and stirred at room temperature overnight. The reaction was concentrated and the residue taken up in ethyl acetate and filtered. The filtrate was washed with citric acid solution, Na$_2$CO$_3$ solution and saline solution and dried with MgSO$_4$. After filtration the solvent was removed and the crude product was chromatographed to give 0.54 g of product, designated as IVA-VAL[CH$_2$NZ]-VAL-STA-LEU-NHCH$_2$Ph.

Calcd. for C$_{44}$H$_{69}$N$_5$O$_7$ (MW 780.32): C, 67.75; H, 8.92; N, 8.98. Found: C, 67.33; H, 8.91; N, 8.82.

To a solution of 0.35 g (0.45 mmole) of IVA-VAL[CH$_2$NZ]VAL-STA-LEU-NHCH$_2$Ph in 100 ml methanol and 5 ml acetic acid was added 20% Pd/C. The system was purged with $N_2$. Hydrogen was bubbled in for 40 minutes. The system was again purged with $N_2$. The catalyst was filtered and the filtrate was concentrated. The residue was retreated as above with $H_2$ and 20% Pd/C. After filtering the catalyst and concentrating the filtrate, the resulting residue was triturated in ether/petroleum ether. The solid obtained was crystallized from ether to give 180 mg of product, 3,8,11,14-tetraazaoctadecanamide, 6-hydroxy-17-methyl-10,13-bis(1-methylethyl)-2,7-bis(2-methylpropyl)-4,9,15-trioxo-N-(phenylmethyl)-,[2S-(2R*,-6R*,7R*,10R*,13R*)]-, acetate (salt) (5:1). The product can also be designated as IVA-VAL[CH$_2$NH]VAL-STA-LEU-NHCH$_2$Ph.

Calcd. for $C_{36}H_{63}N_5O_5.0.2CH_3CO_2H$ (MW 657.91): C, 66.45; H, 9.78; N, 10.64. Found: C, 66.13; H, 9.73; N, 10.61.

EXAMPLE 56

BOC-PHE-VAL-STA-LEU[CH$_2$NZ]CH$_2$Ph

To a solution of 2.9 g (0.0146 mole) of BOC-leucinal in CHCl$_3$ was added 3A molecular sieves followed by 1.6 g (0.0146 mole) of benzylamine. The reaction was stirred at room temperature for one hour and then cooled in an ice bath. 0.55 g (0.0146 mole) of NaBH$_4$ was added followed by methanol and the reaction was stirred in the ice bath for 0.5 hour. After filtration, citric acid solution was added to the filtrate and this was then concentrated. The resulting aqueous residue was extracted with ethyl acetate which in turn was washed with Na$_2$CO$_3$ solution and then saline solution. The organic phase was dried with MgSO$_4$. After filtering off the drying agent the filtrate was concentrated to 3.1 g of an oil. After chromatography 3.0 g of product was obtained. It can be designated as BOC-LEU[CH$_2$NH]CH$_2$Ph.

Calcd. for $C_{18}H_{30}N_2O_2.0.05CHCl_3$ (MW 312.40): C, 69.39; H, 9.70; N, 8.96. Found: C, 69.33; H, 9.77; N, 8.76.

2.9 g (0.0095 mole) of BOC-LEU[CH$_2$NH]CH$_2$Ph, 1.8 g (0.0105 mole) benzylchloroformate and 2.4 g (0.0285 mole) of Na$_2$CO$_3$ were stirred in THF/H$_2$O overnight at room temperature. The THF was evaporated and the aqueous residue was extracted with ethyl acetate. The organic phase was washed with citric acid solution and then NaCl solution and dried with MgSO$_4$. After the drying agent was filtered the filtrate was evaporated to give 4.2 g of a yellow oil, BOC-LEU[CH$_2$NZ]CH$_2$Ph.

4.0 g (0.0091 mole) of BOC-LEU[CH$_2$NZ]CH$_2$Ph was dissolved in Ch$_2$Cl$_2$ and cooled. Trifluoroacetic acid was added and the solution was stirred at room temperature for 25 minutes. The reaction was concentrated, CH$_2$Cl$_2$ added and the solution concentrated again. This was repeated several times to give 4.8 g of an oil, designated as LEU[CH$_2$NZ]CH$_2$Ph.

2.6 g (0.0057 mole) of LEU[CH$_2$NZ]CH$_2$Ph.2.1 CF$_3$COOH was dissolved in CH$_2$Cl$_2$ and cooled in an ice bath. Et$_3$N was added until basic. This was then added to a solution of 1.0 g (0.0057 mole) BOC-STA, 0.87 g (0.0057 mole) 1-hydroxybenzotriazole hydrate, and 1.3 g (0.0063 mole) N,N'-dicyclohexylcarbodiimide in CH$_2$Cl$_2$/DMF. The reaction was stirred at room temperature for 3 days and then filtered. The filtrate was concentrated and the residue was taken up in ethyl acetate. This solution was washed with citric acid solution, Na$_2$CO$_3$ solution and NaCl solution. The ethyl acetate phase was dried with MgSO$_4$ which was then filtered off and the filtrate concentrated. After chromatography, there was obtained 3.1 g of the product designated as BOC-STA-LEU[CH$_2$NZ]CH$_2$Ph.

2.9 g (0.0048 mole) of BOC-STA-LEU[CH$_2$NZ]CH$_2$Ph was treated with trifluoroacetic acid/CH$_2$Cl$_2$ (1:1) at room temperature for 0.5 hour. The solution was evaporated. This was repeated several times. The residue was then dissolved in CH$_2$Cl$_2$ and cooled in an ice bath. In a separate flask a solution of 1.0 g (0.0046 mole) of BOC-VAL in CH$_2$Cl$_2$/DMF was treated with 0.74 g (0.0048 mole) of 1-hydroxybenzotriazole hydrate followed by 1.1 g (0.0053 mole) of N,N'-dicyclohexylcarbodiimide. To the cooled STA-LEU[CH$_2$NZ]CH$_2$Ph.TFA solution was added DMF and Et$_3$N until basic. This was then added to the BOC-VAL solution. The reaction was stirred at room temperature overnight and then filtered. The filtrate was concentrated, taken up in ethyl acetate and filtered. The ethyl acetate solution was washed with citric acid solution, Na$_2$CO$_3$ solution and NaCl solution. The organic phase was dried with MgSO$_4$, which was then removed by filtration. Upon concentrating the filtrate, the product began to crystallize. Petroleum ether was added and 2.0 g of a white solid was obtained. It can be designated as BOC-VAL-STA-LEU[CH$_2$NZ]CH$_2$Ph.

0.6 g (0.86 mole) of BOC-VAL-STA-LEU[CH$_2$NZ]CH$_2$Ph was treated with 50% trifluoroacetic acid/CH$_2$Cl$_2$ for 0.5 hour at room temperature. The reaction was concentrated, CH$_2$Cl$_2$ l added and the solution stripped again. This was repeated. The residue was then dissolved in CH$_2$Cl$_2$ and cooled in an ice bath. In a separate flask a solution of 0.23 g. (0.86 mmole) of BOC-PHE in CH$_2$Cl$_2$/DMF was treated with 0.13 g of 1-hydroxybenzotriazole followed by 0.20 g (0.95 mmole) of N,N'-dicyclohexylcarbodiimide. To the cooled VAL-STA-LEU[CH$_2$NZ]CH$_2$Ph.CF$_3$COOH solution was added Et$_3$N until basic. This was then added to the BOC-PHE solution. The reaction was stirred at room temperature for 3 days and then filtered. The filtrate was evaporated, the residue taken up in ethyl acetate and filtered. The organic solution was washed with citric acid solution, aqueous Na$_2$CO$_3$ and saline solution and dried with MgSO$_4$. After filtration, the filtrate was concentrated and petroleum ether added to the residue. The product was obtained as a solid. 1-valinamide.N-[(1,1-dimethylethoxy)carbonyl]-L-phenylalanyl-N-[2-hydroxy-4-[[3-methyl-1-[[[(phenylmethoxy)carbonyl](-phenylmethyl)amino]methyl]butyl]amino]-1-(2-methylpropyl)-4-oxobutyl]-, [2S-[1R*,2R*,4R*)]]-. It can also be designated as BOC-PHE-VAL-STA-LEU[CH$_2$NZ]CH$_2$Ph.

EXAMPLE 57

IVA-PHE-HIS-STA-LEU[CH$_2$NZ]CH$_2$Ph 1.6 g (3.6 mmole) of BOC-STA-LEU[CH$_2$NZ]CH$_2$Ph was treated with 50% trifluoroacetic acid/CH$_2$Cl$_2$ at room temperature for 0.5 hour. The reaction was evaporated, CH$_2$Cl$_2$ added and the solution concentrated again. This was repeated. The residue was then dissolved in CH$_2$Cl$_2$ and cooled in an ice bath. In a separate flask a solution of 1.8 g (3.6 mmole) of BOC-HIS(TRT) in DMF/Ch$_2$Cl$_2$ was treated with 0.55 g (3.6 mmole) of 1-hydroxybenzotriazole followed by 0.82 g (3.6 mmole) of N,N'-dicyclohexylcarbodiimide. To the cooled STA-LEU[CH$_2$NZ]CH$_2$Ph. trifluoroacetic acid solution was added Et$_3$N until basic. This was then added to the BOC-HIS(TRT) solution. The reaction was stirred overnight at room temperature and then filtered. The filtrate was evaporated, ethyl acetate was added and the mixture filtered. The ethyl acetate filtrate was washed with aqueous citric acid, $Na_2CO_3$ solution and saline and dried with $MgSO_4$. After filtering the drying agent the filtrate was concentrated and the residue chromatographed to produce 1.1 g of product, designated as BOC-HIS(TRT)-STA-LEU[CH$_2$NZ]CH$_2$Ph.

Calcd. for $C_{59}H_{72}N_6O_7$ (MW 977.21): C, 72.51; H, 7.43; N, 8.60. Found: C, 72.35; H, 7.40; N, 8.74.

0.4 g (0.41 mmole) of BOC-HIS(TRT)-STA-LEU[CH$_2$NZ]CH$_2$Ph was treated with 50% trifluoroacetic acid/CH$_2$Cl$_2$. The reaction was evaporated, solvent added, and the solution concentrated. This process was repeated. The residue was taken up in CH$_2$Cl$_2$ and cooled. In a separate flask a solution of 1.0 g (0.41 mmole) of IVA-PHE in DMF/CH$_2$Cl$_2$ was treated with 0.06 g (0.41 mmole) of 1-hydroxybenzotriazole followed by 0.08 g (0.41 mmole) of N,N'-dicyclohexyl carbodiimide. The cooled HIS-STA-LEU[CH$_2$NZ]CH$_2$Ph.trifluoroacetic acid solution was treated with Et$_3$N until basic. This was then added to the IVA-PHE solution and the reaction was stirred at room temperature overnight. The reaction was concentrated, filtered and taken up in ethyl acetate. The organic solution was washed with citric acid solution, NaCO$_3$ solution and saline and dried with MgSO$_4$. The drying agent was removed by filtration and the solvent was evaporated. After chromatography on silica gel 100 mg of product was obtained. L-histidinamide. N-(3-methyl-1-oxobutyl)-L-phenylalanyl-N-[2-hydroxy-4-[[3-methyl-1-[[[(phenylmethoxy)carbonyl](phenylmethyl)amino]methyl]butyl]amino]-1-(2-methylpropyl)-4-oxobutyl]-, [1S-[1R*,2R*,4(R*)]]-. It can also be designated as IVA-PHE-HIS-STA-LEU[CH$_2$NZ]CH$_2$Ph.

Calcd. for $C_{49}H_{67}N_7O_7.0.2CHCl_3$ (MW 899.96): C, 66.40; H, 7.61; N, 11.02. Found: C, 66.50; H, 7.42; N, 11.31.

EXAMPLE 58

IVA-PHE-HIS-STA-LEU[CH$_2$NH]CH$_2$Ph 0.255 g of material containing both IVA-PHE-HIS(TRT)-STA-LEU[CH$_2$NZ]CH$_2$Ph and IVA-PHE-HIS-STA-LEU[CH$_2$NZ]CH$_2$Ph was dissolved in trifluoroacetic acid and HBr was bubbled in for 0.5 hour. The reaction was stirred at room temperature for 40 minutes. The reaction was concentrated, CH$_2$Cl$_2$ added and the solution concentrated again. This was repeated several times. Ether was added and a light orange solid was obtained. After chromatography an off-white solid was obtained. This can be designated as IVA-PHE-HIS-STA-LEU[CH$_2$NH]CH$_2$Ph.

Calcd. for $C_{41}H_{61}N_7O_5.2HBr.0.5CHCl_3$ (MW 8.73.66): C, 52.28; H, 6.71; N, 10.28. Found: C, 52.94; H, 6.89; N, 9.89.

EXAMPLE 59

BOC-PHE[CH$_2$NH]PHE-STA-ALA-STA-NHCH$_2$Ph

To a solution of 4.5 g (0.021 mole) of PHE-OMe.HCl in 100 ml CH$_2$Cl$_2$ at 5° was added 100 ml of 2N Na$_2$CO$_3$ solution. The mixture was shaken, the CH$_2$Cl$_2$ layer separated, dried and evaporated to an oil. The oil was dissolved in 100 ml toluene-CH$_2$Cl$_2$ (3:1), 30 g. 3 Å molecular sieves were added and 5 g of BOC-PHE[CHO]. The mixture was stirred five hours at 25°, cooled in an ice bath and 800 mg of NaBH$_4$ in 25 ml MeOH added. The mixture was stirred 25 minutes at 10°. 2N citric acid solution was carefully added until acidic. The solution was filtered, evaporated and extracted with EtOAc. The EtOAc solution was dried and evaporated to an oil. The oil was purified over silica gel using EtOAc. A clear oil, 6 g was obtained. The product can be designated as BOC-PHE[CH$_2$NH]PHE-OCH$_3$.

Calcd. for $C_{24}H_{32}N_2O_4$ (MW 412.51): C, 69.88; H, 7.82; N, 6.79. Found: C, 69.77; H, 7.91; N, 6.72.

The above ester, 6 g (0.0145 mole) was dissolved in 75 ml of THF, 20 ml H$_2$O, stirred and the pH adjusted to 10 with 1N Na$_2$CO$_3$ solution. A 2.6 g (0.0153 mole) of benzylchloroformate was added. The pH was kept at 10 by addition of 1N Na$_2$CO$_3$ solution. After three hours the THF was evaporated in vacuo and the oily precipitate was extracted into EtOAc. The EtOAc solution was dried and evaporated to a light yellow oil, 7 g (87%); $[\alpha]_D^{25} = -58.3°$ (C, 1.0, MeOH). The product can be designated as BOC-PHE[CH$_2$NZ]PHE-OCH$_3$.

Calcd. for $C_{32}H_{38}N_2O_6$ (MW 546.64): C, 70.32; H, 7.01; N, 5.13. Found: C, 69.78; H, 7.22; N, 5.12.

The ester, 3 g (0.0255 mole), was dissolved in 25 ml of MeOH and 10 ml of 2N NaOH was added. The solution was kept 3 days at 4° with small amounts of H$_2$O (1-3 ml) being added every 12 hours. The solution was filtered and the filtrate was acidified with 2N citric acid. The oil which formed was extracted into EtOAc which was dried and evaporated to an oil, 2.7 g. The oil was purified over silica gel using EtOAc yielding 2 g (68%) of a yellow oil. The product can be designated as BOC-PHE[CH$_2$NZ]PHE.

Calcd. for $C_{31}H_{36}N_2O_6.0.5H_2O$ (MW 541.62): C, 68.74; H, 6.89; N, 5.17. Found: C, 68.82; H, 6.87; N, 5.07.

To a solution of 0.5 g (0.87 mmole) of STA-ALA-STA-NHCH$_2$Ph.HCl in 20 ml of DMF was added 0.23 ml of Et$_3$N. The solution was kept at 25° for 45 minutes and then 0.465 g (0.87 mmole) of BOC-PHE[CH$_2$NZ]-PHE, 0.137 g (0.87 mmole) of 1-hydroxybenzotriazole and 0.185 g (0.87 mmole) of N,N'-dicyclohexylcarbodiimide added. The mixture was kept at 25° for 24 hours. The mixture was filtered and the filtrate was evaporated in vacuo. The residue was dissolved in EtOAc. The EtOAc solution was washed with H$_2$O, 1N Na$_2$CO$_3$ solution, H$_2$O, 1N citric acid solution, dried and evaporated to 1.0 g of an oil. The oil was purified by chromatography over silica gel with CH$_3$CN giving 0.17 g of a foam. 0.15 g of the foam was dissolved in 100 ml MeOH, 0.1 g 20% Pd/C catalyst added and H$_2$ gas bubbled into the solution for one hour at a slow rate. The catalyst was removed and the filtrate evaporated affording 0.12 g of a white solid whose structure was confirmed by IR, NMR and MS. The product can be designated as BOC-PHE[CH$_2$NH]PHE-STA-ALA-STA-NHCH$_2$Ph.

EXAMPLE 60

BOC-PHE[CH$_2$NH]PHE-STA-LEU-NHCH$_2$Ph

To a solution of 0.5 g (0.0012 mole) of STA-LEU-NHCH$_2$Ph.HCl in 20 ml of DMF was added 0.2 ml of Et$_3$N. The solution was kept 20 minutes at 25° and 0.63 g (0.0012 mole) of BOC-PHE[CH$_2$NZ]PHE, 0.18 g (0.0012 mole) of 1-hydroxybenzotriazole and 0.25 g of (0.0012 mole) of N,N'-dicyclohexylcarbodiimide added. The mixture was kept 24 hours at 25°, filtered and evaporated. The residue was taken up in EtOAc, washed with H$_2$O, 1N citric acid, H$_2$O, 1N Na$_2$CO$_3$, dried, and evaporated to an oil. The oil was purified over silica gel using CHCl$_3$—MeOH (9:1). The product, 1 g, was an oil, BOC-PHE[CH$_2$NZ]PHE-STA-LEU-NHCH$_2$Ph.

Calcd. for C$_{52}$H$_{69}$N$_5$O$_8$ (MW 892.11): C, 70.00; H, 7.80; N, 7.85. Found: C, 69.70; H, 7.80; N, 7.70.

The above oil was dissolved in MeOH, 0.1 g 20% Pd/C added and H$_2$ gas bubbled through the solution for one hour at 25°. The catalyst was removed by filtration and the filtrate evaporated to a white solid, 0.5 g. The structure was confirmed by IR, NMR, MS. The product can be designated as BOC-PHE[CH$_2$NH]PHE-STA-LEU-NHCH$_2$Ph.

EXAMPLE 61

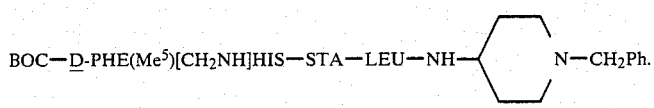

The pH of a solution of 5.5 g (0.019 mole) of D-PHE(Me$^5$)-OCH$_3$.HCl dissolved in 75 ml of H$_2$O and 100 ml of THF was adjusted to 10 with Na$_2$CO$_3$. 5 g (0.023 mole) of di-t-butyl dicarbonate was added and the solution was stirred two hours at 25°, pH 9-10. The pH was brought to 6.5 with citric acid and the mixture was diluted with ice water (100 ml). The solid was removed, washed with H$_2$O and dried, 8.3 g mp 127°-128°. The solid was dissolved in 125 ml warm EtOH and was added to a suspension of 4 g of NaBH$_4$ in 50 ml 75% EtOH-H$_2$O. The solution was refluxed for two hours, cooled and acidified with 50% citric acid solution. The EtOH was evaporated in vacuo and the white solid washed with H$_2$O and dried, 6 g. The product was purified over silica gel using CHCl$_3$—MeOH (9:1) giving a white solid, 5 g, (82%), mp 163°-165°. The product can be designated as BOC-D-PHE(-Me$^5$)[CH$_2$OH].

Calcd. for C$_{19}$H$_{31}$NO$_3$ (MW 321.45): C, 70.99; H, 9.72; N, 4.36. Found: C, 70.66; H, 9.67; N, 4.54.

The above alcohol 4.8 g (0.0149 mole) was dissolved in 25 ml of DMSO, stirred and cooled to 15°. 6.5 ml of triethylamine was added and then 7.5 g (0.0472 mole) of pyridine.SO$_3$ complex. The solution was stirred for 40 minutes at 25° and was diluted with 150 ml ice water. The solution was acidified with 2N citric acid. The solid which formed was removed, washed with H$_2$O and dried, 4 g, (84%), mp 133°-135°. The product can be designated as BOC-D-PHE(Me$^5$)[CHO].

Calcd. for C$_{19}$H$_{29}$NO$_3$ (MW 319.43): C, 71.44; H, 9.15; N, 4.39. Found: C, 70.85; H, 9.48; N, 4.38.

To a solution of 5 g (0.0135 mole) of

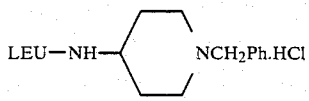

in 50 ml of DMF was added 3 ml of triethylamine. The solution was filtered, and 2.0 g (0.0135 mole) 1-hydroxybenzotriazole, and 2.9 g (0.0135 mole) of N,N'-dicyclohexylcarbodiimide, and 3.7 g (0.0135 mole) of BOC-STA was added to the filtrate. The solution was stirred overnight at 25°, evaporated to an oil, taken up in 100 ml EtOAc and the solution was washed with H$_2$O, dilute Na$_2$CO$_3$ solution, dried and evaporated to an oil, 10 g. The oil was dissolved in ether, filtered and evaporated, 8 g. The oil was dissolved in 100 ml of HOAc containing 5 g HCl gas. The solution was kept two hours at 25° and evaporated to an oil, 7.8 g. The product can be designated as

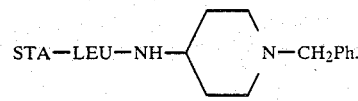

4.5 g (0.0084 mole) of the above compound was dissolved in 50 ml DMF, cooled to 5° and 2.5 ml Et$_3$N added followed by 1.3 g (0.0084 mole) of 1-hydroxybenzotriazole, 1.8 g (0.0084 mole) of N,N'-dicyclohexylcarbodiimide, and 4.2 g (0.0084 mole) of BOC-HIS(TRT). The solution was kept at 25° for 2 days. The solution was filtered and evaporated to a brown oil. The oil was purified over silica gel with CHCl$_3$—MeOH (9:1) giving 5 g of light tan foam, $[\alpha]_D^{25} = -18.0°$ (C, 1.0, MeOH). The product can be designated as

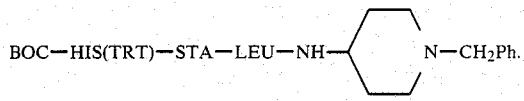

Calcd. for C$_{56}$H$_{73}$N$_7$O$_6$.2/3CHCl$_3$ (MW 1020.19): C, 66.74; H, 7.28; N, 9.61. Found: C, 66.34; H, 7.36; N, 10.00.

To a solution of 4.5 g (0.0048 mole) of above tripeptide was added 20 ml CH$_2$Cl$_2$ and 30 ml TFA. The solution was allowed to stand one hour at 25° and evaporated in vacuo to an oil. Ether afforded a white solid, 5 g. 2.5 g (0.0027 mole) of this white solid was dissolved in 30 ml EtOH and Et$_3$N added until pH 9-9.5 (2 ml). 0.850 g (0.0027 mole) of BOC-D-PHE-(Me$^5$)[CHO] was added and then 25 g of 3 Å molecular sieves (dried at 400°). The mixture was stirred one hour at 25°, the pH was adjusted to 7 with glacial HOAc and 0.2 g (0.0032 mole) of NaCNBH$_3$ was added. The solution was stirred 4 days at 25°. 2 g of solid citric acid was added, stirred one hour, filtered and the filtrate evaporated to an oil. The oil was taken up in 100 ml EtOAc, washed with H$_2$O, 1N Na$_2$CO$_3$ solution, dried and evaporated to a yellow gum, 1.3 g. The product was purified over silica gel using CHCl$_3$—MeOH (9:1) and yielded 300 mg of solid. The product can be designated as

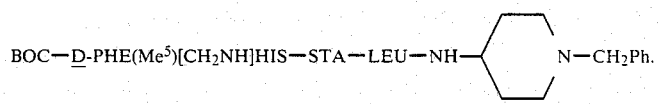

Cacld. for $C_{51}H_{82}N_8O_6.0.5CHCl_3$ (MW 962.92): C, 64.37; H, 8.60; N, 11.66. Found: C, 64.72; H, 8.68; N, 11.73.

EXAMPLE 62

BOC-PHE[CH$_2$NH]HIS(BOM)-STA-LEU-NHCH$_2$Ph

A solution of 4.1 g (0.0113 mole) of HIS(BOM)-OCH$_3$.HCl in 50 ml of EtOH was cooled in ice and 3.5 ml of Et$_3$N added. After 3–4 minutes 2.8 g (0.0113 mole) of BOC-PHE[CHO] was added along with 30 g 3 Å molecular sieves. The pH was adjusted to 5 with glacial HOAc and 0.85 g (0.013 mole) of NaCNBH$_3$ was added. The mixture was stirred 3 days at 25°. 5 g of citric acid was added, the mixture was stirred two hours, filtered and the filtrate evaporated. The residue was dissolved in EtOAc and the solution was washed with 1N citric acid, H$_2$O, 1N Na$_2$CO$_3$, dried and evaporated to an oil. The oil was purified over silica gel using CHCl$_3$—MeOH (95:5) yielding an oil, 4.5 g (76%). The product can be designated as BOC-PHE[CH$_2$NH]HIS(BOM)-OCH$_3$.

Calcd. for $C_{29}H_{38}N_4O_5.0.5CHCl_3$ (MW 582.32): C, 60.85; H, 6.66; N, 9.62. Found: C, 60.07; H, 6.45; N, 9.46.

9 g (0.0172 mole) of the above oil was dissolved in 50 ml THF and 10 ml H$_2$O and 3.5 g (0.021 mole) of benzylchloroformate was added. The pH was maintained at 8 with 2N Na$_2$CO$_3$ solution. The solution was stirred one hour at 25°, the THF evaporated and the oil extracted into EtOAc. The EtOAc was dried and evaporated to an oil, 10.5 g (93%). The product can be designated as BOC-PHE[CH$_2$NZ]HIS(BOM)-OCH$_3$.

Calcd. for $C_{37}H_{44}N_4O_7$ (MW 656.75): C, 67.76; H, 6.75; N, 8.53. Found: C, 68.17; H, 7.23; N, 8.07.

The above ester, 3 g (0.0046 mole), was dissolved in 25 ml of MeOH and 5 ml of 2N NaOH was added. The solution was kept one hour at 25° and was then diluted with 100 ml H$_2$O. The solution was acidified with solid citric acid to pH 3 and the white precipitate was filtered, washed with H$_2$O and dried, 3 g. The product can be designated as BOC-PHE[CH$_2$NZ]HIS(BOM).

Calcd. for $C_{37}H_{44}N_4O_7.H_2O$ (MW 674.77): C, 65.84; H, 6.89; N, 8.30. Found: C, 66.20; H, 6.90; N, 7.70.

To a solution of 0.50 g (0.0012 mole) of STA-LEU-NHCH$_2$Ph.HCl in 20 ml of DMF was added Et$_3$N until pH 9–9.5 (0.2 ml). 0.18 g (0.0012 mole) of 1-hydroxybenzotriazole was added, followed by 0.775 g (0.0012 mole) of BOC-PHE-[CH$_2$NZ]HIS(BOM), and 0.25 g (0.0012 mole) of N,N'-dicyclohexylcarbodiimide. The mixure was kept 18 hours at 25°. The mixture was filtered, the filtrate evaporated and the residue was taken up in EtOAc. The EtOAc solution was washed with H$_2$O, dried and evaporated. The residue was purified over silica gel using CHCl$_3$—MeOH (9:1) giving an off-white solid, 0.50 g. The above solid was dissolved in 100 ml MeOH, 0.3 g. 20% Pd/C catalyst added and H$_2$ gas bubbled into the solution for one hour. The solution was filtered, evaporated and the residue chromatographed over silica gel with CHCl$_3$—MeOH (9:1) to yield 0.40 g of product. The product can be designated as BOC-PHE[CH$_2$NH]HIS(BOM)-STA-LEU-NHCH$_2$Ph. The mass spectrum showed the molecular ion at a mass of 868.5.

EXAMPLE 63

BOC-PHE[CH$_2$NH]HIS-STA-ALA-STA-NHCH$_2$Ph

To a solution of 0.80 g (0.0014 mole) of STA-ALA-STA-NHCH$_2$Ph.HCl in 25 ml DMF was added 0.37 ml of Et$_3$N. The solution was kept 45 minutes at 25° and 0.9 g (0.0014 mole) BOC-PHE[CH$_2$NZ]HIS(BOM) was added, followed by 0.29 g (0.0014 mole) of N,N-dicyclohexylcarbodiimide and 0.185 g (0.0014 mole) of 1-hydroxybenzotriazole. The mixture was kept 24 hours at 25°, filtered and evaporated. The residue was purified over silica gel using CH$_3$CN to give an oil, 0.7 g. 0.50 g of the oil was dissolved in 50 ml MeOH. 0.1 g 20% Pd/C catalyst was added and the solution hydrogenated at 50 p.s.i. for 18 hours. The catalyst was removed and the filtrate evaporated. Addition of ether gave an off-white solid, 0.20 g. The solid was purified over silica gel using CHCl$_3$-MeOH (9:1) yielding 0.150 g white solid. The product can be designated as BOC-PHE[CH$_2$NH]-HIS-STA-ALA-STA-NHCH$_2$Ph.

Calcd. for $C_{46}H_{70}N_8O_8$ (MW 863.08): C, 64.01; H, 8.19; N, 12.98. FOund: C, 64.20; H, 7.92; N, 11.57.

EXAMPLE 64

BOC-PHE[CH$_2$NH]HIS-STA-LEU-NHCH$_2$Ph

BOC-PHE[CH$_2$NZ]HIS-STA-LEU-NHCH$_2$Ph (0.5 g) was dissolved in methanol (20 ml) and palladium on carbon (20%) (0.1 g) was added. The flask was evacuated and flushed with hydrogen. The mixture was stirred for two hours under hydrogen then was flushed with nitrogen. The mixture was filtered and the solvent was evaporated to give 0.4 g of product. 2,5,8,13,16-Pentaazaheptadecanoic acid, 10-hydroxy-6-(1H-imidazo-4-ylmethyl)-9,14-bis(2-methylpropyl)-7,12,15-trioxo-17-phenyl-3-(phenylmethyl)-, 1,1-dimethylethyl ester, [3S-(3R*,6R*,9R*,10R*,14R*)]-.

This compound could also be designated as BOC-PHE[CH$_2$NH]HIS-STA-LEU-NHCH$_2$Ph.

Calcd. for $C_{41}H_{61}N_7O.6.0.07CHCl_3$ (MW 756.31): C, 65.22; H, 8.17; N, 13.00. Found: C, 65.18; H, 7.91; N, 12.82.

EXAMPLE 65

IVA-PHE-HIS-LEU[CH$_2$NH]LEU-NHCH$_2$Ph

A solution of 0.4 g of IVA-PHE-HIS(TRT)LEU[CH$_2$NBOC]LEU-NHCH$_2$Ph in 4 ml of CH$_2$Cl$_2$ was treated with 4 ml of TFA and stirred at 25° for two hours. The solvent was evaporated and the residue taken up in 15 ml of 80% acetic acid and warmed on the steam bath for 5 minutes, then allowed to cool to room temperature over 0.5 hours. The solvent was removed under reduced pressure and the residue taken up in EtOAc and washed with saturated NaHCO$_3$, then saturated NaCl. After drying over Na$_2$SO$_4$ the solvent was removed under reduced pressure leaving the crude product. Chromatography on silica gel, eluting with EtOAc-MeOH (9/1) gave 0.2 g of pure product, L-histidinamide, N-(3-methyl-1-oxobutyl)-L-phenylalanyl-N-[3-methyl-1-[[[3-methyl-1-[[(phenylmethyl)amino]-carbonyl]butyl]amino]methyl]butyl], [S-(R*,R*)]. The compound can also be designated as IVA-PHE-HIS-LEU[CH$_2$NH]LEU-NHCH$_2$Ph.

Calcd. for $C_{39}H_{57}N_7O_4.0.3EtOAc$ (MW 714.33): C, 67.59; H, 8.38; N, 13.73. Found: C, 67.23; H, 8.22; N, 13.66.

EXAMPLE 66

IVA-PHE-HIS[CH$_2$NH]STA-LEU-NHCH$_2$Ph

IVA-PHE-HIS(TRT)[CH$_2$NBOC]STA-LEU-NHCH$_2$Ph (0.2 g) and trifluoroacetic acid (1 ml) are stirred together in dichloromethane (10 ml) at 25° for three hours. The solvent was evaporated and the residue was extracted with ethyl acetate and water. The organic phase was washed with sodium bicarbonate and brine. The EtOAc extract was dried over sodium sulfate, filtered and evaporated. The residue was eluted on silica gel with chloroform and then 10% methanol/ethyl acetate to give 0.1 g. 3,8,11,14-Tetraazaoctadecanamide, 6-hydroxy-10-(1H-imidazol-4-ylmethyl)-17-methyl-2,7-bis(2-methylpropyl)-4,12,15-triazo-N,13-bis(phenylmethyl)-, [2S-(2R*,6R*,7R*,10R*,13R*)].

This compound could also be designated as IVA-PHE-HIS[CH2NH]STA-LEU-NHCH2Ph.

Calcd. for $C_{41}H_{61}N_7O_5 \cdot 1.0CH_2Cl_2$ (MW 816.89): C, 61.75; H, 7.77; N, 12.00. Found: C, 62.02; H, 7.37; N, 12.08.

EXAMPLE 67

BOC-PHE[CH2NOH]PHE-STA-LEU-NHCH2Ph

BOC-PHE[CH2NH]PHE-LEU-NHCH2Ph (0.5 g) was dissolved in dichloromethane (20 ml) at 0°. m-Chloroperbenzoic acid (0.14 g) was added and the mixture was allowed to warm to 25° and stir for four hours. The solvent was evaporated and the residue was dissolved in ethyl acetate and extracted with 10% sodium hydroxide. The extract was washed with brine and dried over sodium sulfate. The solvent was filtered and evaporated and the residue was eluted on silica gel with 1:1 ethyl acetate/hexane to give 0.2 g of the product. 2,5,8,13,16-Pentaazaheptadecanoic acid, 5,10-dihydroxy-9,14-bis(2-methylpropyl)-7,12,15-trioxo-17-phenyl-3,6-bis(phenylmethyl)-, 1,1-dimethylethyl ester, [3S-(3R*,6R*,9R*,10R*,14*)].

This compound could also be designated as BOC-PHE[CH2NOH]PHE-STA-LEU-NHCH2Ph.

Calcd. for $C_{44}H_{63}N_5O_7 \cdot 1.0EtOAc$ (MW 862.09): C, 66.87; H, 8.30; N, 8.12. Found: C, 66.66; H, 7.49; N, 8.59.

EXAMPLE 68

BOC-CYCLOHEXYLALA[CH2NH]HIS-STA-LEU-NHCH2Ph

BOC-CYCLOHEXYLALA[CH2NH]HIS(TRT)-STA-LEU-NHCH2Ph (0.7 g) was dissolved in 80% acetic acid/water (15ml) and heated on a steam bath for 5 minutes. The mixture was allowed to slowly cool to 25° and then the solvent was evaporated. The residue was dissolved in ether and extracted with 1N citric acid. The aqueous phase was neutralized with sodium bicarbonate and extracted with ethyl acetate. The organic phase was washed with brine, dried over sodium sulfate, filtered, and evaporated to give 0.4 g of the product. 2,5,8,13,16-Pentaazaheptadecanoic acid, 3-(cyclohexylmethyl)-10-hydroxy-6-(1H-imidazol-4-ylmethyl)-9,14-bis(2-methylpropyl)-7,12,15-trioxo-17-phenyl-, 1,1-dimethylethyl ester, [3S-(3R*,6R*,9R*,10R*,14R*)]-.

This compound could also be designated as BOC-CYCLOHEXYLALA[CH2NH]HIS-STA-LEU-NHCH2Ph.

Calcd. for $C_{41}H_{67}N_7O_6 \cdot 0.2CH_2Cl_2$ (MW 770.99): C, 64.18; H, 8.81; N, 12.72. Found: C, 63.81; H, 8.89; N, 12.97.

EXAMPLE 69

BOC-PHE[CH2NOH]HIS-STA-LEU-NHCH2Ph

BOC-PHE[CH2NOH]HIS(TRT)-STA-LEU-NHCH2Ph (0.5 g) was dissolved in 80% acetic acid/water (15 ml) and then was heated on a steam bath for 5 minutes. The mixture was allowed to slowly cool to 25°. The solvent was evaporated and the residue was dissolved in ethyl acetate. The solution was washed with sodium bicarbonate solution and brine. The extract was dried over sodium sulfate, filtered and evaporated. The residue was eluted on silica gel with dichloromethane then EtOAc-MeOH (9:1) to give 0.3 g of the desired compound. 2,5,8,13,16-Pentaazaheptadecanoic acid, 5,10-dihydroxy-6-(1H-imidazol-4-ylmethyl)-9,14-bis(2-methylpropyl)-7,12,15-trioxo-17-phenyl-3-(phenylmethyl)-, 1,1-dimethylethyl ester, [3S-(3R*,6R*,9R*,10R*,14R*)]-.

This compound could also be designated as BOC-PHE[CH2NOH]HIS-STA-LEU-NHCH2Ph.

Calcd. for $C_{41}H_{61}N_7O_7$ (MW 763.95): C, 64.46; H, 8.05; N, 12.84. Found: C, 62.63; H, 7.83; N, 12.36.

EXAMPLE 70

IVA-PHE-HIS-CYCLOHEXYLALA[CH2NH]LEU-NHCH2Ph

IVA-PHE-HIS(TRT)-CYCLOHEXYLALA[CH2NBOC]LEU-NHCH2Ph (0.7 g) was dissolved in dichloromethane (15 ml) and trifluoroacetic acid (4 ml) was added. The mixture was stirred for two hours at 25°. The solvent was evaporated and 80% acetic acid/water (15 ml) was added. The mixture was heated on a steam bath for 5 minutes and then was allowed to slowly cool to 25°. The solvent was evaporated and the residue was dissolved in ethyl acetate and extracted with sodium carbonate. The organic layer was washed with brine, dried over sodium sulfate, filtered and evaporated. The residue was eluted from silica gel with dichloromethane and then 10% methanol/ethyl acetate to give 0.4 g of the product. L-histidinamide, N-(3-methyl-1-oxobutyl)-L-phenylalanyl-N-[1-cyclohexylmethyl]-2-[[3-methyl-1-[[(phenylmethyl)amino]carbonyl]butyl]amino]ethyl]-, [S-(R*,R*)].

This compound could also be designated as IVA-PHE-HIS-CYCLOHEXYLALA[CH2NH]LEU-NHCH2Ph.

Calcd. for $C_{42}H_{61}N_7O_4 \cdot 0.25H_2O$ (MW 732.47): C, 68.87; H, 8.46; N, 13.39. Found: C, 67.91; H, 8.25; N, 13.08.

EXAMPLE 71

IVA-ILE[CH2NH]VAL-STA-LEU-NHCH2Ph

To a flask containing 600 mg (0.76 mmole) of IVA-ILE[CH2NZ]VAL-STA-LEU-NHCH2Ph in 30 ml of methanol was added 0.020 g of 20% palladium on charcoal and the mixture was placed under a hydrogen atmosphere. The magnetically stirred solution was monitored by TLC until completion. When the reaction was complete, the mixture was filtered through Celite. The solvent was removed under reduced pressure to yield 0.49 g of a yellow solid. This solid was chromatographed on silica gel and eluted with chloroform/methanol (99/1). The appropriate fractions were combined to give the fast moving isomer of 3,8,11,14-tetraazaoctadecanamide, 6-hydroxy-17-methyl-10-(1-methylethyl)-13-(1-methylpropyl)-2-7-bis(2-methylpropyl)-4,9,15-trioxo-N-(phenylmethyl). There was obtained 90 mg of this isomer designated as IVA-VAL[CH2NH]-VAL-STA-LEU-NHCH2Ph.

Calcd. for $C_{37}H_{65}N_5O_5$ (MW 659.93): C, 67.34; H, 9.93; N, 10.61. Found: C, 67.22; H, 9.45; N, 9.89.

$[\alpha]_D^{23} = -21.8°$ (C, 0.96, MeOH).

EXAMPLE 72

IVA-ILE[CH₂NH]VAL-STA-LEU-NHCH₂Ph

Further elution from the column in the previous example gave 0.13 g of a slower moving diastereomer, designated as the title compound.

Calcd. for $C_{37}H_{65}N_5O_5 \cdot 0.5CH_3OH$ (MW 675.95): C, 66.63; H, 9.99; N, 10.36. Found: C, 66.75; H, 9.90; N, 9.74.

$[\alpha]_D^{23} = -29.2°$ (C, 1.06, MeOH).

EXAMPLE 73

IVA-ILE[CH₂NH]ILE-STA-LEU-NHCH₂Ph

A solution of 0.380 g (1.2 mmole) of IVA-ILE[CH₂NH]ILE, 0.311 g (1.2 mmole) of hydroxybenzotriazole, and 0.5 g (1.2 mmole) of STA-LEU-NHCH₂Ph.HCl in 20 ml of dimethylformamide was cooled to 0°. To this solution was added 0.167 ml (1.2 mmole) of triethylamine followed 10 minutes later by a solution of 0.248 g (1.2 mmole) of N,N'-dicyclohexylcarbodiimide in dimethylformamide. The solution was kept at 0° for one hour and then allowed to warm to room temperature overnight.

The solvent was removed under reduced pressure and the residue taken up in ethyl acetate. The ethyl acetate solution was filtered and washed with 1N HCl, saturated NaHCO₃ and saturated NaCl. After drying the solvent was removed in vacuo to afford 0.84 g of a white solid. The solid was chromatographed on silica gel and eluted with chloroform-methanol (99/1). The appropriate fractions were combined to give 0.170 g of the product, 3,8,11,14-tetraazaoctadecanamide, 6-hydroxy-17-methyl-10,13-bis(1-methylpropyl)-2,7-bis(2-methylpropyl)-4,9,15-trioxo-N-(phenylmethyl). This can also be designated as IVA-ILE[CH₂NH]ILE-STA-LEU-NHCH₂Ph.

Calcd. for $C_{38}H_{67}N_5O_5 \cdot 0.2CHCl_3$ (MW 697.83): C, 65.75; H, 9.70; N, 10.04. Found: C, 65.92; H, 9.67; N, 10.03.

$[\alpha]_D^{23} -32.6°$ (C, 1.09, MeOH).

EXAMPLE 74

BOC-PHE[CH₂NH]HIS-PHSTA-LEU-NHCH₂Ph

To a solution of 0.2 g (0.22 mmole) of BOC-PHE[CH₂NZ]HIS-PHSTA-LEU-NHCH₂Ph in 75 ml of methanol was added 0.029 g of 20% palladium on carbon and the mixture stirred under an atmosphere of hydrogen. After the appropriate time, the solvent was removed under reduced pressure to afford 0.18 g (100%) of product, 2,5,8,13,16-pentaazaheptadecanoic acid, 10-hydroxy-6-(1H-imidazol-4-ylmethyl)-14-(2-methylpropyl)-7,12,15-trioxo-17-phenyl-3,9-bis(phenylmethyl)-, 1,1-dimethylethyl ester. This compound can also be designated as BOC-PHE[CH₂NH]HIS-PHSTA-LEU-NHCH₂Ph.

Calcd. for $C_{44}H_{59}N_7O_6 \cdot 0.2CHCl_3$ (MW 805.84): C, 65.88; H, 7.40; N, 12.17. Found: C, 65.76; H, 7.49; N, 11.91.

EXAMPLE 75

BOC-LEU[CH₂O]PHGLY-STA-ALA-STA-NHCH₂Ph

A stirred suspension of 0.42 g (1.1 mmole) of 2-[[4-methyl-2-[[(phenylmethoxy)carbonyl]amino]pentyl]oxy]benzeneacetic acid (α-carbon was (±), other stereo site was S) and 0.3 g of 20% palladium on carbon in 100 ml of methanol was exposed to hydrogen gas for 15 minutes, the suspension was purged with nitrogen gas, filtered, and the solvent evaporated in vacuo. The residue was dissolved in 25 ml of dioxane and 25 ml of water and 0.11 g (1.1 mmole) of triethylamine and 0.26 g (1.1 mmole) of di-tertiary-butyl dicarbonate were added at 5°. After one hour the solvents were evaporated to give 0.23 g of BOC-LEU[CH₂O]PHGLY. This derivative, 0.2 g (0.57 mmole). STA-ALA-STA-NHCH₂Ph, 0.31 g (0.63 mmole), 1-hydroxybenzotriazole, 0.088 g (0.57 mmole) and N,N'-dicyclohexylcarbodiimide, 0.12 g (0.57 mmole) were dissolved in 40 ml of dimethylformamide and 160 ml of dichloromethane at 0°. The mixture was allowed to reach room temperature over six hours, filtered, the solvents evaporated in vacuo and the residue dissolved in 200 ml of dichloromethane and extracted successively with 10% citric acid, 10% Na₂CO₃, and saturated sodium chloride. The dichloromethane layer was separated, dried over sodium sulfate, evaporated in vacuo and the residue purified by chromatography over 100 g of silica gel and eluting with dichloromethane-methanol (95:5) to give 10,18-dihydroxy-14-methyl-3,9,17-tris-(2-methylpropyl)-7,12,15,20-tetraoxo-6,22-diphenyl-5-oxa-2,8,13,16,21-pentaazadocosanoic acid, 1,1-dimethylethyl ester; (center at position 6 was R,S; all others were S), 0.35 g; $[\alpha]_D^{23} = -84.5°$ (C, 0.6, MeOH). This compound can also be designated as BOC-LEU[CH₂O]PHGLY-STA-ALA-STA-NHCH₂Ph.

Calcd. for $C_{45}H_{71}N_5O_9$ (MW 826.06): C, 65.43; H, 8.66; N, 8.48. Found: C, 65.71; H, 8.59; N, 8.29.

EXAMPLE 76

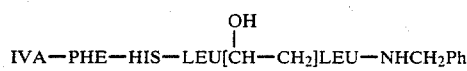

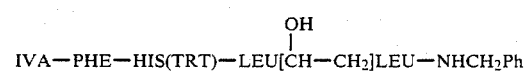

(0.9 g) was dissolved in 80% acetic acid/water. The mixture was heated on a steam bath for five minutes and allowed to slowly cool to 25°. The solvent was evaporated and the residue extracted with ethyl acetate and sodium bicarbonate. The organic layer was washed with brine, dried over sodium sulfate, filtered, and evaporated. The residue was eluted from silica gel with ethyl acetate and then 10% methanol/ethyl acetate to give 0.5 g of product.

L-Histidinamide, N-(3-methyl-1-oxobutyl)-L-phenylalanyl-N-[2-hydroxy-6-methyl-1-(2-methylpropyl)-4-[[(phenylmethyl)amino]carbonyl]heptyl].

This can also be called

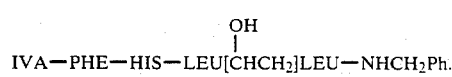

EXAMPLE 77

Z—NAPHTHYLALA—HIS—CYCLOHEXYLALA[CH(OH)—CH$_2$]GLY—NH—CH$_2$CH(CH$_3$)CH$_2$CH$_3$

Z—NAPHTHYLALA—HIS(TRT)—CYCLOHEXYLALA[CH(OH)CH$_2$]GLY—NHCH$_2$CH(CH$_3$)CH$_2$CH$_3$ (0.8 g) was dissolved in 80% acetic acid/water and heated on a steam bath for five minutes. The mixture was allowed to slowly cool to 25°. The solvent was evaporated and the residue was extracted with ethyl acetate and sodium carbonate. The organic layer was washed with brine, dried over sodium sulfate, filtered, and evaporated. The residue was eluted from silica gel with chloroform and then 10% methanol/dichloromethane to give 0.5 g of product.

This can be called

Z—NAPHTHYLALA—

—HIS—CYCLOHEXYLALA[CH(OH)CH$_2$]GLY—

—NHCH$_2$CH(CH$_3$)CH$_2$CH$_3$.

Calcd. for C$_{44}$H$_{58}$N$_6$O$_6$.0.15CH$_2$CH$_2$, 0.17C$_4$H$_8$O$_2$ (MW 794.67): C, 67.76; H, 7.57; N, 10.58. Found: C, 67.47; H, 7.48; N, 10.57.

EXAMPLE 78

IVA—PHE—HIS—

—CYCLOHEXYLALA[CH(OH)—CH$_2$]LEU—NHCH$_2$Ph

IVA—PHE—HIS(TRT)—

—CYCLOHEXYLALA[CH(OH)CH$_2$]LEU—NHCH$_2$Ph (0.5 g) was dissolved in 80% acetic acid/water and heated on a steam bath for five minutes. The mixture was allowed to slowly cool to 25° and then the solvent was evaporated. The residue was extracted with ethyl acetate and sodium carbonate. The organic phase was washed with brine, dried over sodium sulfate, filtered, and evaporated. The residue was eluted from silica gel with chloroform and then with 10% methanol/ethyl acetate to get 0.26 g of product.

This can be called

IVA—PHE—HIS—

—CYCLOHEXYLALA[CH(OH)CH$_2$]LEU—NHCH$_2$Ph.

Analysis: Calcd.: C, 68.04; H, 8.23; N, 11.07. Found: C, 67.55; H, 8.10; N, 11.00.

EXAMPLE 79

BOC—CYCLOHEXYLALA[CH(OH)CH$_2$]LEU—

—STA—LEU—NHCH$_2$Ph

BOC—CYCLOHEXYLALA[C(O)CH$_2$]LEU—

—STA—LEU—NHCH$_2$Ph (0.6 g) was dissolved in ethanol (20 ml) and cooled to 0°. Sodium borohydride (0.1 g) was added and the mixture was allowed to warm to 25° and stir for two hours. Acetic acid and water 1:1 was added and the solvent was evaporated. The residue was extracted with sodium carbonate and ethyl acetate. The organic phase was washed with brine, dried over sodium sulfate, filtered, and evaporated. The residue was eluted from silica gel with dichloromethane and then ethyl acetate to give 0.6 g product.

This can be called

BOC—CYCLOHEXYLALA[CH(OH)CH$_2$]LEU—

—STA—LEU—NHCH$_2$Ph.

Analysis: Calcd: C, 67.70; H, 9.74; N, 7.52. Found: C, 67.87; H, 9.64; N, 7.80.

EXAMPLE 80

IVA—PHE—HIS—CYCLOHEXYLALA[CHOHCH$_2$]GLY—

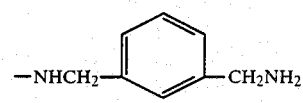

IVA—PHE—HIS(TRT)—
—CYCLOHEXYLALA[CHOHCH$_2$]GLY—

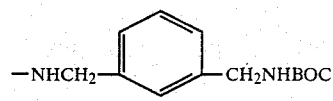

(1 g) was dissolved in dichloromethane (20 ml) and trifluoroacetic acid (4 ml) was added. The mixture was stirred for two hours at 25°. The solvent was evaporated and the residue was dissolved in acetic acid/water 80:20. The mixture was heated on a stream bath for five minutes and then allowed to slowly cool to 25°. The solvent was evaporated and the mixture was neutralized with sodium carbonate in water. The solid was filtered off and washed with chloroform and ethyl acetate to remove triphenylcarbinol. The residual solid was dissolved in methanol, filtered, and the solvent evaporated to give 0.3 g of product.

This can be called

IVA—PHE—HIS—CYCLOHEXYLALA[CHOHCH$_2$]GLY—

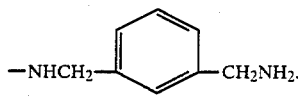

EXAMPLE 81

IVA—PHE—HIS—CYCLOHEXYLALA[CHOHCH$_2$]LEU—

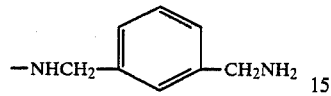

IVA—PHE—HIS(TRT)—
    —CYCLOHEXYLALA[CHOHCH$_2$]LEU—

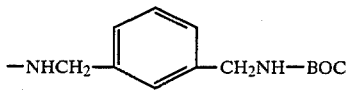

(1 g) was dissolved in dichloromethane (20 ml) and trifluoroacetic acid (4 ml) was added. The mixture was stirred for two hours at 25°. The solvent was evaporated and the residue was dissolved in 80% acetic acid. The mixture was heated on a steam bath for five minutes and then allowed to slowly cool to 25°. The solvent was evaporated and the residue was neutralized with 10% sodium hydroxide. The mixture was filtered and the collected solid was eluted from silica gel with ethyl acetate and then 1:1 ethyl acetate/methanol to give 0.6 g of product.

This can be called

IVA—PHE—HIS—CYCLOHEXYLALA[CHOHCH$_2$]LEU—

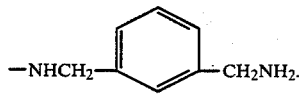

EXAMPLE 82

IVA—PHE—HIS—CYCLOHEXYLALA[CHOHCH$_2$]GLY—

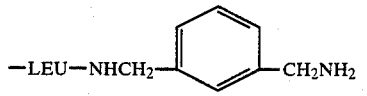

IVA—PHE—HIS(TRT)—
    —CYCLOHEXYLALA[CHOHCH$_2$]GLY—LEU—

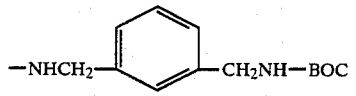

(0.80 g) was dissolved in dichloromethane (15 ml) and trifluoroacetic acid (4 ml) was added. The mixture was stirred at 25° for two hours. The solvent was evaporated and the residue was dissolved in 80% acetic acid. The mixture was heated on a steam bath for five minutes and then allowed to slowly cool to 25°. The solvent was evaporated. The mixture was neutralized with sodium hydroxide and then extracted with ethyl acetate-THF. The extract was evaporated and the residue was dissolved in methanol. The product was precipitated with ether. The product was collected and dried. There was obtained 0.35 g, mp 200°–210°.

This can be called

IVA—PHE—HIS—CYCLOHEXYLALA[CHOHCH$_2$]GLY—

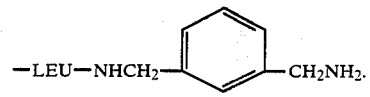

EXAMPLE 83

BOC-PHE[CH$_2$NH]HIS-CYSTA-LEU-NHCH$_2$Ph

A solution of 0.6 g of BOC-PHE[CH$_2$NH]HIS(TRT-)CYSTA-LEU-NHCH$_2$Ph in 15 ml of 80% acetic acid was warmed on a steam bath for five minutes, then allowed to cool to 25° over one hour. The solvent was removed under reduced pressure and the residue taken up in ethyl acetate. This solution was washed with 10% Na$_2$CO$_3$ solution, then saturated NaCl solution, then dried over Na$_2$SO$_4$. After removal of the solvent under reduced pressure, the residue was chromatographed on silica gel, eluting with EtOAc/MeOH (9:1). Combining the appropriate fractions with the aid of CH$_2$Cl$_2$ gave 0.4 g of product, BOC-PHE[CH$_2$NH]HIS-CYSTA-LEU-NHCH$_2$Ph, as a white foam.

Calcd. for C$_{44}$H$_{65}$N$_7$O$_6$.0.1CH$_2$Cl$_2$.0.16C$_2$H$_8$O$_4$ (MW 806.76): C, 66.13; H, 8.31; N, 12.15. Found: C, 65.85; H, 8.33; N, 12.10.

EXAMPLE 84

BOC-PHE-HIS-PHE[CHOHCH=CH-CO]NHCH$_2$CH(CH$_3$)CH$_2$CH$_3$

A solution of 290 mg (0.67 mmole) of HIS-PHE[-CHOHCH=CHCO]NHCH$_2$CH(CH$_3$)CH$_2$CH$_3$, 180 mg (0.67 mmole) of BOC-PHE, and 92 mg (0.67 mmole) of hydroxybenzotriazole in 15 ml DMF was cooled in ice and treated with 142 mg (0.67 mmole) of N,N'-dicyclohexylcarbodiimide. The mixture was kept at 0° for 0.5 hour and then allowed to stir at room temperature overnight. The N,N'-dicyclohexylurea was filtered off and the solvent removed under reduced pressure. The residue was triturated with hexane and stirred overnight in hexane. The solid was collected and washed with hexane giving 400 mg of product. This can be called BOC-PHE-HIS-PHE-[CHOHCH=CH-CO]NHCH$_2$CH(CH$_3$)CH$_2$CH$_3$.

EXAMPLE 85

BOC-PHE-HIS-PHE[CHOHCH$_2$]GLY-NHCH$_2$CH(CH$_3$)CH$_2$CH$_3$

A solution of 300 mg of BOC-PHE-HIS-PHE[-CHOHCH=CHCO]NHCH$_2$CH(CH$_3$)CH$_2$CH$_3$ in 75 ml of MeOH was treated with 0.2 g of Raney nickel and reduced at 25°, 50 psi for 24 hours. The mixture was filtered and the solvent removed under reduced pressure. The residue was chromatographed on silica gel, eluting with CHCl$_3$/MeOH (93/7). There was obtained 105 mg of pure product as an off white solid. This can be called BOC-PHE-HIS-PHE[CHOHCH$_2$]GLY-NHCH$_2$CH(CH$_3$)CH$_2$CH$_3$.

Calcd. for $C_{37}H_{52}N_6O_6 \cdot 0.2CHCl_3$ (MW 700.71): C, 63.76; H, 7.51; N, 11.99. Found: C, 63.79; H, 7.88; N, 11.81.

The following intermediates are provided to enable one skilled in the art to practice the present invention.

INTERMEDIATES FOR EXAMPLE 4

PHE[CH=CH]GLY-OCH$_3$

A solution of 1.0 g (3.1 mmole) of [S-(E)]-5-[[(1,1-dimethylethoxy)carbonyl]amino]-6-phenyl-3-hexenoic acid, methyl ester [J. Chem. Soc. 799 (1980)] in 2 ml of dichloromethane was treated with 10 ml of trifluoroacetic acid and swirled occasionally over one hour at room temperature. The solution was then diluted with dichloromethane and the solvent removed under reduced pressure. The residue was taken up in ethyl acetate and washed twice with 5% potassium carbonate solution. Drying over MgSO$_4$ and removal of the solvent under reduced pressure gave 630 mg of [S(E)]-5-amino-6-phenyl-3-hexenoic acid. The crude product was used directly in the next step.

IVA-PHE[CH=CH]GLY-OCH$_3$

A solution of 630 mg (2.9 mmole) of [S-(E)]-5-amino-6-phenyl-3-hexenoic acid in 15 ml of dichloromethane was cooled in ice and treated with 0.44 ml (3.2 mmole) of triethylamine followed by 0.39 ml (3.2 mmole) of isovaleryl chloride. The solution was left at 0° for 0.5 hour, then at room temperature for 1.5 hours. The solvent was removed under reduced pressure and the residue taken up in ethyl acetate, washed twice with 1N HCl, then saturated NaHCO$_3$, then saturated NaCl. After drying over MgSO$_4$ the solvent was removed under reduced pressure leaving a solid. Recrystallization from dichloromethane/hexane gave 670 mg of [S-(E)]-5-[(3-methyl-1-oxobutyl)amino]-6-phenyl-3-hexenoic acid, methyl ester, mp 79°–80°, $[\alpha]_D^{23} = -18.3°$ (C, 0.9, CH$_3$OH).

Calcd. for $C_{18}H_{25}NO_3$ (MW 303.39): C, 71.26; H, 8.31; N, 4.62. Found: C, 70.88; H, 8.24; N, 4.56.

The structure was also confirmed by NMR spectroscopy.

IVA-PHE[CH=CH]GLY

A solution of 589 mg (1.94 mmole) of [S-(E)]-5-[(3-methyl-1-oxobutyl)amino]-6-phenyl-3-hexenoic acid, methyl ester in 7 ml of methanol was treated with 2.2 ml (2.2 mmole) of 1N NaOH solution and stirred at room temperature for two hours. An additional 1.5 ml of 1N NaOH was then added and the solution allowed to stir an additional two hours. The solution was then diluted with water and washed with ether. The aqueous solution was adjusted to pH 2 and extracted twice with ethyl acetate. The ethyl acetate solution was washed with saturated NaCl, dried over MgSO$_4$ and the solvent removed under reduced pressure leaving 560 mg of [S-(E)]-5-[(3-methyl-1-oxobutyl)amino]-6-phenyl-3-hexenoic acid as a cream solid. The crude product was used directly in the next step.

INTERMEDIATES FOR EXAMPLE 5

BOC-PHSTA-LEU-NHCH$_2$Ph

To a solution of 240 mg (0.77 mmole) of BOC-PHSTA, 199 mg (0.77 mmole) of LEU-NHCH$_2$Ph, and 105 mg (0.77 mmole) of hydroxybenzotriazole in 20 ml of DMF was added 0.11 ml (0.77 mmole) of triethylamine. The solution was cooled to 0° and a solution of 160 mg (0.77 mmole) of N,N'-dicyclohexylcarbodiimide in 5 ml of DMF added. After one hour at 0°, the solution was allowed to warm to room temperature overnight. The solvent was removed under pressure and the residue dissolved in ethyl acetate. The organic solution was washed with 1N HCl, saturated NaHCO$_3$, and saturated NaCl. The solution was dried and the solvent removed under reduced pressure to give 0.37 g of crude product. Chromatography on silica gel, eluting with CHCl$_3$/MeOH (9:1) gave 240 mg of pure BOC-PHSTA-LEU-NHCH$_2$Ph. $[\alpha]_D^{23} = -21.9°$ (C, 0.92, MeOH).

PHSTA-LEU-NHCH$_2$Ph

To a solution of 0.24 g (0.47 mmole) of BOC-PHSTA-LEU-NHCH$_2$Ph in 30 ml of dichloromethane was added HCl gas until saturation. When the reaction was complete, the solvent was removed under reduced pressure to give 0.2 g of product as the hydrochloride as a white foam.

Calcd. for $C_{24}H_{34}N_3O_3Cl \cdot 0.25CH_2Cl_2$ (MW 469.23): C, 62.07; H, 7.41; N, 8.95. Found: C, 61.87; H, 7.60; N, 8.84.

$[\alpha]_D^{23} = -25.4°$ (C, 1.14, MeOH).

INTERMEDIATE FOR EXAMPLE 6

CYSTA-LEU-NHCH$_2$Ph

To a solution of 1.21 g (2.3 mmole) of BOC-CYSTA-LEU-NHCH$_2$Ph (prepared in a manner similar to BOC-PHSTA-LEU-NHCH$_2$Ph, above) in 30 ml dichloromethane was added HCl gas until saturation. When the reaction was complete, the solvent was removed under reduced pressure. The residue was redissolved in CH$_2$Cl$_2$ and reevaporated to give 1.05 g of product, as a white foam. $[\alpha]_D^{23} = -21.6°$ (C, 1.01, MeOH).

INTERMEDIATES FOR EXAMPLE 7

BOC-TRP-N(CH$_3$)-OCH$_3$

A suspension of 29.0 g (0.1 mole) of BOC-TRP in 500 ml of dichloromethane was treated with 12.3 ml (0.1 mole) of N-methylpiperidine causing solution. After cooling to 0°, 8.0 ml (0.1 mole) of methyl chloroformate was added rapidly and stirred for two minutes. In a separate flask, a suspension of 9.75 g (0.1 mole) of 0,N-dimethylhydroxylamine.HCl in 100 ml of dichloromethane was treated with 12.3 ml (0.1 mole) of N-methylpiperidine causing solution. This solution was then added rapidly to the previously prepared mixed anhydride solution. After stirring at 0° for one hour, the solution was allowed to stir at room temperature overnight. The solvent was removed under reduced pressure and the residue taken up in ethyl acetate. The precipitated N-methylpiperidine.HCl was filtered off and the filtrate washed with 1N HCl, water, saturated NaHCO$_3$, then saturated NaCl. After drying over MgSO$_4$ and removal of the solvent under reduced pressure the crude product was obtained. Recrystallization from EtOH/H$_2$O gave 24.3 g of pure product, mp 132°–133°, $[\alpha]_D^{23} = -12.3°$ (C, 0.74, CH$_3$OH).

Calcd. for $C_{18}H_{25}N_3O_4$ (MW 347.40): C, 62.23; H, 7.25; N, 12.10. Found: C, 62.32; H, 7.34; N, 12.00.

The structure was also confirmed by NMR spectroscopy.

BOC-TRP[CHO]

A solution of 24.0 g (0.069 mole) of BOC-TRP-N-(CH$_3$)-OCH$_3$ in 300 ml of tetrahydrofuran was cooled in ice and treated in portions with 3.5 g (0.092 mole) of lithium aluminum hydride. After stirring at 0° for 0.5 hours, a solution of 25 g of sodium bisulfate in 350 ml of water was added as rapidly as possible while keeping foaming under control. The pH was adjusted to 3.0 and the mixture was extracted three times with ethyl acetate. The combined ethyl acetate solution was washed with 1N citric acid, saturated $NaHCO_3$, then saturated NaCl. Drying over $MgSO_4$ and removal of the solvent under reduced pressure left 19.5 g of crude N-(t-butoxycarbonyl)-L-tryptophanal. The crude product was used directly in the next step. The structure was confirmed by NMR spectroscopy.

Wittig Reaction Using BOC-TRP[CHO]

Under nitrogen, a suspension of 32.65 g (0.072 mole) of 1-trimethylsilyl-propyne-3-triphenylphosphonium bromide [J. Chem. Soc. 1981 (1974)] in 365 ml of tetrahydrofuran was cooled to −80° and treated dropwise with a solution of 20.76 g (0.072 mole) of N-(t-butoxycarbonyl)-L-tryptophanal in 365 ml of tetrahydrofuran. After an additional hour at −80°, the mixture was allowed to stir at room temperature overnight. The solvent was removed under reduced pressure and the residue triturated three times with ethyl ether, filtering off the triphenylphosphine oxide. The combined ether extracts were washed with saturated NaCl, dried over $MgSO_4$, and the solvent removed under reduced pressure leaving 23 g of a brown oil. After chromatography on silica gel, eluting with dichloromethane, there was obtained 10.5 g of product, [S-(E)]-1,1-dimethylethyl[1-(3-indoylmethyl)-5-trimethylsilyl-2-pentene-4-ynyl]carbamate.

The structure was confirmed by NMR spectroscopy.

BOC-TRP[CH=CH]GLY

Under nitrogen, a solution of 96.2 ml (0.096 mole) of a 1M solution of borane in tetrahydrofuran was cooled in ice and treated dropwise with a solution of 19.5 ml (0.192 mole) of cyclohexene in 210 ml of tetrahydrofuran. After stirring at 0° for one hour, a solution of 10.5 g (0.0275 mole) of [S-(E)]-1,1-dimethylethyl-[1-(3-indoylmethyl)-5-trimethylsilyl-2-pentene-4-ynyl] carbamate in 45 ml of tetrahydrofuran was added dropwise. After stirring at 0° for one hour, the solution was treated dropwise with 37 ml of methanol, 50 ml of 2N sodium hydroxide, then 33 ml of 30% hydrogen peroxide, keeping the temperature below 18° with cooling. The mixture was then stirred at 0° for 20 minutes, then at room temperature for one hour. The mixture was then poured into 700 ml of water containing 37 ml of 2N NaOH. After extracting three times with ether, the pH was brought to 2.2 with diluted HCl and the solution extracted three times with ether. The combined ether solution was washed with saturated NaCl, then dried over $MgSO_4$. Removal of the ether under reduced pressure gave 7.27 g of a brown solid. Recrystallization from ethanol-water gave 5.25 g of product [S-(E)]-5-[[(1,1-dimethylethoxy)carbonyl]amino]-6-(3-indoyl)-3-hexenoic acid, mp 142°-145° d.

The compound can also be designated as BOC-TRP[CH=CH]GLY.

Calcd. for $C_{19}H_{24}N_2O_4$ (MW 344.40): C, 66.26; H, 7.02; N, 8.13. Found: C, 66.34; H, 7.14; N, 7.97.

The structure was confirmed by NMR spectroscopy.

INTERMEDIATE FOR EXAMPLE 17

Wittig Reaction With BOC-CYCLOHEXYLALANINAL

Under nitrogen, a suspension of 31.9 g (0.07 mole) of 1-trimethylsilyl-propyne-3-triphenylphosphonium bromide [J. Chem. Soc. 1981 (1974)] in 365 ml of tetrahydrofuran was cooled to −80° and treated dropwise with 46 ml (0.07 mole) of a 1.55M solution of n-butyl lithium in hexane. After stirring at −80° for one hour, the mixture was treated dropwise with a solution 17.97 (0.07 mole) of N-(t-butoxycarbonyl)-L-cyclohexylalaninal (U.S. Pat. No. 4,477,440) in 365 ml of tetrahydrofuran. After an additional hour at −80°, the mixture was allowed to stir at room temperature overnight. The solvent was removed under reduced pressure and the residue triturated three times with ethyl ether, filtering off the triphenylphosphine oxide. The combined ether extracts were washed with saturated NaCl, dried over $MgSO_4$, and the solvent removed under reduced pressure leaving 28.4 of a brown oil. After chromatography on silica gel, eluting with hexane/dichloromethane (3/2) there was obtained 11.9 g of product, [S-(E)]-1,1-dimethylethyl[1-(cyclohexylmethyl)-5-trimethylsilyl-2-pentene-4-ynyl]carbamate. The structure was confirmed by NMR spectroscopy.

BOC-CYCLOHEXYLALA[CH=CH]GLY

Under nitrogen, a solution of 112 ml (0.112 mole) of a 1M solution of borane in tetrahydrofuran was cooled in ice and treated dropwise with a solution of 22.7 ml (0.224 mole) of cyclohexene in 240 ml of tetrahydrofuran. After stirring at 0° for one hour, a solution of 11.19 g (0.224 mole) of [S-(E)]-1,1-dimethylethyl-[1-(cyclohexylmethyl)-5-trimethylsilyl-2-pentene-4-ynyl]carbamate in 50 ml of tetrahydrofuran was added dropwise. After stirring at 0° for one hour, the solution was treated dropwise with 43 ml MeOH, 52 ml of 2N NaOH, then with 38 ml of 30% $H_2O_2$, keeping the temperature below 18° with cooling. The mixture was then stirred at 0° for 20 minutes, then one hour at room temperature. The mixture was poured into 800 ml of water containing 43 ml of 2N NaOH. After extracting three times with ether, the pH was brought to 2.2 with dilute HCl and the solution extracted three times with ether. The combined ether solution was washed with saturated NaCl, then dried over $MgSO_4$. Removal of the ether under reduced pressure left 8.44 g of the crude product. After chromatography on silica gel, eluting with $CHCl_3$—$CH_3OH$ (19/1) there was obtained 7.7 g of pure product, [S-(E)]-5-[[(1,1-dimethylethoxy) carbonyl]amino]-6-cyclohexyl-3-hexenoic acid. The structure was confirmed by NMR and MS spectroscopy.

INTERMEDIATE FOR EXAMPLE 8

A solution of 19.4 ml (0.15 mole) of m-xylenediamine in 400 ml of $CH_2Cl_2$ was cooled to −78° and treated slowly with a solution of 40.0 g (0.16 mole) of N-(benzyloxycarbonyloxy)succinimide in 200 ml of $CH_2Cl_2$. After one hour at −78°, the mixture was allowed to warm to room temperature. The mixture was filtered and the solid suspended in dichloromethane and 2N HCl added until solution occurred. The aqueous layer was separated and brought to pH 12 with 50% NaOH. The solution was extracted twice with $CHCl_3$, and the $CHCl_3$ washed with saturated NaCl. Drying over MgSO₄ and removal of the solvent under reduced pressure gave 25.3 g of the crude product.

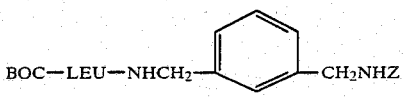

To a solution of 3.32 g (0.013 mole) of BOC-LEU in 30 ml of dimethylformamide was added 1.8 g (0.013 mole) of hydroxybenzotriazole and 2.74 g (0.013 mole of dicyclohexylcarbodiimide. The solution was cooled to 0° and a solution of 3.6 g (0.013 mole) of the mono-Z derivative of m-xylenediamine in 20 ml of dimethylformamide added. The solution was kept at 0° for one hour and then allowed to warm to room temperature overnight. The solvent was removed under reduced pressure and the residue taken up in ethyl acetate. The ethyl acetate solution was washed with 1N HCl, H₂O, saturated NaHCO₃, saturated NaCl, and then dried. The solvent was removed under reduced pressure to give 6.11 g of a solid. Chromatography on silica gel, eluting with chloroform/methanol (99/1) gave 5.74 g of the product.

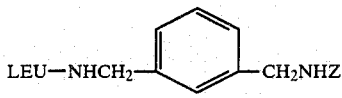

A solution 5.74 g (0.012 mole) of the BOC-derivative in 60 ml of dichloromethane was saturated with HCl gas. When the reaction was complete, the solvent was removed under reduced pressure. The residue was redissolved in dichloromethane and evaporated to give 3.71 g (74.6%) of product as a foam.

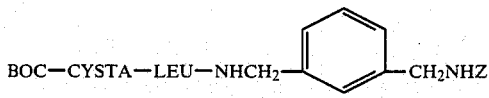

A solution of 2.72 g (8.6 mmole) of BOC-CYSTA, 1.16 g (8.6 mmole) of hydroxybenzotriazole and 3.61 g (8.6 mmole) of

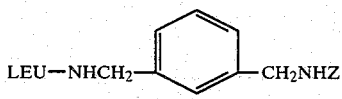

in 30 ml of dimethylformamide was cooled to 0° and 1.2 ml (8.6 mmole) of Et₃N added. A solution of 1.78 g (8.6 mmole) of dicyclohexylcarbodiimide in 10 ml of dimethylformamide was added, the mixture kept at 0° for an hour, and then allowed to warm to room temperature overnight. The mixture was filtered to remove the dicyclohexylurea, and the solvent was removed under reduced pressure. The residue was dissolved in ethyl acetate, washed with 1N HCl, H₂O, saturated NaHCO₃, saturated NaCl, and then dried. The solvent was removed under reduced pressure to yield 6.03 g of a foam. The foam was chromatographed on silica gel, eluting with chloroform/methanol (98/2) to give 3.82 g (65.3%) of the product.

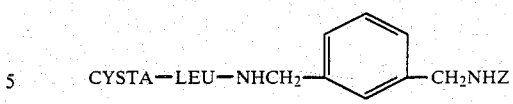

A solution of 3.63 g (0.0053 mole) of the BOC-derivative in 40 ml of dichloromethane was saturated with HCl gas. When the reaction was complete, the solvent was removed under reduced pressure. The residue was redissolved in dichloromethane and evaporated under reduced pressure to give 2.92 g of product as a foam.

INTERMEDIATES FOR EXAMPLES 25 AND 26

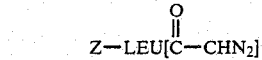

Z-LEU (20 g) and N-methylpiperidine (9.1 ml) were dissolved in dichloromethane (300 ml) and cooled to −20°. Isobutyl chloroformate (9.8 ml) was added dropwise and the mixture stirred for ten minutes after the addition was complete. The mixture was filtered under nitrogen into a cold flask and diazomethane (6 g) in ether added. The mixture was left to stand at 0° overnight. A nitrogen stream was bubbled through the solution to remove any diazomethane. The solvent was evaporated and the residue recrystallized from isopropyl ether/hexane to give 16 g of product, the diazoketone derived from Z-LEU.

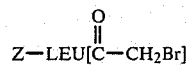

The diazoketone (15 g) was dissolved in ether (200 ml) and cooled to −20°. Gaseous hydrogen bromide was bubbled in until the pH of the solution was acidic when tested with litmus paper. The solvent was evaporated to give the product (16 g) as an oil.

Sodium hydride (1.81 g) (60%) was washed with hexane and then suspended in dimethylformamide (10 ml). The mixture was cooled to 0° and di-t-butyl malonate (9.79 g) was added. The mixture was stirred for one hour then was treated with a solution of the bromoketone (15.5 g) in dimethylformamide (30 ml). The mixture was allowed to warm to 25° and was stirred for three hours. 1N citric acid was added and the mixture was extracted with ether. The ether was washed with water, saturated NaHCO₃, and then saturated NaCl. After drying over sodium sulfate, the solvent was evaporated. The residue was recrystallized from hexane to give 12 g of product, mp 81°-82°.

Sodium hydride (1.3 g) (60%) was washed with hexane and then suspended in tetrahydrofuran (200 ml). The above malonate derivative (15 g) was added to the suspension and the mixture was heated to 50° for 0.5 hour. The mixture was cooled to 0° and isobutyl iodide (11 ml) was added. The mixture was allowed to warm to 25° and stirred for 24 hours. 1N citric acid was added and the mixture was extracted with ethyl acetate. The organic phase was washed with water, sodium bicarbonate, and brine. The organic phase was dried over sodium sulfate, filtered and evaporated. The residue was chromatographed on silica gel, eluting with 10% ethyl acetate/hexane to give 10 g of product, propanedioic acid, 2-[5-methyl-2-oxo-3-[[(phenylmethoxy)carbonyl]amino]hexyl]-2-(2-methylpropyl)-, bis(1,1-dimethylethyl)ester.

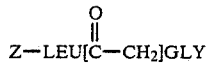

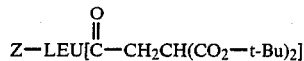

(1 g) was dissolved in trifluoroacetic acid (10 ml) and stirred for three hours at 25°. The solvent was evaporated and the residue dissolved in toluene. The mixture was heated to reflux for four hours. The mixture was allowed to cool and the solvent evaporated. The residue was eluted from silica gel with 1:4 ethyl acetate/hexane to give 0.35 g of product.

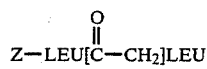

The appropriate malonate derivative from above (1 g) was dissolved in trifluoroacetic acid and stirred at 25° for three hours. The solvent was evaporated and the residue was dissolved in toluene (30 ml). The mixture was heated to reflux for four hours. The mixture was cooled and the solvent was evaporated to give 0.6 g of product, octanoic acid, 7-methyl-2-(2-methylpropyl)-4-oxo-5-[[(phenylmethoxy)carbonyl]amino]; (position 2 is RS, position 5 is S).

Calcd. for $C_{21}H_{31}NO_5$ (MW 377.47): C, 66.82; H, 8.28; N, 3.71. Found: C, 67.02; H, 8.08; N, 3.64.

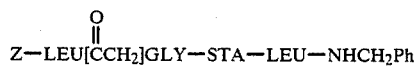

(0.35 g), STA-LEU-NHCH$_2$Ph.HCl (0.45 g), and hydroxybenzotriazole (0.15 g) were dissolved in DMF (20 ml). The mixture was cooled to 0° and triethylamine (15 ml) was added. Dicyclohexylcarbodiimide (0.23 g) was added and the mixture allowed to slowly warm to 25°. The mixture was stirred for 24 hours, then filtered. The filtrate was dissolved in ethyl acetate and the resulting solution was extracted with water, sodium bicarbonate, and brine. The organic phase was dried over sodium sulfate, filtered and evaporated. The residue was eluted from silica gel with 1:5 ethyl acetate/hexane to give 0.35 g of product, 2,5,10,16-tetraheptadecan-17-oic acid, 8-hydroxy-4,9,15-tris(2-methylpropyl)-3,6,11,14-tetraoxo-1-phenyl-, phenylmethyl ester, [4S-(4R*,8R*,9R*,15R*)].

Analysis: Calcd. C, 54.17; H, 9.09; N, 6.32. Found: C, 54.46; H, 9.11; N, 6.49.

-continued

(0.3 g), STA-LEU-NHCH$_2$Ph (0.33 g), and hydroxybenzotriazole (0.11 g) were dissolved in dimethylformamide (20 ml) and cooled to 0°. Triethylamine (0.11 ml) and then dicyclohexylcarbodiimide (0.16 g) were added and the mixture allowed to warm to 25° slowly. The mixture was stirred for 24 hours and then filtered. The filtrate was dissolved in ethyl acetate and extracted with water. The organic layer was washed with water, sodium bicarbonate, and brine. The organic phase was dried over sodium sulfate, filtered, and evaporated. The residue was eluted from silica gel with 15% ethyl acetate/hexane. Combining the fractions using CH$_2$Cl$_2$ gave 0.35 g of product, 2,5,10,16-tetrazaheptadecan-17-oic acid, 8-hydroxy-4,9,12,15-tetrakis(2-methylpropyl)-3,6,11,14-tetraoxo-1-phenyl-, phenylmethyl ester; (all stereo centers are S except for position 6 which is RS).

Calcd. for $C_{42}H_{64}N_4O_7.0.1CH_2Cl_2$ (MW 745.46): C, 67.83; H, 8.68; N, 7.52. Found: C, 67.60; H, 8.82; N, 7.86.

INTERMEDIATES FOR EXAMPLE 77

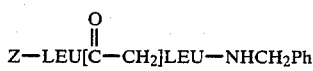

(0.75 g), benzylamine (0.21 g), and hydroxybenzotriazole (0.27 g)) were stirred together in dimethylformamide (30 ml) and cooled to 0°. Dicyclohexylcarbodiimide (0.41 g) was added and the mixture allowed to warm slowly to 25°. The mixture was stirred for 24 hours and then filtered. The filtrate was taken up in ethyl acetate and washed with water, sodium bicarbonate, and brine. The organic phase was dried over sodium sulfite, filtered, and evaporated to give 0.8 g of product.

(0.8 g) was dissolved in ethanol (15 ml) and cooled to 0°. Sodium borohydride (0.2 g) was added and the mixture allowed to warm to 25° and stirred for two hours. Acetic acid and water 1:1 were added and the mixture extracted with ethyl acetate and sodium bicarbonate. The organic phase was washed with brine, dried over sodium sulfate, filtered, and evaporated to give 0.8 g of product.

(0.8 g) was dissolved in methanol (15 ml) and palladium on carbon (20%) (0.1 g) added. The flask was flushed with hydrogen and stirred for three hours. The flask was then flushed with nitrogen and the mixture filtered. The solvent was evaporated to give 0.55 g of the desired product.

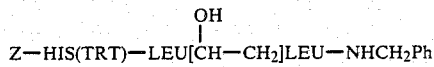

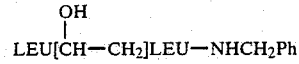

(0.55 g), Z-HIS(TRT) (0.87 g), and hydroxybenzotriazole (0.22 g) were stirred together in dimethylformamide (15 ml) and cooled to 0°. Dicyclohexylcarbodiimide (0.34 g) was added and the mixture allowed to slowly warm to 25° and stirred for 24 hours. The mixture was filtered and the filtrate extracted with ethyl acetate and water. The organic phase was washed with water, sodium bicarbonate, and brine. The organic phase was dried over sodium sulfate, filtered, and evaporated. The residue was eluted from silica gel with 1:1 ethyl acetate/hexane to give 0.9 g of product.

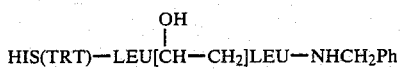

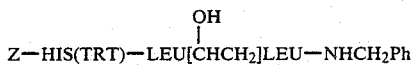

(0.9 g) was dissolved in methanol (20 ml) and palladium on carbon (20%) (0.2 g) added. The flask was flushed with hydrogen and stirred for four hours. The flask was then flushed with nitrogen and the mixture filtered. The solvent was evaporated to give 0.7 g of product.

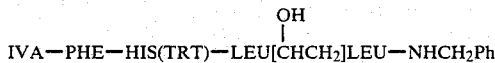

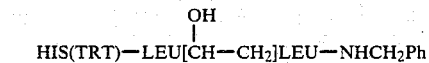

(0.7 g), IVA-PHE (0.25 g), and hydroxybenzotriazole (0.14 g) were stirred together in dimethylformamide (15 ml) and cooled to 0°. Dicyclohexylcarbodiimide (0.21 g) was added and the mixture allowed to warm to 25° slowly. The mixture was stirred for 24 hours and then filtered. The filtrate was extracted with ethyl acetate and water. The organic phase was washed with water, sodium bicarbonate, and brine. The organic phase was dried over sodium sulfate, filtered, and evaporated. The residue was eluted from silica gel with 3:1 ethyl acetate/hexane to give 0.9 g of product.

INTERMEDIATES FOR EXAMPLES 27, 28, 78, 79, and 80

BOC-CYCLOHEXYLALA (20 g) was dissolved in ethyl acetate (200 ml) and cooled to −20°. N-methyl piperidine (8.5 ml) was added, followed by a dropwise addition of isobutyl chloroformate (9.56 ml). The mixture was stirred for 10 minutes and then filtered under nitrogen into a cold flask. Diazomethane (8 g) in ether was added and the mixture allowed to stand at 2° overnight. Nitrogen was bubbled through the solution to remove any excess diazomethane. The solvent was washed with water, sodium bicarbonate, and brine. The organic phase was dried over sodium sulfate, filtered, and evaporated. The residue was recrystallized from hexane to give 13 g of product, mp 93°–94°.

This is called carbamic acid, [1-(cyclohexylmethyl)-3-diazo-2-oxo-propyl]-,1,1-dimethylethyl ester, (S).

Analysis: Calcd.: C, 60.99; H, 8.53; N, 14.23. Found: C, 61.02; H, 8.75; N, 14.10.

$[\alpha]_D^{23} = -60.8°$ (C, 1.0, EtOH).

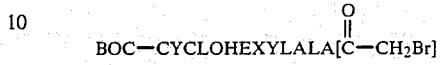

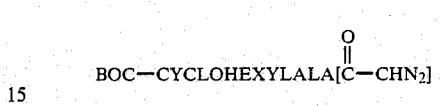

(10 g) was dissolved in ether (300 ml) and cooled to −20°. Gaseous hydrogen bromide was bubbled into the ether solution until the pH measured 1. The mixture was washed with 1N citric acid, sodium bicarbonate, and brine. The organic layer was dried over sodium sulfate, filtered, and evaporated. The residue was recrystallized from hexane to give 10.2 g of product, mp 89°–90°.

This is called carbamic acid, [3-bromo-1-(cyclohexylmethyl)-2-oxo-propyl]-,1,1-dimethylethyl ester, (S).

Analysis: Calcd.: C, 51.73; H, 7.52; N, 4.02. Found: C, 52.03; H, 7.51; N, 3.87.

$[\alpha]_D^{23} = -61.6°$ (C, 1.29, EtOH).

Sodium hydride (0.83 g) (60%) was washed with hexane and then suspended in THF (30 ml). Dibenzyl malonate (5 g) in THF (40 ml) was added slowly. The mixture was stirred for one hour at 25° and then cooled to 0°.

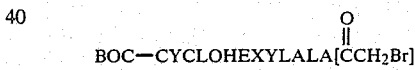

(6 g) in THF (20 ml) was added. The mixture was stirred for 0.5 hours at 0°, then warmed to 25° and stirred for one hour. The mixture was extracted with 1N citric acid and ether. The organic layer was washed with sodium bicarbonate and brine. The extract was dried over sodium sulfate, filtered and evaporated. The residue was eluted from silica gel with 25% ether/hexane to give 9 g of product.

Analysis: Calcd.: C, 69.07; H, 7.49; N, 27.57. Found: C, 69.73; H, 7.61; N, 2.62.

Sodium hydride (0.37 g) (60%) was washed with hexane and then suspended in dimethylsulfoxide (20 ml).

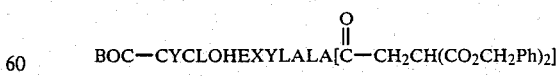

(5.1 g) was added and the mixture stirred for one hour at 25°. Isobutyl iodide (2.1 ml) was added and the mixture stirred for 24 hours. The mixture was extracted with ethyl acetate and 1N citric acid. The organic layer was washed with sodium bicarbonate and brine. The extract was dried over sodium sulfate, filtered and evaporated. The residue was eluted from silica gel with 15% ether/hexane. Combining the fractions with CH$_2$Cl$_2$ gave 5 g of product.

This is called propanedioic acid, [4-cyclohexyl-3-[[(1,1-dimethylethoxy)carbonyl]amino]-2-oxobutyl], bis(phenylmethyl)ester, (S).

Calcd. for C$_{36}$H$_{49}$NO$_7$·0.25CH$_2$Cl$_2$ (MW 629.00): C, 69.22; H, 7.93; N, 2.23. Found: C, 69.16; H, 7.71; N, 2.16. [α]$_D^{23}$ = −24.5° (C, 1.12, EtOH).

(3 g) was dissolved in methanol (15 ml). Palladium on carbon (0.3 g) was added and the flask flushed with hydrogen. The mixture was stirred for two hours and then flushed with nitrogen. The mixture was filtered and the solvent evaporated. The residue was dissolved in toluene and heated to reflux for four hours. The mixture was cooled and the solvent evaporated to give 1.9 g of product.

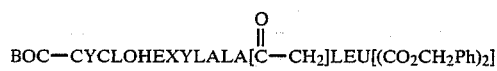

(6.3 g) was dissolved in methanol (70 ml). Palladium on carbon (20%) (0.5 g) was added and the flask flushed with hydrogen. The mixture was stirred for three hours and the flask then flushed with nitrogen. The solvent was evaporated and the residue dissolved in toluene (50 ml). The mixture was heated to reflux for two hours. The solvent was evaporated to give 4.5 g of product. The product was crystallized from hexane to give a solid, mp 107°–110°.

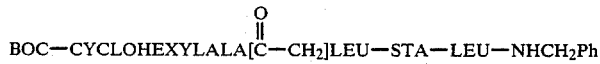

(0.4 g), STA-LEU-NHCH$_2$Ph·HCl (0.43 g), triethylamine (0.15 ml), and hydroxybenzotriazole (0.14 g) were stirred together in dimethylformamide (20 ml). The mixture was cooled to 0° and DCC (0.22 g) added. The mixture was allowed to slowly warm to 25° and stir for 24 hours. The mixture was filtered and the filtrate extracted with ethyl acetate and water. The organic phase was washed with water, sodium bicarbonate, and brine. The extract was dried over sodium sulfate, filtered and evaporated. The residue was eluted on silica gel with 1:1 ethyl acetate/hexane to give 0.68 g of product.

Analysis: Calcd.: C, 67.89; H, 9.50; N, 7.54. Found: C, 67.66; H, 9.32; N, 7.81.

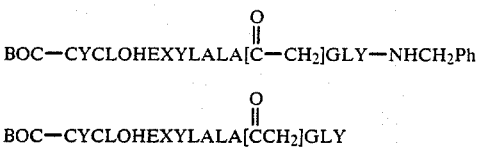

(1.2 g), benzylamine (0.32 g), and hydroxybenzotriazole (0.4 g) were stirred together in dimethylformamide (20 ml). The mixture was cooled to 0° and dicyclohexylcarbodiimide (0.62 g) added. The mixture was allowed to warm to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with 4:1 hexane/ethyl acetate to give 1 g of product.

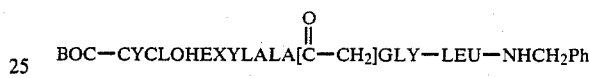

(0.8 g), LEU-NHCH$_2$Ph·HCl (0.52 g), triethylamine (0.28 ml), and hydroxybenzotriazole (0.27 g) were stirred together in dimethylformamide (20 ml). The mixture was cooled to 0° and dicyclohexylcarbodiimide (0.41 g) added. The mixture was allowed to slowly warm to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted on silica gel with 4:1 hexane/ethyl acetate to give 0.9 g of product.

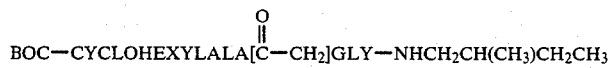

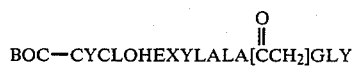

(1.9 g), 2-methylbutylamine (0.69 ml), and hydroxybenzotriazole (0.78 g) were stirred together in dimethylformamide (15 ml) and cooled to 0°. Dicyclohexylcarbodiimide (1.19 g) was added and the mixture allowed to warm to 25° and stir overnight. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 1:1 ether/hexane to give 1.5 g of product.

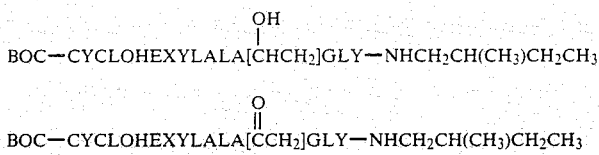

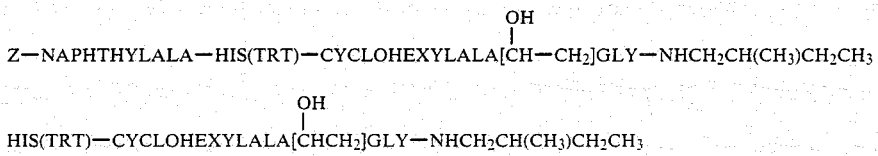

(1.5 gm) was dissolved in ethanol (15 ml) and cooled to 0°. Sodium borohydride (0.14 g) was added and the mixture allowed to warm to 25° and stir for three hours. Acetic acid and water 1:1 was added and the solvent evaporated. The residue was extracted with ethyl acetate and sodium bicarbonate. The extract was washed with brine, dried over sodium sulfate, filtered, and evaporated. The residue was eluted from silica gel with 1:1 ethyl acetate/hexane to give 1.25 g of product, mp 115°–125°.

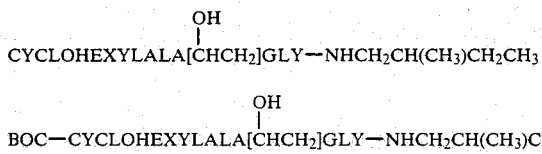

(1.25 g) was dissolved in dichloromethane (20 ml) and trifluoroacetic acid (4 ml) added. The mixture was stirred for two hours at 25° and then the solvent was evaporated. The residue was extracted with ethyl acetate and sodium carbonate. The organic phase was washed with brine, dried over sodium sulfate, filtered, and evaporated to give 1.0 g of product.

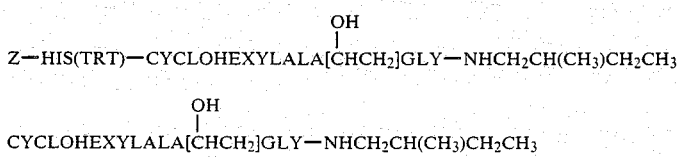

(1.0 g), Z-HIS(TRT) (1.67 g), and hydroxybenzo triazole (0.42 g) were stirred together in dimethylformamide (15 ml) and cooled to 0°. Dicyclohexylcarbodiimide (0.65 g) was added and the mixture allowed to warm to 25° slowly. The mixture was stirred for 24 hours and then filtered. The filtrate was extracted with ethyl acetate and water. The organic phase was washed with water, sodium bicarbonate, and brine. The extract was dried over sodium sulfate, filtered, and evaporated. The residue was eluted from silica gel with ethyl acetate to give 1.9 g of product.

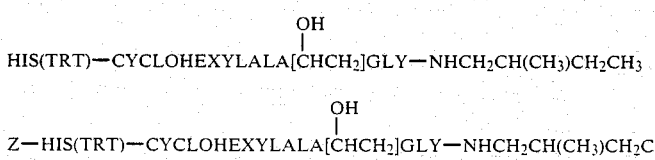

(1.9 g) was dissolved in methanol and palladium on carbon (20%) (0.2 g) added. The flask was flushed with hydrogen. The mixture was stirred for seven hours at 25°. The flask was flushed with nitrogen and the mixture filtered. The solvent was evaporated to give 1.6 g of product.

(0.8 g), Z-NAPHTHYLALA (0.42 g), and hydroxybenzotriazole (0.16 g) were stirred together in dimethylformamide (20 ml) and cooled to 0°. Dicyclohexylcarbodiimide (0.24 g) was added and the mixture allowed to slowly warm to 25°. The mixture was stirred for 24 hours and then filtered. The filtrate was extracted with ethyl acetate and water. The organic phase was washed with water, sodium bicarbonate, and brine. The extract was dried over sodium sulfate, filtered, and evaporated. The residue was eluted from silica gel with ethyl acetate to give 0.8 g of product.

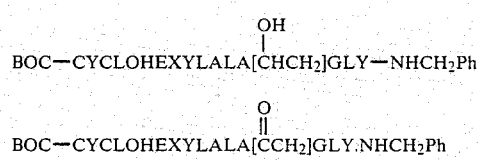

(1.5 g) was dissolved in ethanol (20 ml) and cooled to 0°. Sodium borohydride (0.14 g) was added and the mixture stirred for two hours at 25°. Acetic acid and water 1:1 was added to quench the reaction and the solvent evaporated. The residue was extracted with ethyl acetate and sodium bicarbonate. The organic layer was washed with brine, dried over sodium sulfate, filtered, and evaporated to give 1.4 g of product.

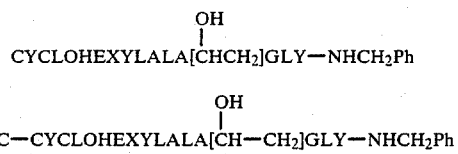

CYCLOHEXYLALA[CHCH₂]GLY—NHCH₂Ph (with OH on first CH)

BOC—CYCLOHEXYLALA[CH—CH₂]GLY—NHCH₂Ph (with OH)

(1.4 g) was dissolved in dichloromethane (15 ml). Trifluoro acetic acid (2 ml) was added and the mixture stirred at 25° for two hours. The solvent was evaporated and the residue extracted with sodium bicarbonate and ethyl acetate. The organic layer was washed with brine, dried over sodium sulfate, filtered, and evaporated to give 1.1 g of product.

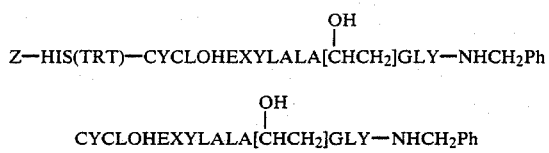

Z—HIS(TRT)—CYCLOHEXYLALA[CHCH₂]GLY—NHCH₂Ph (with OH)

CYCLOHEXYLALA[CHCH₂]GLY—NHCH₂Ph (with OH)

(1.1 g), Z-HIS(TRT) (1.78 g), and hydroxybenzotriazole (0.5 g) were stirred together in dimethylformamide (20 ml). The mixture was cooled to 0° and dicyclohexylcarbodiimide (0.7 g) added. The mixture was allowed to warm to 25° slowly and was then stirred for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with ethyl acetate to give 1.6 g of product.

HIS(TRT)—CYCLOHEXYLALA[CHCH₂]GLY—NHCH₂Ph (with OH)

Z—HIS(TRT)—CYCLOHEXYLALA[CHCH₂]GLY—NHCH₂Ph (with OH)

(1.6 g) was dissolved in methanol (20 ml) and palladium on carbon (20%) (0.2 g) added. The flask was flushed with hydrogen and stirred for four hours. The flask was then flushed with nitrogen and the mixture filtered. The solvent was evaporated to give 1.3 g of product.

IVA—PHE—HIS(TRT)—CYCLOHEXYLALA[CHCH₂]GLY—NHCH₂Ph (with OH)

HIS(TRT)—CYCLOHEXYLALA[CHCH₂]GLY—NHCH₂Ph (with OH)

(0.8 g), IVA-PHE (0.24 g), and hydroxybenzotriazole (0.13 g) were stirred together in dimethylformamide (10 ml). The mixture was cooled to 0° and dicyclohexylcarbodiimide (0.2 g) added. The mixture was allowed to warm to 25° slowly and was stirred overnight. The mixture was filtered and the filtrate extracted with ethyl acetate and water. The organic layer was washed with water, sodium bicarbonate and brine. The extract was dried over sodium sulfate, filtered and evaporated. The residue was eluted from silica gel with 10% methanol/ethyl acetate to give 0.5 g of product.

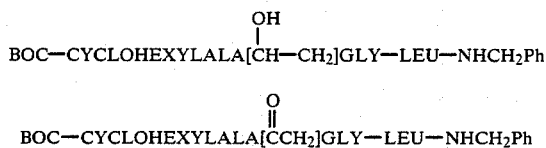

BOC—CYCLOHEXYLALA[CH—CH₂]GLY—LEU—NHCH₂Ph (with OH)

BOC—CYCLOHEXYLALA[CCH₂]GLY—LEU—NHCH₂Ph (with =O)

(0.9 g) was dissolved in ethanol (20 ml) and cooled to 0°. Sodium borohydride (0.8 g) was added and the mixture was allowed to warm to 25° and stir for two hours. Acetic acid and water 1:1 was added and the solvent evaporated. The residue was extracted with ethyl acetate and sodium bicarbonate. The organic layer was washed with brine, dried over sodium sulfate, filtered, and evaporated to give 0.8 g of product.

CYCLOHEXYLALA[CH—CH₂]GLY—LEU—NHCH₂Ph (with OH)

BOC—CYCLOHEXYLALA[CHCH₂]GLY—LEU—NHCH₂Ph (with OH)

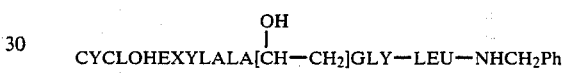

(0.8 g) was dissolved in dichloromethane (20 ml) and trifluoroacetic acid (2 ml) was added. The mixture was stirred at 25° for two hours. The solvent was evaporated and the residue extracted with ethyl acetate and sodium carbonate. The organic layer was washed with brine, dried over sodium sulfate, filtered, and evaporated to give 0.6 g of product.

Z—HIS(TRT)—CYCLOHEXYLALA[CH—CH₂]GLY—LEU—NHCH₂Ph (with OH)

CYCLOHEXYLALA[CHCH₂]GLY—LEU—NHCH₂Ph (with OH)

(0.8 g), Z-HIS(TRT) (1.6 g), and hydroxybenzotriazole (0.27 g) were stirred together in dimethylformamide (15 ml) and cooled to 0°. Dicyclohexylcarbodiimide (0.41 g) was added and the mixture allowed to slowly warm to 25° and stir for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with ethyl acetate to give 0.5 g of the desired product.

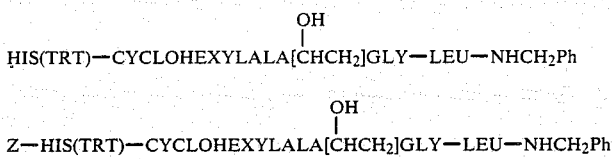

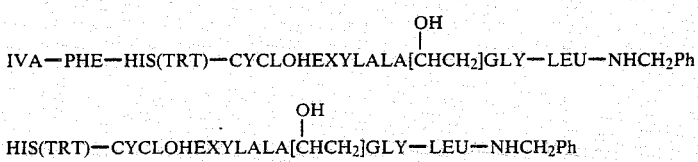

(0.5 g) was dissolved in methanol (15 ml) and palladium on carbon (20%) (0.1 g) was added. The flask was flushed with hydrogen and the mixture stirred for three hours. The flask was flushed with nitrogen and the mixture filtered. The solvent was evaporated to give 0.4 g of product.

IVA—PHE—HIS(TRT)—CYCLOHEXYLALA[CHCH$_2$]GLY—LEU—NHCH$_2$Ph
(with OH on the CH)

(0.4 g), IVA-PHE (0.14 g), and hydroxybenzotriazole (0.07 g) were stirred together in dimethylformamide (10 ml). The mixture was cooled to 0° and dicyclohexylcarbodiimide added (0.11 g). The mixture was allowed to slowly warm to 25° and stir overnight. The mixture was filtered and the filtrate extracted with ethyl acetate and water. The organic layer was washed with water, sodium bicarbonate, and brine. The extract was dried over sodium sulfate, filtered, and evaporated. The residue was eluted on silica gel with ethyl acetate to give 0.4 g of product.

INTERMEDIATES FOR EXAMPLE 30 AND 31

A solution of 27.86 g BOC-PHE in 250 ml ethyl acetate was cooled to −35°. To the solution was added 12.1 ml N-methylpiperidine, followed by 13.6 ml isobutyl chloroformate. After stirring four minutes at −30°, the mixture was filtered into a cold flask equipped with magnetic stirring.

To the mixture at −50° was added an alcohol-free solution of diazomethane in 500 ml ethyl ether, which was prepared from 52 g N-methyl-N-nitroso-p-toluenesulfonamide by the procedure described in Aldrichimica Acta, 16(1), 3 (1983). After warming to 4° overnight, the solution was washed with saturated sodium bicarbonate solution, saturated sodium chloride solution and dried over anhydrous magnesium sulfate. The suspension was filtered, stripped to an orange oil, and taken up in hexane, giving a yellow solid, 18.52 g, 60.9% yield. Spectral and elemental analyses verify the structure to be the desired product, $[\alpha]_D^{23} = -35.5°$ (C, 1.10, MeOH).

A solution of 17.54 g

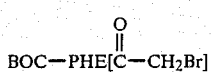

in 600 ml ethyl ether was cooled to −20°. From a separate flask, a solution of anhydrous hydrogen bromide gas in ethyl ether was added, until the pH to wet indicator paper remained at 2.5 to 3.0. The mixture was then stirred at −20° to −10° until the starting material was consumed, as indicated by thin-layer chromatography.

Saturated sodium bicarbonate solution was added until the pH was basic to litmus and the organic phase was then washed with 1N citric acid, saturated sodium chloride solution, saturated sodium bicarbonate solution, and saturated sodium chloride solution. The organic phase was dried over anhydrous magnesium sulfate, filtered, and stripped to an oil which gave a crystalline solid upon suspension in hexane, 16.55 g, 79.7% yield, mp 102°–103°. Spectral and elemental analyses verify the structure to be the desired product, $[\alpha]_D^{23} = -45.7°$ (C, 1.02, MeOH).

BOC-PHE[COCH$_2$]GLY[(CO$_2$CH$_2$Ph)$_2$]

0.54 g NaH (60% emulsion in oil) was washed with dry tetrahydrofuran, resuspended in 25 ml tetrahydrofuran and added to 3.39 ml dibenzyl malonate. After 30 minutes, the solution was cooled to 0° and a solution of 4.55 g

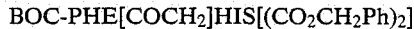

in 25 ml dimethyl formamide at 0° added. The mixture was warmed to 25° over 3.5 hours, and the solvent removed in vacuo. The residue was dissolved in ethyl ether, washed with 1N citric acid, saturated sodium chloride solution, saturated sodium bicarbonate solution, saturated sodium chloride solution, and dried over anhydrous magnesium sulfate. The suspension was filtered, stripped of solvent, and crystallized from ethyl ether/cyclohexane, giving a white solid upon drying in vacuo, 5.01 g, mp 82°–85°. Spectral and elemental analyses confirm the structure to be the desired product, $[\alpha]_D^{23} = -26.7°$ (C, 1.10, MeOH).

BOC-PHE[COCH$_2$]HIS[(CO$_2$CH$_2$Ph)$_2$]

1.0 g sodium hydride (60% emulsion in oil) was washed with dry tetrahydrofuran, resuspended in 20 ml dry dimethyl sulfoxide and heated to 70° for 1.5 hours, giving solution. The mixture was cooled to 0° and diluted with 40 ml tetrahydrofuran. A cooled solution of BOC-PHE[COCH$_2$]GLY[(CO$_2$CH$_2$Ph)$_2$] (13.72 g) in 80 ml dimethyl sulfoxide was added and the mixture stirred at 0° for 15 minutes. 1.92 g of 5-chloromethylimadazole hydrochloride [J. Am. Chem. Soc. 71, 2801 (1949)] was dissolved in 15 ml dimethyl sulfoxide and the solution added to the above mixture. The mixture was stirred and warmed to 25° over four hours, after which the tetrahydrofuran was removed in vacuo. The remaining solution was partitioned between ethyl ether and water, and the ether phase separated, extracted with 1N citric acid, saturated sodium chloride solution, saturated sodium bicarbonate solution, and saturated sodium chloride solution. The ether phase was dried over anhydrous magnesium sulfate, filtered, stripped to an oil, and chromatographed on silica gel, eluting with 1% methanol in chloroform. The fractions containing the desired product were stripped to an oil, 5.85 g, 85% yield. Spectral and elemental analyses confirm the structure as the desired product, $[\alpha]_D^{23} = -23.6°$ (C, 1.04, MeOH).

BOC-PHE[COCH$_2$]HIS(TRT)[(CO$_2$CH$_2$Ph)$_2$]

4.85 g BOC-PHE[COCH$_2$]HIS[(CO$_2$CH$_2$Ph)$_2$] was dissolved in 150 ml methylene chloride along with 2.3 g triphenylmethyl chloride and 1.2 ml triethylamine. After stirring at 23° for two hours, the solvent was removed in vacuo and the residue dissolved in ethyl acetate. The solution was washed with 1N citric acid, saturated sodium chloride solution, saturated sodium bicarbonate solution, and saturated sodium chloride solution, followed by drying over anhydrous magnesium sulfate. The suspension was filtered and stripped to a foam which was chromatographed on 500 g silica gel, eluting with a mixture of 75% hexane and 25% ethyl acetate. The material was recovered as a glass by evaporating the fractions containing the desired product in vacuo, giving 7.06 g, 100% yield of an oil. Spectroscopic and elemental analyses confirm the structure to be the desired product, $[\alpha]_D^{23} = -19.6°$ (C, 1.13, MeOH).

BOC-PHE[COCH$_2$]HIS(TRT)[(CO$_2$H)$_2$]

5.24 g BOC-PHE[COCH$_2$]HIS(TRT)[(CO$_2$CH$_2$Ph)$_2$] was dissolved in 100 ml methanol and purged with argon gas. 20% palladium on charcoal, 0.17 g, was added, followed by purging with hydrogen gas over 1.5 hours. Thin layer chromatography indicated complete consumption of starting material. The mixture was filtered and stripped of solvent to a foam, 4.05 g, 97% yield. The material was judged to be sufficiently pure by thin layer chromatography to be used in subsequent reactions.

BOC-PHE[COCH$_2$]HIS(TRT)

4.05 g BOC-PHE[COCH$_2$]HIS(TRT)[(CO$_2$H)$_2$] was suspended in 100 ml toluene and heated to reflux for 15 minutes. The mixture was cooled to 25° and stripped to a foam, 3.92 g, which was chromatographed on 100 g silica gel, eluting with 1% methanol in chloroform. The appropriate fractions were combined and stripped to a foam, 2.89 g, 74% yield which crystallized from ethyl ether and hexane, giving a white solid, 2.49 g, 64% yield. Spectral and elemental analyses verify the structure to be the desired product, $[\alpha]_D^{23} = -1.9°$ (C, 1.09, MeOH).

BOC-PHE[COCH$_2$]HIS(TRT)STA-LEU-NHCH$_2$Ph 2.19 g of BOC-PHE[COCH$_2$]HIS(TRT) was added to 0.49 g 1-hydroxybenzotriazole monohydrate which was dissolved in 2 ml dimethylformamide, followed by addition of 25 ml methylene chloride. After cooling to $-5°$, a cold solution of 0.74 g dicyclohexylcarbodiimide in 5 ml methylene chloride was added. This was followed by the addition of a solution of STA-LEU-NHCH$_2$Ph.HCl (1.41 g), in a mixture of 15 ml methylene chloride, 4 ml dimethylformamide, and 0.55 ml triethylamine. The mixture was stirred and allowed to warm to 25° overnight. The mixture was then filtered and stripped and the residue dissolved in ethyl acetate. The solution was washed with 1N citric acid, saturated sodium chloride solution, saturated sodium bicarbonate solution, and saturated sodium chloride solution. The organic phase was dried over anhydrous magnesium sulfate, filtered, and stripped to a foam, which was chromatographed on silica gel, eluting with 0.5% methanol in chloroform. The fractions containing the least polar (faster) isomer were combined and stripped to a solid, 1.10 g. NMR and mass spectral data confirmed the structure. The material was used without further purification in subsequent synthetic steps.

BOC-PHE[COCH$_2$]HIS(TRT)-STA-LEU-NHCH$_2$Ph

The fractions containing the more polar (slower moving) component were combined from the previously described chromatography of BOC-PHE[COCH$_2$]HIS(TRT)-STA-LEU-NHCH$_2$Ph and stripped in vacuo to a solid, 1.17 g. NMR and mass spectral data confirm the material to be the indicated structure, with minor contamination from the faster moving isomer. The material was used in the next synthetic step without further purification.

BOC-PHE[CHOHCH$_2$]HIS(TRT)-STA-LEU-NHCH$_2$Ph 1.05 g of BOC-PHE[COCH$_2$]HIS(TRT)-STA-LEU-NHCH$_2$Ph, (fast isomer) was dissolved in 20 ml dry absolute ethanol. To the solution was added 0.30 g sodium borohydride, followed by stirring at 25° for six hours. The mixture was cooled to 5° and the pH adjusted to 5.5 by addition of glacial acetic acid. The solution was stripped and the residue taken up into ethyl acetate and filtered. The filtrate was washed with 1N citric acid, saturated sodium chloride solution, followed by drying over anhydrous magnesium sulfate. The suspension was filtered, stripped to a solid, and chromatographed on 50 g silica gel, eluting with a gradient of 0.5% methanol to 2% methanol in chloroform. The appropriate fractions were combined and stripped to a white solid, 0.92 g, 87% yield. Mass spectral analysis confirmed the product to be BOC-PHE[CHOHCH$_2$]HIS(TRT)-STA-LEU-NHCH$_2$Ph. The product was used in subsequent steps without further purification.

BOC-PHE[CHOHCH$_2$]HIS(TRT)-STA-LEU-NHCH$_2$Ph 1.14 g of BOC-PHE[COCH$_2$]HIS(TRT)-STA-LEU-NHCH$_2$Ph, (slow isomer) was treated in a manner identical to that described for the fast isomer, giving the product as a white foam, 1.10 g. Mass spectral analysis confirms the structure as BOC-PHE[CHOHCH$_2$]HIS(TRT)-STA-LEU-NHCH$_2$Ph. The product was used without further purification in the next step.

INTERMEDIATE FOR EXAMPLE 35
BOC-PHE[CH₂CH₂]GLY

A solution of 1.11 g (3.6 mmole) of [S-(E)]-5-[[(1,1-dimethylethoxy)carbonyl]amino]-6-phenyl-3-hexenoic acid [J. Chem. Soc. 799 (1980)] in 100 ml of 2-propanol with 0.1 g of 10% palladium on charcoal as catalyst was reduced at 20°, 51 psi. The solution was then filtered and the solvent removed under reduced pressure to give a solid. Recrystallization from methanol-water gave 450 mg of pure product, [S]-5-[[(1,1-dimethylethoxy)carbonyl]amino]-6-phenylhexanoic acid, mp 102°–105°, $[\alpha]_D^{23} = +1.4°$ (C, 0.58, CH₃OH).

Calcd. for $C_{17}H_{25}NO_4$ (MW 307.38): C, 66.42; H, 8.20; N, 4.56. Found: C, 67.07; H, 8.06; N, 4.56.

The structure was also comfirmed by NMR and MS spectroscopy.

INTERMEDIATES FOR EXAMPLE 37
S-2-Amino-3-phenylpropanethiol

A solution of 9.0 g H₂S gas in 250 ml EtOH at −78° was treated dropwise with 9.33 g of S-2-benzylaziridine. The solution was allowed to warm to room temperature and the solvent removed under reduced pressure. There was obtained 11.7 g (100% yield) of a white, crystalline solid, $[\alpha]_D^{23} = +97.9°$ (C, 0.79, CH₃OH).

PHE[CH₂S]PHE-O-t-Bu

A solution of 3.0 g S-2-amino-3-phenylpropanethiol in 300 ml of liq. NH₃ was treated dropwise with 5.11 g of R,S-t-butyl 2-bromo-3-phenylpropionate. After stirring overnight and letting the NH₃ evaporate, the residue was taken up in ether and washed with Na₂CO₃ solution. After drying over MgSO₄, the solvent was removed under reduced pressure leaving an oil. Chromatography on silica gel, eluting with CH₂Cl₂/MeOH (97/3) gave 5.43 g (82% yield) of the product as a light yellow oil, $[\alpha]_D^{23} = +29.3°$ (C, 0.58, CH₃OH).

IVA-PHE[CH₂S]PHE-O-t-Bu

A solution of 2.5 g PHE[CH₂S]PHE-O-t-Bu in 50 ml CH₂Cl₂ was treated with 2.0 ml Et₃N and cooled to 0°. 0.82 ml of isovaleryl chloride was then added dropwise and the solution left stirring overnight. The solution was then washed with Na₂CO₃ solution, 10% citric acid, and water. After drying over MgSO₄, the solvent was removed under reduced pressure leaving an oil. Chromatography on silica gel, eluting with CH₂Cl₂ gave 1.81 g (59% yield) of an oil. $[\alpha]_D^{23} = +35.7°$ (C, 0.54, CH₃OH).

IVA-PHE[CH₂S]PHE 1.56 g of IVA-PHE[CH₂S]PHE-O-t-Bu was added to 10 ml of trifluoroacetic acid and the solution left standing at room temperature overnight. The solvent was removed under reduced pressure and the residue taken up in ether. After extracting with Na₂CO₃ solution, and washing with diethyl ether, the extract was acidified with citric acid and extracted with ethyl acetate. Drying and removal of the solvent under reduced pressure left an oil. Chromatography on silica gel, eluting with CH₂Cl₂/MeOH (97/3) gave 0.63 g (57% yield) of the product.

INTERMEDIATE FOR EXAMPLE 40
IVA-PHE[CH₂SO]PHE

A solution of 0.49 g IVA-PHE[CH₂S]PHE in 20 ml MeOH was treated with 11 ml of 0.5M NaIO₄ and stirred at room temperature for two hours. The solution was filtered and the solvent removed under reduced pressure. The residue was taken up in ETOAc, washed with saturated NaHCO₃, dried over MgSO₄, and the solvent removed under pressure leaving 0.36 g (71% yield) of the product as a white solid.

INTERMEDIATES FOR EXAMPLE 41
PHE[CH₂S]PHE-OCH₃

To a solution of 100 ml MeOH saturated with HCl gas was added 6.8 g of PHE[CH₂S]PHE-O-t-Bu and the solution left standing for two days. The solvent was removed under reduced pressure and ether was added to the residue giving 6.0 g (99.7%) of the product as the hydrochloride.

BOC-PHE[CH₂S]PHE-OCH₃

A solution of 4.0 g PHE[CH₂S]PHE-OCH₃·HCl in 80 ml of a 1:1 mixture of H₂O/dioxane was cooled to 0°, excess NaHCO₃ added, and the mixture then treated with 2.8 g of di-t-butyldicarbonate. After standing at 5° overnight, the solvent was removed under reduced pressure and the residue taken up in ethyl acetate. The ethyl acetate was dried over MgSO₄ and the solvent removed under reduced pressure leaving an oil. After chromatography on silica gel, eluting with CH₂Cl₂/MeOH (98/2) there was obtained 4.59 g (98% yield) of the product as an oil.

BOC-PHE[CH₂S]PHE

A solution of 4.04 g BOC-PHE[CH₂S]PHE-OCH₃ in 40 ml of MeOH was treated with 10 ml of 1N NaOH and stirred at room temperature overnight. The solvent was removed under reduced pressure and the residue taken up in H₂O and washed with EtOAc. The aqueous layer was acidified with citric acid and extracted with EtOAc. After drying over MgSO₄ and removal of the solvent under reduced pressure, the residue was chromatographed on silica gel, eluting with CH₂Cl₂/MeOH (97.3). There was obtained 2.97 g (76% yield) of the product as an oil, $[\alpha]_D^{23} = +13.2°$ (C, 0.63, MeOH).

BOC-PHE[CH₂SO]PHE

A solution of 1.36 g of BOC-PHE[CH₂S]PHE in 15 ml MeOH was treated with 9 ml of 0.5M NaIO₄ and allowed to stir at room temperature for two hours, and was then warmed to 50° for 0.5 hours. The solution was filtered and the solvent removed under reduced pressure. The residue was taken up in EtOAc, washed with NaHSO₃ solution, dried over MgSO₄, and the solvent removed under reduced pressure. Treating the residue with a small amount of EtOAc gave 0.51 g (36% yield) of the product as a white solid.

INTERMEDIATES FOR EXAMPLE 44

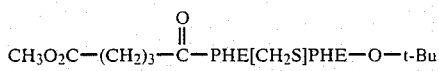

A solution of 0.5 g (3.4 mmole) of the monomethyl ester of glutaric acid, 1.38 g (3.7 mmole) of PHE[CH2S]PHE-O-t-Bu, and 0.5 g (3.7 mmole) of hydroxybenzotriazole in 60 ml of dichloromethane was cooled to 0° and 0.76 g (3.7 mmole) of dicyclohexylcarbodiimide added. After stirring at room temperature for two days, the mixture was filtered, the solvent evaporated under reduced pressure and the residue taken up in EtOAc. The solution was washed with Na2CO3 solution, citric acid solution, and then dried over MgSO4. Removal of the solvent under reduced pressure and chromatography of the residue on silica gel, eluting with CH2Cl2/MeOH (97/3) gave 1.46 g (80.7% yield) of the product as an oil which crystallized on standing.

Analysis: Calcd.: C, 67.30; H, 7.46; N, 2.80. Found: C, 67.14; H, 7.58; N, 2.90.

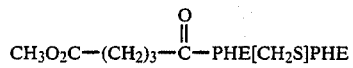

A solution of 1.11 g (2.2 mmole) of

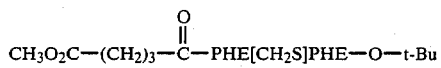

in 10 ml of trifluoroacetic acid was allowed to stir at room temperature for three hours, and the solvent then removed under reduced pressure. Ether was added and the solvent again removed under reduced pressure. The residue was then chromatographed on silica gel, eluting with CH2Cl2/MeOH (98.2). The crude product was sufficiently pure to use in the following step.

A solution of 1.0 g (2.3 mmole) of

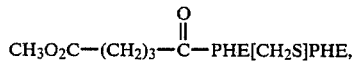

0.85 (2.1 mmole) of STA-LEU-NHCH2Ph, and 0.28 g (2.1 mmole) of hydroxybenzotriazole in 50 ml of a 1:1 mixture of CH2Cl2/DMF was cooled in ice and treated with 0.43 ml (3.1 mmole) of triethylamine, followed by 0.43 g (2.1 mmole) of dicyclohexylcarbodiimide. After stirring overnight at room temperature, the mixture was filtered and the solvent removed under reduced pressure. The residue was taken up in EtOAc and washed with Na2CO3 solution then a citric acid solution. The organic phase was dried over MgSO4 and the solvent removed under reduced pressure. The residue was chromatographed on silica gel, eluting with CH2Cl2/MeOH (98/2). There was obtained 1.1 g (60% yield) of product.

Analysis: Calcd.: C, 67.30; H, 7.78; N, 6.98. Found: C, 67.28; H, 7.87; N, 7.01.

INTERMEDIATE FOR EXAMPLE 46

A solution of 0.56 g of PHE[COCH2]GLY.HCl in 40 ml of a 1:1 mixture of H2O/dioxane was cooled to 0° and 0.75 ml Et3N added followed by 0.7 g of di-t-butyldicarbonate. After stirring at 0° for two hours, the solvent was removed under reduced pressure. The residue was taken up in H2O, acidified with citric acid, and extracted with EtOAc. The EtOAc was washed with saturated NaCl, dried over MgSO4, and the solvent removed under reduced pressure. The residue was chromatographed on silica gel, eluting with CH2Cl2/MeOH, (97.5/2.5). In this way there was obtained 0.46 g (66% yield) of the product as a white solid.

INTERMEDIATE FOR EXAMPLE 47

A suspension of 0.56 g PHE[COCH2]GLY.HCl in 40 ml of CH2Cl2 was cooled to 0° and 1.0 ml of Et3N added causing solution. 0.3 ml of isovaleryl chloride was added and the solution stirred at 0° for two hours. Citric acid was added and the CH2Cl2 layer separated. After drying over MgSO4 and removal of the solvent under reduced pressure, the residue was chromatographed on silica gel, eluting with CH2Cl2/MeOH (97.5/2.5). In this way there was obtained 0.45 g (68%) of the product as a white solid.

INTERMEDIATES FOR EXAMPLE 49

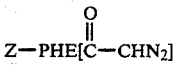

A solution of 24.06 g Z-PHE in 250 ml ethyl ether was cooled to −10° and 9.77 ml of N-methylpiperidine added. 10.42 ml isobutyl chloroformate was added with agitation, giving solution after ten minutes. To the mixture at 0° was added an alcohol-free solution of diazomethane in 400 ml ethyl ether, which was prepared from 43 g N-methyl-N-nitroso-p-toluenesulfonamide by the procedure described in Aldrichimica Acta, 16(1), 3 (1983).

After standing overnight at 4°, 30 ml ethyl acetate was added and the mixture stripped to an oil. The oil was taken up in 400 ml ethyl acetate, which was washed with saturated sodium bicarbonate solution, saturated sodium chloride solution, and dried over anhydrous magnesium sulfate. The suspension was filtered, stripped, and crystallized by the addition of ethyl ether and hexane. The mixture was filtered, washed with hexane, and dried in vacuo, giving a pale yellow solid, 19.87 g (77% yield), mp 84°–86°. Spectral and elemental analyses verify the structure. $[\alpha]_D^{23} = -40°$ (C, 1.25, MeOH).

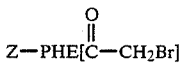

19.8 g

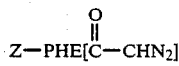

was dissolved in 1 l ethyl ether and cooled to −5°. To the solution was added a cooled solution of 7.12 g anhydrous hydrogen bromide gas in 200 ml ethyl ether over six minutes. The mixture was allowed to warm to room temperature over 30 minutes, followed by addition of saturated sodium bicarbonate solution to a pH of 8.0. Ethyl acetate was added as necessary to maintain solution of the product, and the phases were separated. The organic phase was washed with 1N citric acid, saturated sodium bicarbonate solution, and saturated sodium chloride solution. The organic phase was dried over anhydrous magnesium sulfate, filtered, and stripped to a paste, which was crystallized from ethyl ether and hexane to give a white solid, 21.40 g (93% yield), mp 99°–101°. Spectral and elemental analyses verify the structure. $[\alpha]_D^{23} = -48.0°$ (C, 1.04, MeOH).

Z-PHE[COCH2]GLY[(CO2-t-Bu)2]

2.13 g of a 60% NaH in oil suspension was added to a mixture of 150 ml dimethylformamide and 100 ml 1,3-dimethyl-3,4,5,6-tetrahydro-2(1H)-pyrimidone. The mixture was cooled to −5° and 12.01 ml di-t-butyl malonate added over 45 minutes, allowing the temperature to reach 5°, giving solution. The mixture was then cooled to 0°.

A solution of 20.1 g Z-PHE[COCH2Br] in 50 ml cold dimethylformamide was added, and the mixture allowed to warm to 25° over 3.5 hours. The dimethylformamide was stripped off and the mixture added to an equal volume of 1N citric acid. The mixture was extracted with ethyl ether, which was then washed with saturated sodium bicarbonate solution, then saturated sodium chloride. The organic phase was dried over anhydrous magnesium sulfate, filtered, and stripped to an oil, 29.87 g. The oil was chromatographed on 1 kg silica gel, eluting with an 80/20 mixture of hexane and ethyl acetate, giving the product as an oil, 18.93 g (69% yield). Spectral and elemental analyses confirm the structure. $[\alpha]_D^{23} = -23.7°$ (C, 0.78, MeOH).

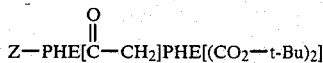

A solution of 7.64 g Z-PHE[COCH2]GLY[(CO2-t-Bu)2] in 100 ml dry tetrahydrofuran was added to 0.65 g 60% NaH in oil emulsion. The mixture was heated to reflux and cooled to 25° over 45 minutes, giving a clear yellow solution.

5.3 ml benzylbromide was added, followed by stirring for five hours at 25°. The mixture was filtered and stripped to an oil, which was dissolved in ethyl acetate. The solution was washed with 1N citric acid, saturated sodium bicarbonate solution, and saturated sodium chloride solution. After drying over anhydrous magnesium sulfate, the solution was filtered and stripped to an oil, 15.76 g. The oil was chromatographed on 900 g silica gel, eluting with a mixture of 80/20 hexane, ethyl acetate. The appropriate fractions were combined and stripped to an oil, which was dissolved in ethyl ether and stripped to a glass, 8.02 g (89% yield). Spectral and elemental analyses verify the structure. $[\alpha]_D^{23} = -28.0°$ (C, 0.55, MeOH).

Z-PHE[COCH2]PHE[(CO2H)2]

A solution of 7.75 g Z-PHE[COCH2]PHE[(CO2-t-Bu)2] in a mixture of 150 ml methylene chloride and 150 ml trifluoroacetic acid was stirred at 25° for two hours, then evaporated in vacuo. The residue was dissolved in methylene chloride and stripped to a white foam, 14.20 g. The foam was dissolved in ethyl acetate and washed with saturated sodium chloride solution, 1N citric acid, sodium chloride solution, and saturated sodium bicarbonate solution. The washed organic phase was stripped to 30 ml and added to 100 ml H2O. The pH was adjusted to 10.0 with 5% NaOH solution, the mixture agitated, and the phases separated. The extraction was repeated and the aqueous phases were combined and acidified to pH 1 with 12% HCl solution. This was extracted with ethyl acetate and the extract washed with saturated sodium chloride solution, dried over anhydrous magnesium sulfate, filtered, and stripped to a white foam, 5.60 g (89% yield). Spectral and elemental analyses verify the structure. $[\alpha]_D^{23} = -28.1°$ (C, 1.10, MeOH). The material is used in subsequent syntheses without further purification.

Z-PHE[COCH2]PHE 5.60 g Z-PHE[COCH2]PHE[(COOH)2] was dissolved in 150 ml toluene and refluxed for two hours. The toluene was stripped off and the residue chromatographed on 300 g silica gel, eluting with a gradient of 2% methanol increasing to 3% in chloroform. The appropriate fractions were combined and stripped to a white foam, 3.72 g (73% yield). The spectral and elemental analyses verify the structure. $[\alpha]_D^{23} = -31.9°$ (C, 0.93, MeOH).

INTERMEDIATES FOR EXAMPLE 50

N-(4-Methoxy-1,4-dioxobutyl)-L-phenylalanine, methyl ester

Triethylamine, 4.7 g (0.046 mole) was added to PHE-OCH3.HCl, 10 g (0.046 mole), in 200 ml of dichloromethane at 0°–5°. To this suspension was added 25.6 g (0.185 mole) of potassium carbonate followed by the dropwise addition of 3-carbomethoxypropionyl chloride, 15.3 g (0.1 mol). The mixture was stirred and allowed to reach room temperature overnight, filtered, the solvent evaporated in vacuo, and the residue was dissolved in 200 ml of dichloromethane and extracted successively with 100 ml of a 10% aqueous solution of hydrochloric acid, 100 ml of a 10% aqueous solution of sodium bicarbonate and 100 ml of a saturated aqueous solution of sodium chloride. The dichloromethane layer was separated, dried over sodium sulfate, evaporated in vacuo and the residue chromatographed using 300 g of silica gel and eluting with dichloromethane-methanol (98:2) to give N-(4-methoxy-1,4-dioxobutyl)-L-phenylalanine, methyl ester, 7.34 g; $[\alpha]_D^{25} = +9.84°$ (C, 0.63, methanol).

Calcd. for $C_{15}H_{19}NO_5$: C, 61.42; H, 6.53; N, 4.78. Found: C, 61.68; H, 6.53; N, 4.80.

3,6-Dioxo-2-(phenylmethyl)-4-piperidinecarboxylic acid, methyl ester: (DL-mixture at 2 position)

N-(4-Methoxy-1,4-dioxobutyl)-L-phenylalanine, methyl ester, 6.74 g (0.023 mole), was dissolved in 200 ml of dioxane, and 2.2 g (0.055 mole) of 60% sodium hydride in mineral oil dispersion slowly added. The mixture was refluxed for four hours, stirred, and allowed to reach room temperature overnight. The solvent was evaporated in vacuo and the residue dissolved in 100 ml of water, acidified with concentrated hydrochloric acid to pH 8.5 and extracted with 200 ml ethyl acetate. The ethyl acetate layer was separated, dried over sodium sulfate, evaporated in vacuo, and the residue chromatographed using 150 g of silica gel and eluting with 500 ml of dichloromethane-methanol (98:2) to give 3,6-dioxo-2-(phenylmethyl)-4-piperidinecarboxylic acid, methyl ester: (DL-mixture at 2 position), 5.1 g; mp 146°-147.5°.

Calcd. for $C_{14}H_{15}NO_4$: C, 64.36; H, 5.79; N, 5.36. Found: C, 64.25; H, 5.81; N, 5.34.

(±)-3,6-Dioxo-2-(phenylmethyl)-4-piperidinecarboxylic acid, phenylmethyl ester 3,6-Dioxo-2-(phenylmethyl)-4-piperidinecarboxylic acid, methyl ester, 4 g (0.015 mole) was added to benzyl alcohol, 8.1 g (0.075 mole), and the mixture warmed to 170° for three hours. The mixture was cooled and the residue chromatographed using 200 g of silica gel and eluting with 500 ml of dichloromethane-methanol (98:2) to give (±)-3,6-dioxo-2-(phenylmethyl)-4-piperidinecarboxylic acid, phenylmethyl ester, 4.5 g; mp. 119°-120.5°.

Calcd. for $C_{20}H_{19}NO_4$: C, 71.20; H, 5.68; N, 4.15. Found: C, 70.95; H, 5.72; N, 4.27.

(±)-6-(Phenylmethyl)-2,5-piperidinedione

A stirred suspension of (±)-3,6-dioxo-2-(phenylmethyl)-4-piperidinecarboxylic acid, phenylmethyl ester, 1.59 g (0.0047 mole) and 0.2 g of 20% palladium on carbon in 200 ml of ethyl acetate was exposed to hydrogen gas for 15 minutes, the suspension was purged with nitrogen gas, filtered, and the solvent evaporated in vacuo and the residue chromatographed using 100 g of silica gel and eluting with 200 ml of dichloromethane-methanol (98:2) and 200 ml of dichloromethane-methanol (97:3) to give (±)-6-(phenylmethyl)-2,5-piperidinedione, 0.8 g; mp 140°-141°.

Calcd. for $C_{12}H_{13}NO_2$: C, 70.91; H, 6.45; N, 6.89. Found: C, 71.24; H, 6.56; N, 6.93.

BOC-PHE[COCH$_2$]CH$_2$CO$_2$H

Di-tertiary-butyl dicarbonate, 1.94 g (0.009 mole), was added to a mixture of 0.87 g (0.0043 mole) of (±)-6-(phenylmethyl)-2,5-piperidinedione, 0.42 g (0.0042 mole) of triethylamine and 0.43 g (0.0035 mole) of 4-dimethylaminopiperidine in 200 ml dichloromethane at 0°-5°. The mixture was allowed to stand one hour and the solvent evaporated in vacuo and the residue chromatographed using 100 g on silica gel and eluting with hexane-diethyl ether (6:1) to give 1.02 g of the N-t-butyl ketolactam. The N-t-butyl ketolactam was added to 9.6 ml of 1N lithium hydroxide and stirred for two hours. The mixture was then neutralized with citric acid and extracted with 200 ml of dichloromethane. The dichloromethane layer was separated, dried over sodium sulfate, evaporated in vacuo, and the residue chromatographed using 100 g of silica gel and eluting with dichloromethane-methanol (95:5) to give BOC-PHE[COCH$_2$]CH$_2$CO$_2$H, 0.6 g.

Calcd. for $C_{17}H_{23}NO_5$: C, 63.53; H, 7.21; N, 4.36. Found: C, 63.60; H, 7.11; N, 4.44.

INTERMEDIATES FOR EXAMPLE 64

HIS(TRT)-OCH$_3$

N-Carbobenzyloxy-$\tau^{im}$-trityl histidine methyl ester (10 g) was dissolved in 100 ml of methanol and palladium on carbon (20%) (0.2 g) added. The flask was evacuated and then flushed with hydrogen from a balloon. The mixture was stirred for three hours, at 25°. The flask was evacuated and flushed with N$_2$. The mixture was filtered and the solvent evaporated under reduced pressure to give the product, 7.5 gms (100%), $\tau^{im}$trityl histidine, methyl ester.

BOC-PHE[CH$_2$NH]HIS(TRT)-OCH$_3$

Trityl histidine methyl ester (7.5 g) and BOC phenylalanine aldehyde (3.8 g) were mixed in methanol (200 ml). Molecular sieves (3 Å) (15 g) were added and the mixture stirred for 24 hours. Sodium cyanoborohydride (1 g) and citric acid (3.1 g) were added to the flask and the mixture stirred for 24 hours. The reaction was filtered and evaporated under reduced pressure. The residue was dissolved in ethyl acetate and extracted with 1N citric acid, saturated sodium bicarbonate solution, and saturated brine. The organic layer was dried over sodium sulfate, filtered, and evaporated. The residue was eluted from a column of silica gel with 1:1 ethyl acetate/hexane to give 5 g of the desired product.

L-Histidine, N-[2-[[(1,1-dimethylethoxy)carbonyl]amino]-3-phenylpropyl]-1-(triphenylmethyl)-, methyl ester, (S)-.

Calcd. for $C_{40}H_{43}N_4O_4.0.13C_4H_8O_2$ (MW 655.23): C, 74.27; H, 6.78; N, 8.55. Found: C, 74.07; H, 6.58; N, 8.51.

BOC-PHE[CH$_2$NZ]HIS(TRT)-OCH$_3$

BOC-PHE[CH$_2$NH]HIS(TRT)-OMe (3.2 g) was dissolved in chloroform (50 ml) and 4-dimethylaminopyridine (0.1 g) and N-benzyloxycarbonylsuccinimide (1.2 g) were added. The mixture was heated to reflux for 24 hours, and then cooled to 25°. The solvent was removed under reduced pressure and the residue dissolved in ethyl acetate. The solution was extracted with water, saturated sodium bicarbonate solution, and brine. The organic phase was dried over sodium sulphate then filtered and evaporated. The residue was eluted from silica gel with 1:1 ethyl acetate/hexane and the fractions combined using CH$_2$Cl$_2$ to give 1.2 g of the desired product.

Calcd. for $C_{48}H_{49}N_4O_6.0.1CH_2Cl_2.0.13C_4H_8O_2$ (MW 796.82): C, 73.28; H, 6.23; N, 7.03. Found: C, 73.23; H, 6.54; N, 7.08.

BOC-PHE[CH$_2$NZ]HIS(TRT)

BOC-PHE[CH$_2$NZ]HIS(TRT)-OMe (3.5 g) was dissolved in dioxane (50 ml) and the solution cooled to 0°. Sodium hydroxide (0.2 g in 20 ml of water) was added and the mixture allowed to warm to 25°. The mixture was stirred for two hours and then the dioxane evaporated. The concentrate was acidified to pH 5 with 1N citric acid and then was extracted with ethyl acetate. The organic layer was washed with brine and dried over sodium sulfate. The solvent was evaporated and the residue eluted from silica gel with 1:1 ethyl acetate/hexane to give 3.0 gm of the desired product.

BOC-PHE[CH$_2$NZ]HIS(TRT)-STA-LEU-NHCH$_2$Ph

BOC-PHE[CH$_2$NZ]HIS(TRT) (0.93 g) and STA-LEU-NHCH$_2$Ph.HCl (0.5 g) were dissolved in DMF (30 ml) and cooled to 0°. Hydroxybenzotriazole (0.16 g) and triethylamine (0.17 g) were added and then dicyclohexylcarbodiimide (0.25 g) was added to the mixture. The solution was allowed to slowly warm to 25° and stir overnight. The mixture was filtered and was then extracted with ethyl acetate and water. The organic phase was washed with water, saturated sodium carbonate solution, and brine. The extract was dried over sodium sulfate, filtered, and evaporated. The residue was eluted from silica gel with 1:1 ethyl acetate/hexane to give 1.0 g of the correct material.

BOC-PHE[CH₂NZ]HIS-STA-LEU-NHCH₂Ph

BOC-PHE[CH₂NZ]HIS(TRT)-STA-LEU-NHCH₂Ph (0.9 g) was dissolved in 80% acetic acid/water and was heated on a steam bath for five minutes. The solution was allowed to slowly cool to 25° and the solvent evaporated. The residue was extracted with ethyl acetate/sodium carbonate and the organic layer was washed with brine. The extract was dried over sodium sulfate, filtered and evaporated. The residue was eluted on silica gel with 1:1 ethyl acetate/hexane to give 0.5 g of the product.

INTERMEDIATES FOR EXAMPLE 65

Z-LEU-N(CH₃)OCH₃

Z-LEU (10.1 g) was dissolved in dichloromethane (100 ml) and cooled to 0°. Carbonyl diimidazole (6.2 g) was added and the mixture stirred at 0° for three hours. A mixture of O,N dimethylhydroxylamine hydrochloride (4 g) and triethylamine (5.3 ml) was added in dichloromethane (20 ml) to the cold mixture. The mixture was allowed to warm to 25° and stir overnight. The mixture was poured into water and the organic phase washed with 1N citric acid, sodium bicarbonate, and brine. The extract was dried over sodium sulfate, filtered, and evaporated to give 10 g of product.

Z-LEU[CHO]

Z-LEU-N(CH₃)OCH₃ (2 g) was dissolved in THF (30 ml) and cooled to 0°. Lithium aluminum hydride (0.25 g) was added and the mixture stirred for 30 minutes. Acetone (1 ml) and 1N citric acid (20 ml) were added to the reaction. The mixture was extracted with ethyl acetate. The organic phase was washed with citric acid, sodium bicarbonate and brine. The extract was dried over sodium sulfate, filtered and evaporated to give the aldehyde, 1.8 g.

Z-LEU[CH₂NH]LEU-NHCH₂Ph

Z-LEU[CHO](7.3 g) and LEU-NHCH₂Ph (3.6 g) were stirred together in toluene (100 ml) along with molecular sieves (3 Å) (12 g). The mixture was stirred for 24 hours then filtered and cooled to 0°. Sodium borohydride (1.4 g) in ethanol (50 ml) was added and the mixture stirred for one hour. Acetic acid/water 1:1 was added to quench the reaction. The mixture was neutralized with sodium carbonate and then extracted with ethyl acetate/water. The organic layer was washed with brine and dried over sodium sulfate. The solvent was evaporated and the residue eluted from silica gel with 1:1 ethyl acetate/hexane to give 5 g of the product.

Z-LEU[CH₂NBOC]LEU-NHCH₂Ph

Z-LEU[CH₂NH]LEU-NHCH₂Ph (5 g) and tert-butyl dicarbonate (2.5 g) were stirred together in dichloromethane for 72 hours at 25°. The solvent was evaporated and the residue eluted from silica gel with 3:1 hexane/ether to give 5.6 g of product.

LEU[CH₂NBOC]LEU-NH-CH₂Ph

Z-LEU[CH₂NBOC]LEU-NHCH₂Ph (5.6 g) and palladium on carbon (20%) (0.2 g) were stirred together in methanol (100 ml). The flask was evacuated and then flushed with hydrogen from a balloon. The mixture was stirred for three hours at 25°. The flask was then evacuated and flushed with nitrogen. The mixture was filtered and the solvent evaporated to give the product 4.2 g.

Z-HIS(TRT)-LEU[CH₂NBOC]LEU-NHCH₂Ph

LEU[CH₂NBOC]LEU-NHCH₂Ph (2.5 g), Z-HIS(TRT) (3 g), and hydroxybenzotriazole (0.73 g) were stirred together in dimethylformamide (50 ml). The mixture was cooled to 0° and dicyclohexylcarbodiimide (1.1 g) was added. The mixture was allowed to slowly warm to 25° and was then stirred for 24 hours. The mixture was filtered and the filtrate dissolved in ethyl acetate. The solution was washed with water, sodium bicarbonate, and brine. The extract was dried over sodium sulfate, filtered, and evaporated. The residue was eluted from silica gel with 4:1 hexane/ethyl acetate to give 2.0 g of product.

HIS(TRT)-LEU[CH₂NBOC]LEU-NHCH₂Ph

Z-HIS-LEU[CH₂NBOC]LEU-NHCH₂Ph (2.0 g) and palladium on carbon (20%) (0.2 g) were stirred together in methanol (30 ml). The flask was evacuated and then flushed with hydrogen from a balloon. The mixture was stirred for four hours at 25°. The flask was evacuated and flushed with nitrogen. The mixture was filtered and the solvent evaporated to give 1.8 g of product.

IVA-PHE-HIS(TRT)-LEU[CH₂NBOC]LEU-NHCH₂Ph

HIS(TRT)-LEU[CH₂NBOC]LEU-NHCH₂Ph (1.9 g), IVA-PHE (0.6 g) and hydroxybenzotriazole (0.32 g) were stirred together in dimethylformamide (20 ml). The mixture was cooled to 0° and dicyclohexylcarbodiimide (0.5 g) was added. The mixture was allowed to slowly warm to 25°. The mixture was stirred for 24 hours, then filtered. The filtrate was dissolved in ethyl acetate and the resulting mixture was extracted with water, sodium bicarbonate, and brine. The solvent was evaporated and the residue eluted from silica gel with 1:1 ethyl acetate/hexane to give 2.0 g of product.

INTERMEDIATES FOR EXAMPLE 66

Z-HIS(TRT)-N(CH₃)OCH₃

Z-HIS(TRT) (19.3 g) was dissolved in dichloromethane (300 ml) and cooled to 0°. Carbonyldiimidazole (5.1 g) was added and the mixture was stirred for three hours. A suspension of O,N dimethylhydroxyamine hydrochloride (3.55 g) and triethylamine (5 ml) in dichloromethane (70 ml) was added to the mixture and the resulting suspension warmed to 25° and stirred overnight. The mixture was extracted with water, citric acid, sodium bicarbonate, and brine. The extract was dried over sodium sulfate, filtered, and evaporated. The residue was recrystallized from ethyl acetate, mp 153°–155°, 20 g.

Z-HIS(TRT)[CHO]

Z-HIS(TRT)-N(CH₃)OCH₃ (2.0 g) was dissolved in tetrahydrofuran and cooled to 0°. Lithium aluminum hydride (0.25 g) was added and the mixture stirred for 30 minutes. Acetone (1 ml) and citric acid (1N) (20 ml) were added and the mixture extracted with ethyl acetate. The organic phase was washed with citric acid, sodium bicarbonate, and brine. The extract was dried over sodium sulfate, filtered, and evaporated to give the aldehyde (1.6 g).

Z-HIS(TRT)[CH$_2$NH]STA-LEU-NHCH$_2$Ph

Z-HIS(TRT)[CHO] (0.62 g) and STA-LEU-NHCH$_2$Ph (0.46 g) were mixed in ethanol along with molecular sieves (3 Å) (3.0 g). The mixture was stirred for 24 hours at 25° then sodium cyanoborohydride (0.06 g) and citric acid (0.11 g) were added. The mixture was stirred for 24 hours at 25°, then filtered, and evaporated. The residue was dissolved in citric acid (1N) and then neutralized with sodium bicarbonate. The mixture was extracted with ethyl acetate and the organic layer washed with brine. The extract was dried over sodium sulfate, filtered, and evaporated. The residue was eluted from silica gel with 1:1 ethyl acetate/hexane to give 0.6 g of product.

Z-HIS(TRT)[CH$_2$NBOC]STA-LEU-NHCH$_2$Ph

Z-HIS(TRT)[CH$_2$NH]STA-LEU-NHCH$_2$Ph (0.5 g) and di-tert-butyl dicarbonate (0.2 g) were stirred together in dichloromethane for 24 hours at 25°. The solvent was evaporated and the residue extracted with ethyl acetate and water. The organic phase was washed with sodium bicarbonate and brine. The extract was dried over sodium sulfate, filtered, and evaporated. The residue was eluted from silica gel with 1:1 ethyl acetate/hexane to give 0.4 g of product.

HIS(TRT)[CH$_2$NBOC]STA-LEU-NHCH$_2$Ph

Z-HIS(TRT)[CH$_2$NBOC]STA-LEU-NHCH$_2$Ph (0.4 g) was dissolved in methanol (20 ml). Palladium on carbon (20%) (0.1 g) was added and then the flask evacuated and then flushed with hydrogen from a balloon. The mixture was stirred for three hours at 25° then the flask was evacuated and flushed with nitrogen. The mixture was filtered and the solvent evaporated to give 0.35 g of product.

IVA-PHE-HIS(TRT)[CH$_2$NBOC]STA-LEU-NHCH$_2$Ph

HIS(TRT)[CH$_2$NBOC]STA-LEU-NHCH$_2$Ph (0.35 g), IVA-PHE (0.17 g) and hydroxybenzotriazole (0.1 g) were stirred together in dimethylformamide and cooled to 0°. Dicyclohexylcarbodiimide (0.14 g) was added and the mixture allowed to slowly warm to 25°. The mixture was stirred for 24 hours and then filtered. The filtrate was extracted with ethyl acetate and water. The organic phase was washed with water, sodium bicarbonate, and brine. The extract was dried over sodium sulfate, filtered and evaporated. The residue was eluted from silica gel with 1:1 ethyl acetate/hexane to give 0.2 g of product.

INTERMEDIATES FOR EXAMPLE 68

BOC-CYCLOHEXYLALA[CH$_2$NH]HIS(TRT)-OCH$_3$

BOC-CYCLOHEXYLALA[CHO] (5.5 g) and HIS(TRT)-OCH$_3$ (8.87 g) were dissolved in methanol (200 ml). Molecular sieves (3 Å) (20 g) were added and the mixture stirred for 24 hours at 25°. Sodium cyanoborohydride (1.35 g) and citric acid (1.4 g) were added and the mixture stirred for 24 hours. The mixture was filtered and evaporated. The residue was dissolved in ethyl acetate and extracted with 1N citric acid. The organic layer was washed with saturated sodium bicarbonate, and brine, dried over sodium sulfate, filtered, and evaporated. The residue was eluted from silica gel with 1:1 ethyl acetate hexane to give 6.3 g of product.

BOC-CYCLOHEXYLALA[CH$_2$NH]HIS(TRT)

BOC-CYCLOHEXYLALA[CH$_2$NH]HIS(TRT)-OCH$_3$ (3.3 g) was dissolved in dioxane (0.5 ml) and cooled to 0°. Sodium hydroxide (0.2 g in 5 ml of water) was added and the mixture allowed to warm to 25°. The mixture was stirred for two hours and then was acidified to pH 5 with 1N citric acid. The mixture was extracted with ethyl acetate and the organic phase washed with water and brine. The solvent was dried over sodium sulfate, filtered, and evaporated to give 3.2 g of product sufficiently pure to be used in the next reaction.

BOC-CYCLOHEXYLALA[CH$_2$NH]HIS(TRT)-STA-LEU-NHCH$_2$Ph

BOC-CYCLOHEXYLALA[CH$_2$NH]HIS(TRT) (0.77 g) and STA-LEU-NHCH$_2$Ph.HCl (0.5 g) were dissolved in DMF (20 ml) and cooled to 0°. Triethylamine (0.16 ml) and hydroxybenzotriazole (0.16 g) were added to the mixture. Dicyclohexylcarbodiimide (0.25 g) was added and the mixture allowed to slowly warm to 25° and stir for 24 hours. The mixture was filtered and the filtrate dissolved in ethyl acetate and extracted with water. The organic phase was washed with sodium bicarbonate solution and brine. The solvent was dried over sodium sulfate, filtered, and evaporated. The residue was eluted from silica gel with 1:1 ethyl acetate/hexane to give 0.7 g of product.

INTERMEDIATES FOR EXAMPLE 69

BOC-PHE[CH$_2$NH]HIS(TRT)-STA-LEU-NHCH$_2$Ph

BOC-PHE[CH$_2$NZ]HIS(TRT)-STA-LEU-NHCH$_2$Ph (2.5 g) was dissolved in methanol (20 ml) and palladium on carbon (20%) (0.2 g) was added. The flask was evacuated and then flushed with hydrogen and stirred for 3 hours at 25°. The flask was flushed with nitrogen and the mixture filtered. The solvent was evaporated to give the product, 2.0 g.

BOC-PHE[CH$_2$NOH]HIS(TRT)-STA-LEU-NHCH$_2$Ph

BOC-PHE[CH$_2$NH]HIS(TRT)-STA-LEU-NHCH$_2$Ph (1.0 g) was dissolved in dichloromethane (10 ml) and cooled to 0°. Meta-chloroperbenzoic acid (0.27 g) was added and the mixture allowed to warm to 25° for four hours. The solvent was evaporated and the residue dissolved in ethyl acetate and washed with 10% sodium hydroxide. The organic layer was washed with brine, dried over sodium sulfate, filtered, and evaporated. The residue was eluted from silica gel with 1:1 ethyl acetate/hexane to give 0.5 g of the product.

INTERMEDIATES FOR EXAMPLE 70

Z-CYCLOHEXYLALA

PHE (100 g) was dissolved in water (1 l) with sodium hydroxide 25 g. Rhodium on carbon (10%) (15 g) was added and the mixture was shaken under a hydrogen atmosphere at 50 psi until the theoretical amount of hydrogen was taken up. The mixture was filtered and the solution cooled to 0°. Dioxane (300 ml) was added to the solution and benzyl chloroformate (110 g) and sodium hydroxide (25 g in 250 ml of water) were added dropwise simultaneously to the mixture. The mixture was stirred for one hour after the addition was complete. The solution was acidified with HCl to pH 1 and extracted with ether. The ether layer was washed with NaOH (25 g in 250 ml of water). The aqueous phase was acidified to pH 1 with HCl and extracted with ether. The ether layer was washed with brine, dried over sodium sulfate, filtered, and evaporated to give 170 g of product.

Z-CYCLOHEXYLALA-N(CH₃)-OCH₃

Z-CYCLOHEXYLALA (13 g) was dissolved in dichloromethane (200 ml) and cooled to 0°. Carbonyldiimidazole (7.0 g) was added and the mixture stirred for two hours. A solution of O,N-dimethylhydroxylamine hydrochloride (4.15 g) and triethylamine (6 ml) in dichloromethane (100 ml) was added. The mixture was allowed to warm slowly to 25° and stir overnight. The mixture was poured into water and shaken. The organic layer was washed with citric acid, sodium bicarbonate, and brine. The extract was dried over sodium sulfate, filtered and evaporated to give the product.

Z-CYCLOHEXYLALA[CHO]

Z-CYCLOHEXYLALA-N(CH₃)-OCH₃ (15 g) was dissolved in THF (200 ml) and cooled to 0°. Lithium aluminum hydride (1.8 g) was added and the mixture stirred for one-half hour. Water was added until there was no more active hydride and citric acid was added until the pH was 5. The mixture was extracted with ethyl acetate and washed with sodium bicarbonate and brine. The solvent was dried over sodium sulfate, filtered, and evaporated to give the aldehyde, 12 g.

Z-CYCLOHEXYLALA[CH₂NH]LEU-NHCH₂Ph

BOC-CYCLOHEXYLALA[CHO] (12 g) and LEU-NHCH₂Ph (9 g) were dissolved in THF (200 ml) and stirred with molecular sieves (3 Å) (30 g) for 24 hours. Sodium cyanoborohydride (2.6 g) and citric acid (3 g) were added and the mixture stirred for 24 hours. The mixture was filtered and evaporated. The residue was dissolved in ethyl acetate and extracted with 1N citric acid, saturated sodium bicarbonate, and brine. The extract was dried over sodium sulfate, filtered, and evaporated. The residue was eluted from silica gel with 1:1 ethyl acetate/hexane to give 7.1 g of product.

Analysis: Calcd.: C, 72.98; H, 8.18; N, 8.51. Found: C, 73.22; H, 8.81; N, 8.54.

Z-CYCLOHEXYLALA[CH₂NBOC]LEU-NHCH₂Ph

Z-CYCLOHEXYLALA[CH₂NH]LEU-NHCH₂Ph (4 g), 4-dimethylaminopyridine (0.5 g), and di-tertbutyldicarbonate (2.0 g) were added to dichloromethane (50 ml) and stirred for 48 hours at 25°. The solvent was evaporated and the residue extracted with ethyl acetate and water. The organic phase was washed with sodium bicarbonate and brine. The solvent was dried over sodium sulfate, filtered, and evaporated. The residue was eluted from silica gel with 4:1 hexane/ether to give 2 g of product.

CYCLOHEXYLALA[CH₂NBOC]LEU-NHCH₂Ph

Z-CYCLOHEXYLALA[CH₂NBOC]LEU-NHCH₂Ph (2.0 g) was dissolved in methanol (15 ml) and palladium on carbon (20%) (0.2 g) was added. The reaction flask was evacuated and then flushed with hydrogen from a balloon. The mixture was stirred for four hours at 25°. The reaction flask was evacuated and flushed with nitrogen and the mixture filtered. The solvent was evaporated to give 1.2 g of product.

Z-HIS(TRT)-CYCLOHEXYLALA[CH₂NBOC]-LEU-NHCH₂Ph

CYCLOHEXYLALA[CH₂NBOC]LEU-NHCH₂Ph (1.2 g) and Z-HIS(TRT) (1.4 g) were dissolved in dimethylformamide (15 ml) at 0°. Hydroxybenzotriazole (0.36 g) and then dicyclohexylcarbodiimide (0.54 g) were added. The mixture was allowed to warm to 25° slowly and stir overnight. The mixture was filtered and the filtrate extracted with ethyl acetate/water. The organic layer was washed with water, sodium bicarbonate, and brine. The extract was dried over sodium sulfate, filtered, and evaporated. The residue was eluted from silica gel with 1:1 ethyl acetate/hexane to give of the desired product.

HIS(TRT)-CYCLOHEXYLALA[CH₂NBOC]LEU-NHCH₂Ph

Z-HIS(TRT)-CYCLOHEXYLALA[CH₂NBOC]-LEU-NHCH₂Ph (0.9 g) was dissolved in methanol (15 ml) and palladium on carbon (0.1 g) added. The mixture was evacuated and then flushed with hydrogen from a balloon. The mixture was stirred for three hours and then was evacuated and flushed with nitrogen. The mixture was filtered and the solvent evaporated to give 0.78 g of the desired product.

IVA-PHE-HIS(TRT)-CYCLOHEXYLALA[CH₂NBOC]LEU-NHCH₂Ph

HIS(TRT)CYCLOHEXYLALA[CH₂NBOC]LEU-NHCH₂Ph (0.78 g) and IVA-PHE (0.23 g) were dissolved in dimethylformamide and cooled to 0°. Hydroxybenzotriazole (0.13 g) and dicyclohexylcarbodiimide (0.19 g) were added sequentially and the mixture allowed to slowly warm to 25° and stir for 24 hours. The mixture was filtered and the filtrate extracted with ethyl acetate and water. The organic layer was washed with water, sodium bicarbonate, and brine. The extract was dried over sodium sulfate, filtered, and evaporated. The residue was eluted from silica gel with 1:1 ethyl acetate/hexane to give 0.7 g of the product.

INTERMEDIATES FOR EXAMPLE 71

IVA-ILE-OCH₃

A suspension of 15 g (0.082 mole) of ILE-OCH₃·HCl [*J. Am. Chem. Soc.*, 81, 890, (1959)] in 200 ml of dichloromethane was cooled to 0°. To this, 28.76 ml (0.205 mole) of triethylamine was slowly added followed ten minutes later by 11.11 ml (0.0902 mole) of isovaleryl chloride while the reaction temperature was maintained at 0°. The mixture was kept at 0° for one hour and then allowed to warm to room temperature overnight.

The reaction mixture was washed with H₂O, 1N HCl, saturated NaHCO₃, saturated NaCl, dried, and the solvent removed to give 18.39 g of a yellow oil. Chromatography on silica gel, eluting with hexane-ethyl acetate 75/25; and combination of the appropriate fractions gave 17.69 g (94.8%) of the product.

Calcd.: C, 62.85; H, 10.10; N, 6.10. Found: C, 62.51; H, 9.90; N, 5.94.

$[\alpha]_D^{25} = -19.7°$ (C, 1.35, MeOH).

IVA-ILE

To a mixture of 17.66 g (0.077 mole) IVA-ILE-OCH₃ in 200 ml of methanol, was added 42.3 ml (0.085 mole) 2N sodium hydroxide. When TLC showed the reaction was done, the solvent was removed, and the residue dissolved in H₂O and washed with diethyl ether. The aqueous solution was brought to pH 2 with 1N hydrochloric acid causing the title compound to precipitate. The white solid was collected and dried to give 15.40 g (92.9%) of IVA-ILE.

Calcd.: C, 61.37; H, 9.83; N, 6.51. Found: C, 61.63; H, 9.94; N, 6.46.

$[\alpha]_D^{25} = -0.63°$ (C, 0.96, MeOH).

IVA-ILE-N(CH₃)OCH₃

To 50 ml of dichloromethane was added with stirring 5 g (0.023 mole) of IVA-ILE under a nitrogen atmosphere. The solution was cooled to 0° and 4.11 g (0.025 mole) of carbonyldiimidazole was slowly added. After one hour at 0°, 2.44 g (0.025 mol) of O,N-dimethylhydroxylamine hydrochloride and 3.04 ml (0.025 mol) of N-methylpiperidine were added while keeping the reaction mixture at 0°. The solution was kept at 0° for an hour and then allowed to warm to room temperature overnight.

The solvent was removed under reduced pressure and the residue dissolved in ethyl acetate. Undissolved N-methylpiperidine hydrochloride was filtered off and the ethyl acetate solution was washed with 1N HCl, saturated NaHCO₃, and saturated NaCl. The solution was dried and the solvent removed under reduced pressure to afford 5.9 g (99.3%) of the product as a pale yellow oil.

Calcd.: C, 60.44; H, 10.14; N, 10.44. Found: C, 60.11; H, 9.88; N, 10.87.

$[\alpha]_D^{25} = -19.9°$ (C, 1.0, MeOH).

IVA-ILE[CHO]

To 50 ml of dry, distilled tetrahydrofuran was added 2.97 g (0.0115 mole) of IVA-ILE-N(CH₃)-OCH₃ under a nitrogen atmosphere. The solution was cooled to 0° and 0.607 g (0.016 mole) of lithium aluminum hydride added in small portions to the rapidly stirred mixture, while maintaining the reaction temperature near 0°. After 30 minutes at 0° a solution of 4 g sodium bisulfate in 60 ml of H₂O was quickly added with gas evolution. Ethyl acetate was added to the mixture and the layers were separated. The aqueous layer was thoroughly washed with ethyl acetate and the combined organic phases washed with 1N HCl, saturated NaHCO₃, and saturated NaCl. The solution was dried and the solvent removed under reduced pressure to give 2.56 g (99%) of IVA-ILE[CHO] as a pale yellow oil.

IVA-ILE[CH₂NH]VAL-OCH₃

Under a nitrogen atmosphere, 2.27 g (0.0115 mole) of IVA-ILE[CHO] and 1.92 g (0.0115 mole) of VAL-OCH₃.HCl were dissolved in 50 ml absolute ethanol. To this solution 8 g of activated 3 Å molecular sieves were added followed by 1.61 ml (0.0115 mole) of triethylamine. The solution was stirred for one hour and a trace of bromocresol green and 1.08 g (0.0172 mole) of sodium cyanoborohydride were added. Using a previously prepared solution of ethanolic HCl, pH was adjusted to a light green color. After two days, the mixture was filtered and solid citric acid added to the filtrate until the foaming ceased. The solvent was removed under reduced pressure and the residue taken up in ethyl acetate. The organic solution was washed with H₂O, saturated NaHCO₃, saturated NaCl, and was dried. The solvent was removed under reduced pressure to give 3.4 g of an oil. The oil was chromatographed over silica eluting with chloroform/methanol, 98/2. The appropriate fractions were combined to afford 2.43 g (59.7%) of the product.

Calcd. for C₁₇H₃₄N₂O₃ (MW 353.86): C, 58.82; H, 9.78; N, 7.92. Found: C, 58.86; H, 9.32; N, 7.92.

IVA-ILE[CH₂NZ]VAL-OCH₃

To a solution of 2.25 g (0.0064 mole) of IVA-ILE[CH₂NH]VAL-OCH₃ in 20 ml of tetrahydrofuran was added 20 ml of saturated sodium bicarbonate. The solution was cooled in ice and 1.09 ml (0.0076 mole) of benzyl chloroformate was slowly added over ten minutes. The reaction was followed by TLC and when complete the mixture was diluted with ethyl acetate. The layers were separated and the aqueous layer washed with ethyl acetate. The organic layers were combined and washed with 1N HCl, saturated NaHCO₃, and saturated NaCl. The solution was dried and the solvent removed under reduced pressure to yield 2.97 g (96.5%) of the product as an oil.

Calcd. for C₂₅H₄₀N₂O₅.0.15CHCl₃.0.2C₄H₈O₂: C, 64.38; H, 8.69; N, 5.79. Found: C, 64.58; H, 8.64; N, 5.42.

IVA-ILE[CH₂NZ]VAL

To 70 ml of methanol was added 2.92 g (0.0065 mole) of IVA-ILE[CH₂NZ]VAL-OCH₃ and 7.16 ml (0.014 mole) of 2N NaOH. TLC was used to monitor the reaction's progress. An additional 18 ml of 2N NaOH was added before the reaction was shown to be complete. The solvent was removed under reduced pressure and the residue dissolved in H₂O and washed with diethyl ether. The aqueous layer was brought to pH 2 with 2N HCl and the aqueous layer was thoroughly washed with ethyl acetate. The organic layer was dried and the solvent removed under reduced pressure to afford 2.24 g (79.4%) of the product as a white foam.

Analysis: Calcd.: C, 66.33; H, 8.81; N, 6.45. Found: C, 66.07; H, 8.68; N, 6.31.

IVA-ILE[CH₂NZ]VAL-STA-LEU-NHCH₂Ph

A solution of 0.5 g (0.0012 mole) of IVA-ILE[CH₂NZ]VAL 0.311 g (0.0012 mole) of hydroxybenztriazole, and 0.497 g (0.0012 mole) of STA-LEU-NHCH₂Ph.HCl in 20 ml of dimethylformamide was cooled to 0° in ice and 0.167 ml (0.0012 mole) of triethylamine was added. After ten minutes a solution of 0.248 g (0.0012 mole) of dicyclohexylcarbodiimide in dimethylformamide was slowly added. The reaction was kept at 0° for one hour and then allowed to warm to room temperature overnight. The solvent was removed under reduced pressure and the residue dissolved in ethyl acetate. The ethyl acetate solution was filtered and the filtrate washed with 1N HCl, saturated NaHCO₃, and saturated NaCl. The solvent was dried over MgSO₄ and was then removed under reduced pressure to give 0.95 g of a foam. The foam was chromatographed on silica gel and eluted with CHCl₃/EtOAc, 9/1. The appropriate fractions were combined to give 0.71 g (74.74%) of IVA-ILE[CH₂NZ]VAL-STA-LEU-NHCH₂Ph as a solid, mp 96°-102°.

Analysis: Calcd.: C, 68.06; H, 9.01; N, 8.81. Found: C, 68.64; H, 9.26; N, 8.52.

INTERMEDIATE FOR EXAMPLE 73

IVA-ILE[CH₂NH]ILE-OCH₃

To a solution of 1.86 g (0.0093 mole) IVA-ILE[CHO] and 1.70 g (0.0093 mole) ILE-OCH₃.HCl in 50 ml of absolute ethanol was added 10 g of dry 3 Å molecular sieves under a nitrogen atmosphere. To the solution was added 1.31 ml (0.0093 moles) of triethylamine, and the solution stirred for an hour before a trace of bromcresol green and 0.88 g (0.014 mole) of sodium cyanoborohydride were added. The pH was adjusted to pale green using a previously prepared ethanolic HCl solution. After two days the mixture was filtered and the solvent removed under reduced pressure. The residue was taken up in EtOAc and washed with H₂O, saturated NaHCO₃, and saturated NaCl. After drying over MgSO₄ the solvent was removed under reduced pressure to give 2.48 g of an oil. The oil was placed on silica gel and eluted with chloroform/methanol 99/1. The appropriate fractions are combined to afford 1.44 g (47.0%) of product as a foam.

Analysis: Calcd.: C, 65.81; H, 11.05; N, 8.52. Found: C, 65.98; H, 11.10; N, 8.56.

IVA-ILE[CH₂NH]ILE

To a solution of 1.37 g (4.17 mmole) of IVA-ILE[CH₂NH]ILE-OCH₃ in 30 ml of methanol was added 4.59 ml (4.17 mmole) of 1N sodium hydroxide. The reaction was monitored by TLC. Later 8 ml of 2N sodium hydroxide was added and after 36 hours the reaction appeared finished. The solvent was removed under reduced pressure and the oily residue dissolved in H₂O. The aqueous solution was washed with diethyl ether and acidified to pH 2.5 using 2N HCl. The solution was lyophilized to dryness and redissolved in ethyl acetate. The inorganic salts were filtered off and the solvent removed under reduced pressure to afford 0.91 g (69.5%) of product.

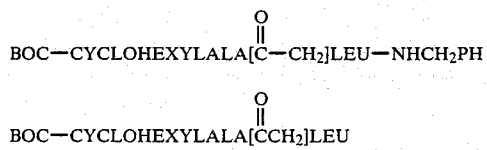

INTERMEDIATE FOR EXAMPLE 78

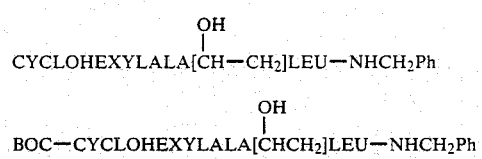

(1.3 g), benzylamine (0.36 g), and hydroxybenzotriazole (0.45 g) were stirred together in dimethylformamide (20 ml). The mixture was cooled to 0° and dicyclohexylcarbodiimide (0.7 g) added. The mixture was allowed to slowly warm to 25° and was stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 20% ethyl acetate/hexane to give 1.6 g of product.

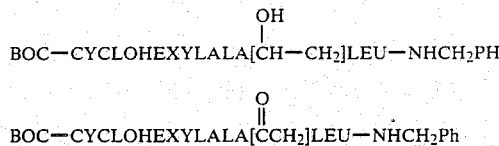

(1.6 g) was dissolved in ethanol (25 ml) and cooled to 0°. Sodium borohydride (0.13 g) was added and the mixture allowed to warm to 25°. The mixture was stirred for two hours and then acetic acid and water 1:1 was added. The solvent was evaporated and the residue extracted with ethyl acetate and sodium carbonate. The organic phase was washed with brine, dried over sodium sulfate, filtered, and evaporated. The residue was eluted from silica gel with 15% ethyl acetate/hexane to give 0.8 g of product.

OH
|
CYCLOHEXYLALA[CH—CH₂]LEU—NHCH₂Ph

OH
|
BOC—CYCLOHEXYLALA[CHCH₂]LEU—NHCH₂Ph (0.8 g) was dissolved in dichloromethane and trifluoroacetic acid (4 ml) added. The mixture was stirred for one hour at 25° and then the solvent was evaporated. The residue was extracted with ethyl acetate and sodium carbonate. The organic phase was washed with brine, dried over sodium sulfate, filtered, and evaporated to give 0.6 g of product.

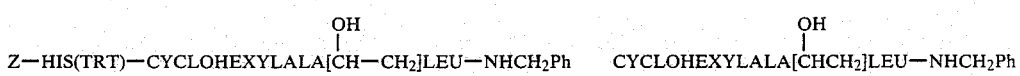

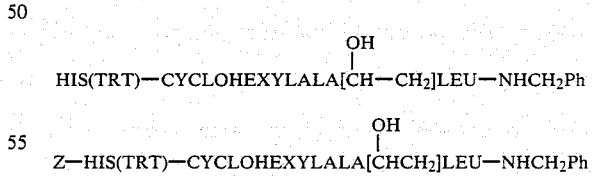

(0.6 g), Z-HIS(TRT) (0.9 g), and hydroxybenzotriazole (0.23 g) were stirred together in dimethylformamide (15 ml). The mixture was cooled to 0° and dicyclohexylcarbodiimide (0.35 g) added. The mixture was allowed to slowly warm to 25° and was stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 1:4 hexane/ethyl acetate to give 1.1 g of product.

OH
|
HIS(TRT)—CYCLOHEXYLALA[CH—CH₂]LEU—NHCH₂Ph

OH
|
Z—HIS(TRT)—CYCLOHEXYLALA[CHCH₂]LEU—NHCH₂Ph (1.3 g) was dissolved in methanol (20 ml) and palladium on carbon (20%) (0.2 g) added. The flask was flushed with hydrogen and the mixture stirred for three hours. The flask was flushed with nitrogen and the mixture filtered. The solvent was evaporated to give 1.0 g of product.

HIS(TRT)—CYCLOHEXYLALA[CHCH2]LEU—NHCH2Ph

(0.5 g), IVA-PHE (0.17 g), and hydroxybenzotriazole (0.1 g) were stirred together in dimethylformamide (15 ml). The mixture was cooled to 0° and dicyclohexylcarbodiimide (0.14 g) added. The mixture was allowed to warm slowly to 25° and was then stirred for 24 hours. The mixture was filtered and the filtrate extracted with ethyl acetate and water. The organic phase was washed with water, sodium bicarbonate, and brine. The extract was dried over sodium sulfate, filtered, and evaporated. The residue was eluted from silica gel with 1:1 ethyl acetate/hexane and then 80:20 ethyl acetate hexane to give 0.4 g of product.

INTERMEDIATES FOR EXAMPLE 74

BOC-PHE[CH2NZ]HIS(TRT)-PHSTA-LEU-NHCH2Ph

To a solution of 300 mg (0.39 mmole) of BOC-PHE[CH2NZ]HIS(TRT), 175 mg (0.39 mmole) of PHSTA-LEU-NHCH2Ph.HCl, and 53 mg (0.39 mmole) of hydroxybenzotriazole in 20 ml of DMF was added 0.06 ml (0.39 mmole) of Et3N and the solution cooled to 0°. A solution of 81 mg (0.39 mmole) of dicyclohexylcarbodiimide in 5 ml of DMF was then added and the solution kept at 0° for one hour, then at room temperature overnight. The solvent was removed under reduced pressure and the residue dissolved in ethyl acetate. The organic solution was washed with 1N HCl, H2O, saturated NaHCO3, saturated NaCl, dried, and the solvent removed under reduced pressure to give 0.57 g of a solid. This solid was chromatographed on silica gel and eluted with chloroform/methanol 99/1. The appropriate fractions were combined to give 300 mg (66.4%) of the product.

BOC-PHE[CH2NZ]HIS-PHSTA-LEU-NHCH2Ph

To a solution of 20 ml of 80% acetic acid/water was added 0.3 g (0.239 mmole) of BOC-PHE[CH2NZ]HIS(TRT)-PHSTA-LEU-NHCH2Ph. The solution was warmed to 90° on a steam bath for 5 minutes and then allowed to slowly cool to room temperature. The solvent was removed under reduced pressure and the residue dissolved in ethyl acetate. The ethyl acetate solution was washed with saturated NaHCO3, saturated NaCl, dried, and the solvent removed under reduced pressure to afford 0.32 g of crude product. After chromatography over silica gel eluting with chloroform/methanol, 93/7 the appropriate fractions were combined to give 200 mg (84.38%) of the product.

INTERMEDIATES FOR EXAMPLE 75

α-BROMO-N-[(1-HYDROXYMETHYL)-3-METHYLBUTYL]BENZENEACETAMIDE (α-center is RS; center with NH substituent is S)

Thionyl chloride, 88 g (0.75 mole), was added to a solution of 107 g (0.5 mole) of α-bromophenylacetic acid in 1 l of toluene. The mixture was warmed on a steam bath for 30 minutes, allowed to stand at room temperature for one day and the solvent then evaporated in vacuo. Toluene, 500 ml, was added and the solvent evaporated in vacuo. The evaporation process was repeated a second time from 500 ml of toluene. The acid chloride, 100 g, was used without further purification. A solution of the acid chloride, 23.4 g (0.1 mole), in 50 ml of acetone was added dropwise with stirring to a solution of L-leucinol, 11.72 g (0.1 mole), and sodium acetate, 16.4 g (0.2 mole), in 500 ml of 50% aqueous acetone at 0°-5°. The mixture was stirred and allowed to reach room temperature over two hours, the solvent was evaporated in vacuo and the residue suspended in 200 ml of dichloromethane and extracted successively with 100 ml of a 10% aqueous solution of citric acid, 100 ml of a 10% aqueous solution of sodium bicarbonate and 100 ml of a saturated aqueous solution of sodium chloride. The dichloromethane layer was separated, dried over sodium sulfate, evaporated in vacuo and the residue chromatographed using 500 g of silica gel and eluting with 1 l of dichloromethane-methanol (98:2) and then 1 l of dichloromethane-methanol (97:3) to give α-bromo-N-[(1-hydroxymethyl)-3-methylbutyl]benzeneacetamide (α-center is RS; center with NH-substituent is S), 25 g; $[\alpha]_D^{25} = -34.2°$ (C, 0.62, methanol).

Calcd. for $C_{14}H_{20}NBrO_2$: C, 53.51; H, 6.42; N, 4.46. Found: C, 53.90; H, 6.41; N, 4.46.

5-(2-METHYLPROPYL)-2-PHENYL-3-MORPHOLINONE (center phenyl is R, S, other center is S)

α-Bromo-N-[(1-hydroxymethyl)-3-methylbutyl]benzeneacetamide (α-center is RS, other center with NH-substituent is S), 9.1 g (0.029 mole), was dissolved in 200 ml of tetrahydrofuran, the solution is cooled to 0°-5° and 1.65 g (0.0413 mole) of 60% sodium hydride in mineral oil dispersion slowly added. The mixture was allowed to reach room temperature and stirred overnight, the solvent was evaporated in vacuo and the residue dissolved in 200 ml of dichloromethane and extracted twice with water. The dichloromethane layer was separated, dried over sodium sulfate, evaporated in vacuo and the residue chromatographed using 200 g of silica gel and eluting with 1 l of dichloromethane-methanol (99.5:0.5) to give 5-(2-methylpropyl)-2-phenyl-3-morpholinone (center phenyl is R, S, other center is S), 5.48 g; $[\alpha]_D^{25} = -22.9°$ (C, 0.62, methanol).

Calcd. for $C_{14}H_{19}NO_2$: C, 72.07; H, 8.21; N, 6.00. Found: C, 72.01; H, 8.11; N, 5.94.

Z-LEU[CH2O]PHGLY 5-(2-Methylpropyl)-2-phenyl-3-morpholinone (center phenyl is R, S, other center is S), 0.95 g (0.0041 mole), was suspended in a solution of 50 ml of concentrated hydrochloric acid and 50 ml of water, heated for one hour on a steam bath, cooled to room temperature, and extracted with 100 ml of dichloromethane. The aqueous layer was separated and the pH adjusted with sodium hydroxide to pH 10.5 and 0.84 g (0.0049 mole) of benzyl chloroformate was added dropwise while the pH was maintained at 10.5 with sodium hydroxide. After addition was complete the mixture was extracted with 100 ml of diethylether, the aqueous layer was separated and the pH adjusted to 3 by the addition of a 10% aqueous solution of hydrochloric acid. The mixture was extracted with 200 ml of dichloromethane. The dichloromethane layer was separated, dried over sodium sulfate, evaporated in vacuo and the residue purified by chromatography using silica gel and eluting with 1 l of dichloromethane-methanol (95:5) to give α-[[4-methyl-2[[(phenylmethoxy)carbonyl]amino]pentyl]oxy]benzeneacetic acid (α-carbon is R, S, other stereo site is S), 1.1 g; $[\alpha]_D^{25} = -78.9°$ (C, 0.56, methanol).

Calcd. for $C_{22}H_{27}NO_5$: C, 68.55; H, 7.06; N, 3.63. Found: C, 68.66; H, 6.85; N, 3.57.

INTERMEDIATES FOR EXAMPLE 80

Z-CYCLOHEXYLALA

PHE (100 g) was dissolved in water (1 l) with sodium hydroxide (25 g). Rhodium on carbon (10%) (15 g) was added and the mixture was flushed with hydrogen. The system was pressurized to 50 psi for two hours. The mixture was filtered and the filtrate was cooled to 0°. Dioxane (300 ml) was added and a simultaneous addition of 25 g of sodium hydroxide in 250 ml of water and benzyl chloroformate (110 g) was started. The mixture was stirred for one hour after the addition was complete. The mixture was extracted with ether and the aqueous phase was acidified with concentrated HCl to pH 1. The mixture was extracted with ether and the organic layer was washed with water and brine. The extract was dried over sodium sulfate, filtered, and evaporated to give 170 g of crude product.

This can be called Z-CYCLOHEXYLALA.

Z-CYCLOHEXYLALA[COCHN₂]

Z-CYCLOHEXYLALA (30 g) was dissolved in ethyl acetate (250 ml) and cooled to −20°. N-methyl piperidine (12 ml) was added followed by a dropwise addition of isobutyl chloroformate (13 ml). The mixture was stirred for ten minutes and then filtered under nitrogen into a cold flask. Diazomethane (8 g) in ether was added and the mixture was allowed to stand at 0° overnight. Nitrogen was bubbled through the solution to remove any excess diazomethane. The solvent was washed with water, sodium bicarbonate, and brine. The organic phase was dried over sodium sulfate, filtered, and evaporated to give 31.7 g of product.

This can be called Z-CYCLOHEXYLALA[COCHN₂].

Z-CYCLOHEXYLALA[COCH₂Br]

Z-CYCLOHEXYLALA[COCHN₂] (31.7 g) was dissolved in ether (200 ml) and cooled to −20°. Hydrogen bromide gas was bubbled into the solution until the nitrogen evolution stopped. The solution had a pH of 1. The mixture was extracted with sodium bicarbonate and brine. The organic layer was dried over sodium sulfate, filtered, and evaporated. The residue was recrystallized from hexane to give 21.5 g of product, mp 63°–64°.

This can be called Z-CYCLOHEXYLALA[COCH₂Br].

Calcd. for $C_{18}H_{24}NO_3Br$: C, 56.55; H, 6.33; N, 3.66. Found: C, 56.97; H, 6.25; N, 3.99.

Z-CYCLOHEXYLALA[COCH₂CH(CO₂-t-Bu)₂]

Sodium hydride (1.41 g) (50% in mineral oil) was washed with hexane and then suspended in DMF (100 ml). Di-tert-butyl malonate (6.34 g) was added and the mixture stirred for one hour at 25°. The mixture was cooled to 0° and Z-CYCLOHEXYLALA[COCH₂Br] (11.2 g) was added. The mixture was allowed to warm to 25° and was stirred for 24 hours. 1N Citric acid (20 ml) was added and the mixture extracted with ether/water. The organic phase was washed with water, sodium bicarbonate, and brine. The solvent was dried over sodium sulfate, filtered, and evaporated. The residue was eluted on silica gel with 3:1 hexane/ether to give 14 g of product.

This can be called Z-CYCLOHEXYLALA[COCH₂CH(CO₂-t-Bu)₂].

Z-CYCLOHEXYLALA[COCH₂]GLY

Z-CYCLOHEXYLALA[COCH₂CH(CO₂-t-Bu)₂] (6.0 g) was dissolved in trifluoroacetic acid (20 ml) and stirred at 25° for three hours. The solvent was evaporated and the residue was dissolved in toluene. The mixture was heated to reflux for three hours. The solution was allowed to cool to 25° and the solvent evaporated. The residue was eluted from silica gel with 3:1 hexane/ethyl acetate to give 3.5 g of product.

This can be called Z-CYCLOHEXYLALA[COCH₂]GLY.

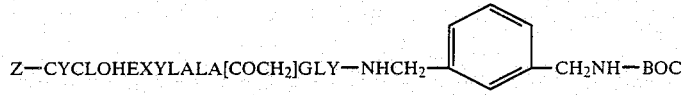

Z-CYCLOHEXYLALA[COCH₂]GLY (3.5 g), BOC-xylylenediamine (2.29 g) and hydroxybenzotriazole (1.31 g) were dissolved in DMF (30 ml) and cooled to 0°. Dicyclohexylcarbodiimide (2.0 g) was added and the mixture was allowed to slowly warm to 25° and stir for 24 hours. The mixture was filtered and the filtrate was extracted with ethyl acetate and water. The organic phase was washed with water, sodium bicarbonate, and brine. The solvent was dried over sodium sulfate, filtered, and evaporated. The residue was eluted from silica gel with 3:1 hexane/ethyl acetate to give 3.9 g of product.

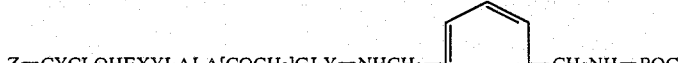

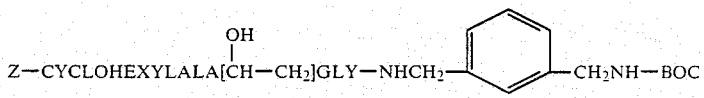

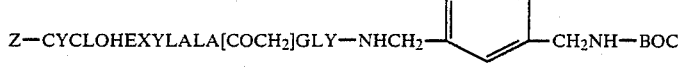

(3.9 g) was dissolved in ethanol (30 ml) and cooled to 0°. Sodium borohydride (0.26 g) was added and the mixture was stirred at 0° for 0.5 hour and at 25° for two hours. Citric acid (1N) was added to destroy any excess hydride reagent. The mixture was extracted with ethyl acetate and water. The organic layer was washed with water, sodium bicarbonate, and brine. The solvent was dried over sodium sulfate, filtered, and evaporated to give 3.9 g of product.

This can be called

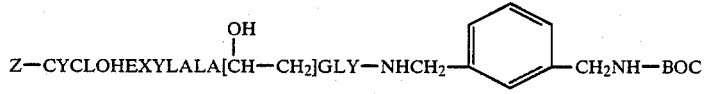

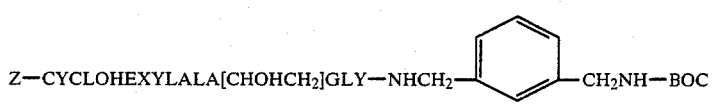

(3.9 g) was dissolved in methanol (30 ml) and palladium on carbon (20%) (0.5 g) was added. The system was evacuated and then flushed with hydrogen from a balloon. The mixture was stirred for four hours at 25°. The system was flushed with nitrogen and the mixture was filtered. The solvent was evaporated to give 3 g of product.

This can be called

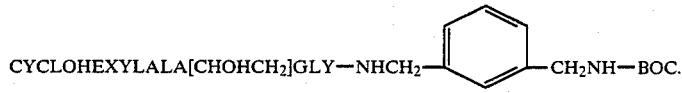

(3 g), Z-HIS(TRT) (3.6 g), and hydroxybenzotriazole (0.91 g) were dissolved in DMF (30 ml) and cooled to 0°. Dicyclohexylcarbodiimide (1.4 g) was added and the mixture was allowed to warm slowly to 25° and stir for 24 hours. The mixture was filtered and the filtrate was extracted with ethyl acetate and water. The organic phase was washed with water, sodium bicarbonate, and brine. The solvent was dried over sodium sulfate, filtered, and evaporated. The residue was eluted from silica gel with 1:1 ethyl acetate/hexane to give 4.9 g of product.

This can be called

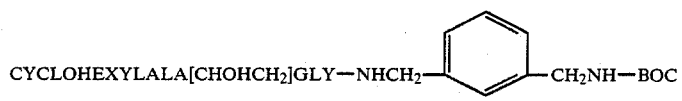

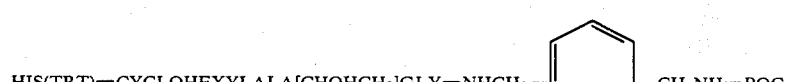

Z—HIS(TRT)—CYCLOHEXYLALA[CHOHCH₂]GLY—NHCH₂—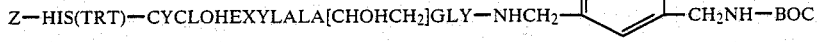—CH₂NH—BOC (4.9 g) was dissolved in methanol (40 ml) and palladium on carbon (20%) (0.4 g) was added. The system was flushed with hydrogen from a balloon and the mixture was stirred for four hours at 25°. The system was then flushed with nitrogen and the mixture was filtered. The solvent was evaporated to give 4 g of product. This can be called HIS(TRT)—CYCLOHEXYLALA[CHOHCH₂]GLY—NHCH₂—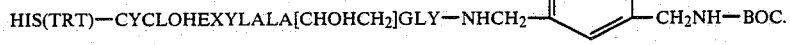—CH₂NH—BOC.

IVA—PHE—HIS(TRT)—CYCLOHEXYLALA[CHOHCH₂]GLY—NHCH₂——CH₂NH—BOC

HIS(TRT)—CYCLOHEXYLALA[CHOHCH₂]GLY—NHCH₂—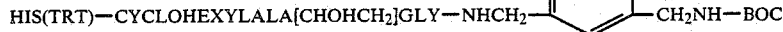—CH₂NH—BOC (1 g), IVA-PHE (0.3 g), and hydroxybenzotriazole (0.16 g) were dissolved in DMF (15 ml) and cooled to 0°. Dicyclohexylcarbodiimide (0.25 g) was added and the mixture was allowed to slowly warm to 25° and stir for 24 hours. The mixture was filtered and the filtrate was extracted with ethyl acetate and water. The organic phase was washed with ether, sodium bicarbonate, and brine. The solvent was dried over sodium sulfate, filtered, and evaporated. The residue was eluted from silica gel with ethyl acetate to give 1 g of product. This can be called IVA—PHE—HIS(TRT)—CYCLOHEXYLALA[CHOHCH₂]GLY—NHCH₂——CH₂NH—BOC.

INTERMEDIATES FOR EXAMPLE 81

Z—CYCLOHEXYLALA[COCH₂]LEU.

Z—CYCLOHEXYLALA[COCH₂]LEU—NHCH₂—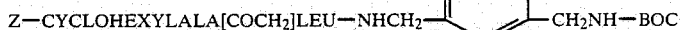—CH₂NH—BOC

Z-CYCLOHEXYLALA[COCH₂]LEU[(CO₂-t-Bu)₂]

Sodium hydride (1.3 g) (50% in mineral oil) was washed with hexane and then suspended in DMSO (50 ml). Z-CYCLOHEXYLALA[COCH₂CH(CO₂-t-Bu)₂] (14 g) in DMSO (50 ml) was added. The mixture was stirred at 25° until hydrogen evolution stopped (one hour). The mixture was cooled to 5° and isobutyl iodide (3.11 ml) was added. The mixture was allowed to warm to 25° and stir for 24 hours. 1N Citric acid (20 ml) was added and the mixture was extracted with ether/water. The organic layer was washed with water, sodium bicarbonate, and brine. The solvent was dried over sodium sulfate, filtered, and evaporated. The residue was eluted from silica gel with 4:1 hexane/ether to get 9.0 g of product which was dissolved in dichloromethane and evaporated.

Calcd. for $C_{33}H_{51}NO_7 \cdot 0.5CH_2Cl_2$: C, 65.33; H, 8.51; N, 2.27. Found: C, 65.67; H, 8.46; N, 2.64.

This can be called Z-CYCLOHEXYLALA[COCH₂]LEU[(CO₂-t-Bu)₂].

Z-CYCLOHEXYLALA[COCH₂]LEU

Z-CYCLOHEXYLALA[COCH₂]LEU[(CO₂-t-Bu)₂] (9.0 g) was dissolved in trifluoroacetic acid (15 ml) and stirred at 25° for three hours. The solvent was evaporated and the residue was dissolved in toluene (70 ml). The mixture was heated to reflux for three hours. The mixture was allowed to cool to 25° and the solvent was then evaporated. The residue was eluted from silica gel with 3:1 hexane/ethyl acetate to give 4.5 g of product.

This can be called Z-CYCLOHEXYLALA[COCH₂]LEU (4.5 g), BOC-xylylenediamine (2.55 g), and hydroxybenzotriazole (1.46 g) were dissolved in DMF (50 ml) and cooled to 0°. Dicyclohexylcarbodiimide (2.22 g) was added and the mixture was allowed to slowly warm to 25° and stir for 24 hours. The mixture was filtered and the filtrate was extracted with ethyl acetate and water. The organic layer was washed with water, sodium bicarbonate, and brine. The solvent was dried over sodium sulfate, filtered, and evaporated. The residue was eluted from silica gel with 4:1 hexane/ethyl acetate to give 6.0 g of product.

This can be called

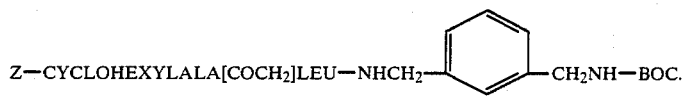

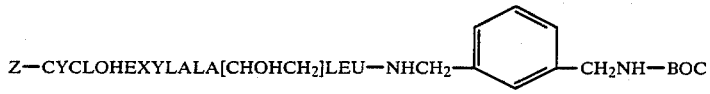

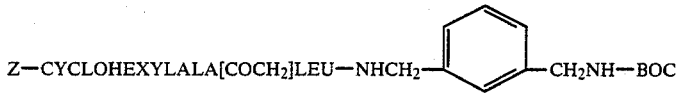

(6 g) was dissolved in ethanol (40 ml) and cooled to 0°. Sodium borohydride (0.36 g) was added and the mixture was stirred at 0° for one hour and at 25° for two hours. Citric acid (1N) was added to destroy any excess hydride and the mixture was extracted with ethyl acetate and water. The organic phase was washed with water, sodium bicarbonate, and brine. The solvent was dried over sodium sulfate, filtered, and evaporated. The residue was eluted from silica gel with dichloromethane and then ethyl acetate to give 6 g of product.

This can be called

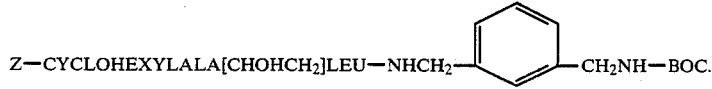

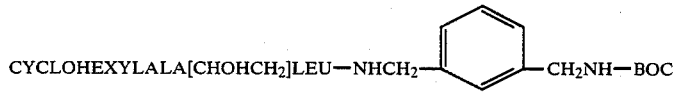

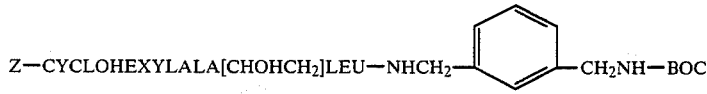

(6 g) was dissolved in methanol (50 ml) and palladium on carbon (20%) (0.5 g) was added. The system was evacuated and then flushed with hydrogen from a balloon. The mixture was stirred for six hours at 25°. The system was flushed with nitrogen and the mixture was filtered. The solvent was evaporated to give 4.8 g of product.

This can be called

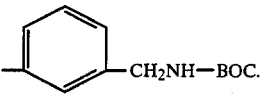

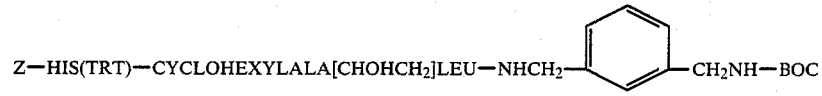

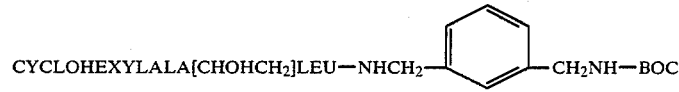

(4.8 g ), Z-HIS(TRT) (5.03 g), and hydroxybenzotriazole (1.3 g) were dissolved in DMF (30 ml) and cooled to 0°. Dicyclohexylcarbodiimide (2.0 g) was added and the mixture was allowed to slowly warm to 25° and stir for 24 hours. The mixture was filtered and the filtrate was extracted with ethyl acetate and water. The organic phase was washed with water, sodium bicarbonate, and brine. The organic phase was dried over sodium sulfate, filtered, and evaporated. The residue was eluted from silica gel with ethyl acetate to give 5.5 g of product.

This can be called

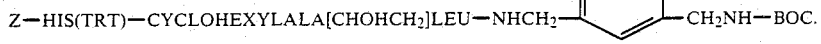

Z—HIS(TRT)—CYCLOHEXYLALA[CHOHCH₂]LEU—NHCH₂—⟨C₆H₄⟩—CH₂NH—BOC.

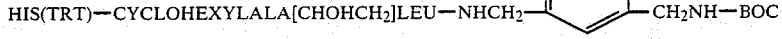

HIS(TRT)—CYCLOHEXYLALA[CHOHCH₂]LEU—NHCH₂—⟨C₆H₄⟩—CH₂NH—BOC

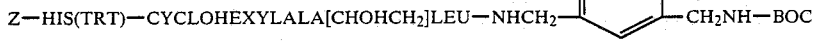

Z—HIS(TRT)—CYCLOHEXYLALA[CHOHCH₂]LEU—NHCH₂—⟨C₆H₄⟩—CH₂NH—BOC (5.5 g) was dissolved in methanol (30 ml) and palladium on carbon (20%) (0.4 g) was added. The system was flushed with hydrogen from a balloon and stirred for four hours. The system was then flushed with nitrogen and the mixture was filtered. The solvent was evaporated to give 5 g of product.

This can be called

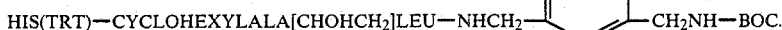

HIS(TRT)—CYCLOHEXYLALA[CHOHCH₂]LEU—NHCH₂—⟨C₆H₄⟩—CH₂NH—BOC.

IVA—PHE—HIS(TRT)—CYCLOHEXYLALA[CHOHCH₂]LEU—NHCH₂—⟨C₆H₄⟩—CH₂NH—BOC

HIS(TRT)—CYCLOHEXYLALA[CHOHCH₂]LEU—NHCH₂—⟨C₆H₄⟩—CH₂NH—BOC (1 g), IVA-PHE (0.28 g), and hydroxybenzotriazole (0.15 g) were dissolved in DMF (15 ml) and cooled to 0°. Dicyclohexylcarbodiimide (0.23 g) was added and the mixture was allowed to slowly warm to 25° and stir for 24 hours. The mixture was filtered and the filtrate was extracted with ethyl acetate and water. The organic layer was washed with water, sodium bicarbonate, and brine. The solvent was dried over sodium sulfate, filtered, and evaporated. The residue was eluted on silica gel with 1:1 ethyl acetate/hexane then ethyl acetate to give 0.8 g of product.

This can be called stir for 24 hours. The solvent was evaporated and the residue was extracted with ethyl acetate/citric acid. The aqueous phase was made basic with 10% sodium hydroxide. The mixture was extracted with ethyl acetate and the organic phase was washed with brine, dried over sodium sulfate, filtered, and evaporated to give 2.9 g of product.

This can be called

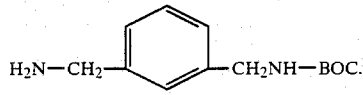

H₂N—CH₂—⟨C₆H₄⟩—CH₂NH—BOC.

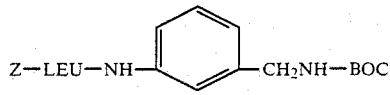

Z—LEU—NH—⟨C₆H₄⟩—CH₂NH—BOC

IVA—PHE—HIS(TRT)—CYCLOHEXYLALA[CHOHCH₂]LEU—NHCH₂—⟨C₆H₄⟩—CH₂NH—BOC.

INTERMEDIATES FOR EXAMPLE 82

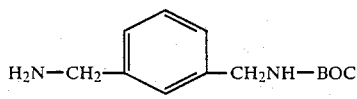

H₂N—CH₂—⟨C₆H₄⟩—CH₂NH—BOC

Meta-xylylenediamine (3.0 g) was dissolved in dichloromethane (20 ml) and cooled to 0°, BOC-ON (5.4 g) was added and the mixture allowed to warm to 25° and Z-LEU (3.0 g), hydroxybenzotriazole (1.53 g), and BOC-xylylenediamine (2.7 g) were dissolved in DMF (25 ml) and cooled to 0°. Dicyclohexylcarbodiimide (2.33 g) was added and the mixture was allowed to slowly warm to 25° and stir for 24 hours. The mixture was filtered and the filtrate was extracted with ethyl acetate and water. The organic layer was washed with water, sodium bicarbonate, and brine. The solvent was dried over sodium sulfate, filtered and evaporated. The residue was recrystallized from ethyl acetate to give 7.0 g of product, mp 114°–115°.

Calcd. for $C_{27}H_{37}N_3O_5$: C, 67.05; H, 7.71; N, 8.69. Found: C, 66.59; H, 7.76; N, 8.61.

Carbamic acid, [1-[[[[3-[[[(1,1-dimethylethoxy) car-bonyl]amino]methyl]phenyl]methyl]amino]carbonyl]-3-methylbutyl]-, phenylmethyl ester, (S).

This can also be called

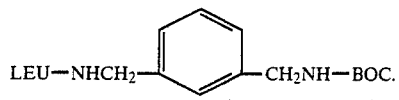

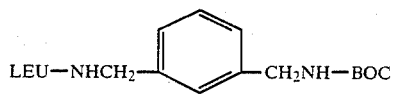

(3.1 g), and hydroxybenzotriazole (1.2 g) were dissolved in DMF (30 ml) and cooled to 0°. Dicyclohexylcarbodiimide (1.8 g) was added and the mixture was allowed to slowly warm to 25° and stir for 24 hours. The mixture was filtered and the filtrate was extracted with ethyl acetate and water. The organic phase was washed with water, sodium bicarbonate, and brine. The solvent was dried over sodium sulfate, filtered, and evaporated to give 7.2 g of product.

This can be called

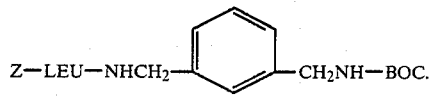

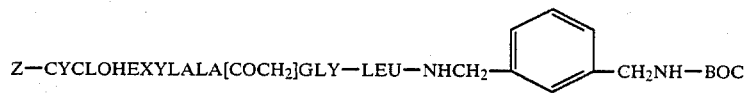

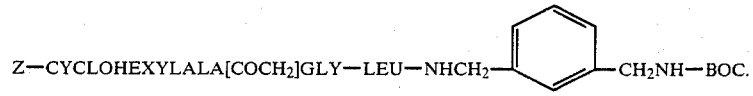

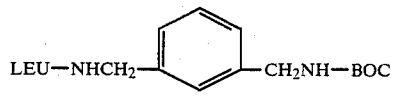

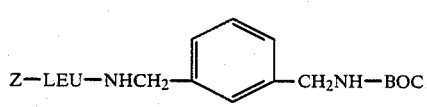

(4.3 g) was dissolved in methanol and palladium on carbon (20%) (0.4 g) was added. The system was flushed with hydrogen from a balloon and stirred for three hours at 25°. The system was then flushed with nitrogen and the mixture was filtered. The solvent was evaporated to give 4 g of product.

This can be called

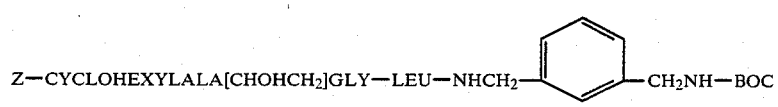

Z—CYCLOHEXYLALA[COCH₂]GLY (3.2 g),

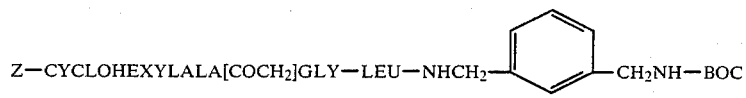

(7.2 g) was dissolved in ethanol (30 ml) and cooled to 0°. Sodium borohydride (0.4 g) was added. The mixture was stirred for one hour at 0° and two hours at 25°. Citric acid (1N) was added to destroy any excess hydride and then the mixture was extracted with chloroform and water. The organic phase was washed with water, sodium bicarbonate, and brine. The organic phase was dried over sodium sulfate, filtered, and evaporated. The residue was recrystallized from ethyl acetate to give 4.4 g of product.

This can be called

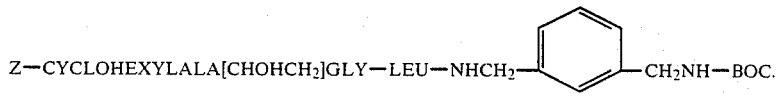

-continued

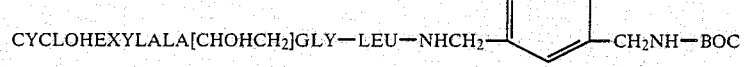

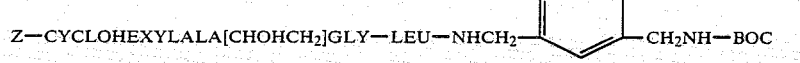

(4.4 g) was partially dissolved methanol (100 ml). Palladium on carbon (20%) (0.4 g) was added and the system was flushed with hydrogen from a balloon. The mixture was heated to 35° and stirred for two hours. The mixture was allowed to cool to 25° and then flushed with nitrogen. The mixture was filtered and the solvent was evaporated to give 3.8 g of product. This can be called

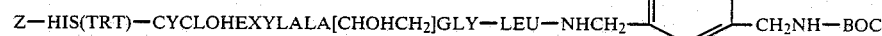

(3.3 g), Z-HIS(TRT) (3.1 g), and hydroxybenzotriazole (0.79 g) were dissolved in DMF (30 ml) and cooled to 0°. Dicyclohexylcarbodiimide (1.21 g) was added and the mixture was allowed to slowly warm to 25° and stir for 24 hours. The mixture was filtered and the filtrate was extracted with ethyl acetate and water. The organic phase was washed with water, sodium bicarbonate, and brine. The solvent was dried over sodium sulfate, filtered, and evaporated. The residue was eluted from silica gel with ethyl acetate to give 3 g of product. This can be called

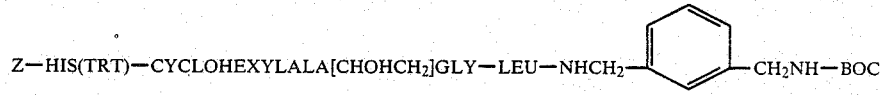

(1.4 g) was dissolved in methanol (20 ml) and palladium on carbon (20%) (0.2 g) added. The system was flushed with hydrogen from a balloon and the mixture was stirred for two hours at 25°. The system was flushed with nitrogen and the mixture was filtered and evaporated to give (0.94 g) of product. This can be called

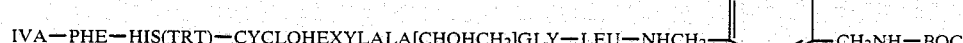

HIS(TRT)—CYCLOHEXYLALA[CHOHCH₂]GLY—LEU—NHCH₂CH₂NH—BOC (0.94 g), IVA-PHE (0.35 g), and hydroxybenzotriazole (0.19 g) were dissolved in DMF (20 ml) and cooled to 0°. Dicyclohexylcarbodiimide (0.29 g) was added and the mixture was allowed to warm slowly to 25° and stir for 24 hours. The mixture was filtered and the filtrate was extracted with ethyl acetate and water. The organic phase was washed with water, sodium bicarbonate and brine. The solvent was dried over sodium sulfate, filtered, and evaporated. The residue was eluted from silica gel with ethyl acetate to give 1.0 g of product.

This can be called

PHE[CHOHCH=CHCO]NHCH₂CH(CH₃)CH₂CH₃

A solution of 1.07 g of BOC-PHE[CHOHCH=CHCO] NHCH₂CH(CH₃)CH₂CH₃ in 30 ml of dichloromethane was treated with 10 ml of trifluoroacetic acid and stirred at room temperature for 1.5 hours. The solvent was then removed under reduced pressure. The residue was taken up in EtOAc and washed twice with saturated NaHCO₃, then with saturated NaCl. Drying over MgSO₄ and removal of the solvent under reduced pressure left 780 mg of the product as an oily solid. This can be called PHE[-

IVA—PHE—HIS(TRT)—CYCLOHEXYLALA[CHOHCH₂]GLY—LEU—NHCH₂CH₂NH—BOC.

INTERMEDIATE FOR EXAMPLE 83

BOC-PHE[CH₂NH]HIS(TRT)-CYSTA-LEU-NHCH₂Ph

A solution of 0.7 g (1.1 mmole) of BOC-PHE[CH₂NH]HIS(TRT), 0.5 g (1.1 mmole) of CYSTA-LEU-NHCH₂Ph.HCl, and 0.15 g (1.1 mmole) of hydroxybenzotriazole in 20 ml of DMF was cooled in ice and treated with 0.15 ml (1.1 mmole) of triethylamine followed by 0.23 g (1.1 mmole) of N,N'-dicyclohexylcarbodiimide. The solution was allowed to warm to 25° overnight. The mixture was filtered, diluted with EtOAc and washed several times with water, saturated NaHCO₃ solution, then brine. After drying over Na₂SO₄ and removal of the solvent under reduced pressure, the residue was purified by chromatography on silica gel, eluting with CH₂Cl₂/EtOAc (1:1). There was obtained 0.6 g of BOC-PHE[CH₂NH]HIS(TRT)-CYSTA-LEU-NHCH₂Ph.

INTERMEDIATES FOR EXAMPLE 84

BOC-PHE[CHOHCH=CHCO]NHCH₂CH(CH₃)CH₂CH₃

A solution of 1.0 g (3.3 mmole) of BOC-PHE[CHOHCH=CHCO₂H] and 443 mg (3.3 mmole) of hydroxybenzotriazole in 15 ml of DMF was cooled in ice and treated with 683 mg (3.3 mmole) of N,N'-dicyclohexylcarbodiimide followed by 290 mg (3.3 mmole) of S-(−)-2-methylbutylamine. The mixture was kept at 0° for 0.5 hour, then allowed to warm to room temperature overnight. The solvent was removed under reduced pressure and the residue taken up in EtOAc. The precipitated N,N'-dicyclohexylurea was filtered off and the filtrate washed with 1N HCl, H₂O, saturated NaHCO₃, and saturated NaCl. Drying over MgSO₄ and removal of the solvent under reduced pressure left 1.22 g of crude product. Recrystallization from MeOH/H₂O gave 1.07 g of pure product, mp 120°-125°. This can be called BOC-PHE[CHOHCH=CHCO]NHCH₂CH(CH₃)CH₂CH₃.

Calcd. for C₂₂H₃₄N₂O₃ (MW 374.50): C, 70.55; H, 9.15; N, 7.48. Found: C, 70.20; H, 9.29; N, 8.17.

CHOHCH=CHCO]NHCH₂(CH₃)CH₂CH₃.

BOC-HIS-PHE[CHOHCH=CHCO]NHCH₂CH(CH₃)CH₂CH₃

A solution of 726 mg (2.84 mmole) of BOC-HIS and 385 (2.84 mmole) of hydroxylbenzotriazole in 15 ml DMF was cooled in ice and 593 mg (2.84 mmole) of N,N'-dicyclohexylcarbodiimide added followed by a solution of PH[CHOHCH=CHCO]NHCH₂CH(CH₃)CH₂CH₃ in 5 ml of DMF. An additional 0.4 ml (2.84 mmole) of triethylamine was added and the mixture kept at 0° for 0.5 hour, then at room temperature overnight. The solvent was removed under reduced pressure and the residue taken up in EtOAc. The precipitated N,N'-dicyclohexylurea was filtered off and the filtrate washed with H₂O, saturated NaHCO₃, then saturated NaCl. Drying over MgSO₄ and removal of the solvent under reduced pressure gave 1.3 g of crude product. Chromatography on silica gel, eluting with CHCl₃/MeOH (95/5) gave 980 mg of pure product as a foam. This can be called BOC-HIS-PHE[CHOHCH=CHCO] NHCH₂CH(CH₃)CH₂CH₃.

Calcd. for C₂₈H₄₁N₅O₄.0.3CHCl₃ (MW 547.46): C, 62.08; H, 7.60; N, 12.79. Found: C, 62.01; H, 7.57; ;L N, 13.35.

HIS-PHE[CHOHCH=CHCO]NHCH₂CH(CH₃)CH₂CH₃

A solution of 878 mg (1.72 mmole) of BOC-HIS-PHE[CHOHCH=CHCO]NHCH₂CH(CH₃)CH₂CH₃ in 20 ml of dichloromethane was treated with 10 ml of trifluoroacetic acid and stirred at room temperature for two hours. The solvent was removed under reduced pressure and the residue was taken up in EtOAc and washed with 0.1N NaOH, then saturated NaCl. The basic solution was extracted with CHCl₃ and the CHCl₃ dried. The two organic extracts were combined and the solvent removed under reduced pressure giving 410 mg of a cream foam. This can be called HIS-PHE[CHOHCH=CHCO]NHCH₂CH(CH₃)CH₂CH₃.

PREPARATION OF IVA-PHE

IVA-PHE-OCH₃

PHE-OCH₃.HCl (15.2 g) was suspended in dichloromethane (200 ml) and cooled to 0°. Triethylamine (23 ml) was added and then isovaleryl chloride (10.3 ml) was added dropwise. After the addition the mixture was allowed to warm to 25° and stir for 24 hours. The mixture was poured into water and shaken. The organic phase was washed with 10% HCl and sodium bicarbonate. The solvent was dried over sodium sulfate, filtered, and evaporated. The residue was recrystallized from hexane and diisopropyl ether to give 17 g of product, mp 50°-51°.

Analysis: Calcd.: C, 68.41; H, 8.04; N, 5.32. Found: C, 68.51; H, 7.84; N, 5.32.

IVA-PHE

IVA-PHE-OCH₃ (16.5 g) was dissolved in dioxane (100 ml) and cooled to 5°. Sodium hydroxide (2.5 g) in 50 ml of water was added and the mixture allowed to warm to 25°. The mixture was stirred for two hours and then the dioxane was evaporated. The mixture was acidified to pH 1 with 10% HCl. The product was collected by filtration and then dissolved in methanol. The methanol was evaporated and ethyl acetate was added to precipitate the product. The product was collected by filtration to give 13 g, mp 146°-149°.

Analysis: Calcd.: C, 67.44; H, 7.68; N, 5.62. Found: C, 64.26; H, 7.34; N, 5.31.

PREPARATION OF STA-LEU-NHCH₂Ph 1.80 g LEU-NHCH₂Ph.HCl [Japan No. 83/59952], 2.27 g BOC-STA (U.S. Pat. No. 4,397,786) and 1.04 g 1-hydroxybenzotriazole-hydrate were dissolved in 125 ml dichloromethane and cooled to 0°. A cold solution of 1.59 g dicyclohexylcarbodiimide in 20 ml dichloromethane was added, followed by the addition of 50 ml cold dimethylformamide. The mixture was stirred at 0° for two hours, followed by 12° overnight. The mixture was then filtered, stripped to a paste, and resuspended in ethyl acetate. The suspension was filtered, the filtrate washed with 1N citric acid, saturated sodium chloride solution, saturated sodium bicarbonate solution, and saturated sodium chloride solution, and dried over anhydrous magnesium sulfate. The suspension was filtered and stripped to a white foam 3.77 g, which was crystallized from ethyl ether and hexane giving a white solid, 3.41 g (92% yield), mp 89°-92°. Spectral and elemental analysis confirms the anticipated structure, BOC-STA-LEU-NHCH₂Ph. $[\alpha]_D^{23} = -34.2°$ (C, 1.06, MeOH).

2.77 g BOC-STA-LEU-NHCH₂Ph was dissolved in 100 ml dichloromethane, which was then saturated with anhydrous hydrogen chloride gas. After stirring at 25° for one hour, the solvent was removed in vacuo, and the residue resuspended in dichloromethane, giving a crystalline solid. The suspension was diluted with ethyl ether, filtered, and the solid dried in vacuo, 2.24 g, 93% yield. Spectral and elemental analyses confirm the structure as STA-LEU-NHCH₂Ph.HCl. $[\alpha]_D^{23} = -19.1°$ (C, 1.06, MeOH).

PREPARATION OF PHSTA-LEU-NHCH₂Ph

Using a method similar to that used for the preparation of STA-LEU-NHCH₂Ph above, but substituting BOC-PHSTA, the title compound was prepared. The structure was confirmed by spectral and elemental analysis.

PREPARATION OF STA-ALA-STA-NHCH₂Ph 12.0 g of BOC-STA (U.S. Pat. No. 4,397,786) and 6.25 g 1-hydroxybenzotriazole monohydrate were dissolved in 300 ml dichloromethane and cooled to −5°. 4.76 ml benzylamine was added, followed by a cold solution of 9.54 g dicylohexylcarbodiimide in 50 ml dichloromethane. The mixture was stirred and allowed to warm to 25° overnight. The mixture was filtered stripped to an oil and taken up into ethyl acetate. The solution was washed with 1N citric acid, saturated sodium bicarbonate solution, saturated sodium chloride solution, dried over anhydrous magnesium sulfate and filtered. The filtrate was stripped to a solid, dissolved in ethyl ether and a minor amount of solid filtered off. The filtrate was crystallized by the addition of hexane, the solid filtered and dried in vacuo giving 15.49 g, (97.5%) of a while solid, mp 100°-103° C. Spectral and elemental analyses confirm the expected structure, BOC-STA-NHCH₂Ph. $[\alpha]_D^{23} = -37.6°$ (C, 1.04, MeOH).

14.86 g BOC-STA-NHCH₂Ph was dissolved in 500 ml dichloromethane and anhydrous hydrogen chloride gas was bubbled into the mixture. After stirring at 25° for 1.5 hours, the mixture was stored overnight at 4°. The solution was stripped to a foam, taken up into dichloromethane, and again stripped to a foam. The foam was partitioned between ethyl acetate and saturated sodium bicarbonate solution and the organic phase was then washed with saturated sodium chloride solution. The solution was dried over anhydrous magnesium sulfate, filtered, and stripped to a yellow oil, 10.48 g. The oil was chromatographed on 600 g silica gel, eluting with a gradient of 5 to 20% methanol in chloroform and giving a white solid, 5.43 g (50% yield). IR and NMR spectra were consistent with the anticipated structure, STA-NHCH₂Ph.

4.51 g STA-NHCH₂Ph and 2.41 g 1-hydroxybenzotriazole hydrate were added to 400 ml dichloromethane. After cooling to −5°, 3.23 g of BOC-ALA was added, followed by a cold solution of 3.68 g dicyclohexylcarbodiimide in 25 ml dichloromethane. The mixture was stirred for two hours at 0°, followed by 48 hours at 5°. After warming to 25°, the mixture was filtered, stripped to a solid, dissolved in ethyl acetate and washed with 1N citric acid, saturated sodium chloride solution, saturated sodium bicarbonate solution, and saturated sodium chloride solution. The organic phase was dried over anhydrous magnesium sulfate, filtered, and reduced in volume in vacuo, giving a solid precipitate. The solid was filtered and washed with 75% hexane/25% ethyl acetate giving 6.82 g (92% yield), mp 156°-158°. Spectral and elemental analyses confirm the anticipated structure, BOC-ALA-STA-NHCH₂Ph. $[\alpha]_D^{23} = -44.3°$ (C, 1.04, MeOH).

6.75 g BOC-ALA-STA-NHCH₂Ph was dissolved in 200 ml of 50/50 trifluoroacetic acid and dichloromethane. After stirring for two hours, the mixture was stripped to an oil, dissolved in dichloromethane, and the procedure repeated twice. This yielded an oil, 12.97 g. The oil was taken up into ethyl acetate and water, and the ethyl acetate phase removed by evaporation in vacuo. The remaining aqueous phase was adjusted to pH 12.5 by addition of 50% sodium hydroxide solution and filtered to remove traces of insolubles. The filtrate was extracted with ethyl acetate, and the organic phase was washed with saturated sodium chloride solution, dried over anhydrous magnesium sulfate, filtered, and stripped to a crystalline solid, 4.23 g (81% yield), mp 148°–150°. Spectral and elemental analyses confirm the anticipated structure, ALA-STA-NHCH₂Ph. $[\alpha]_D^{23} = -46.7°$ (C, 1.04, MeOH).

2.23 g BOC-STA and 1.15 g 1-hydroxybenzotriazole hydrate were dissolved in 50 ml dichloromethane, and cooled to −5°. A cold solution of 2.72 g ALA-STA-NHCH₂Ph in 50 ml dichloromethane was added to the mixture, followed by addition of a cold solution of 1.76 g dicyclohexylcarbodiimide in about 20 ml dichloromethane. After stirring at 25° overnight, the suspension was filtered, stripped to an oil, and taken up into ethyl acetate. The solution was again filtered and washed with 1N citric acid, saturated sodium chloride solution, saturated sodium bicarbonate solution, and saturated sodium chloride solution. The organic phase was dried over anhydrous magnesium sulfate, filtered, and stripped to a foam. The foam was dissolved in ethyl ether, insolubles filtered off, and the solution then reduced in volume in vacuo. Addition of acetone/hexane gave a solid. Filtration and drying in vacuo gave a white solid, 4.54 g (94% yield), mp 164°–166°. Spectral analysis confirm the structure to be BOC-STA-ALA-STA-NHCH₂Ph. $[\alpha]_D^{23} = -53.5°$ (C, 1.16, MeOH). The material is sufficiently pure for use in the following step.

4.33 g BOC-STA-ALA-STA-NHCH₂Ph was dissolved in a 50/50 mixture of trifluoro acetic acid and dichloromethane. After stirring for 2.5 hours, the dichloromethane was removed in vacuo and the residue suspended in water. The pH was adjusted to 12.5 with 50% NaOH solution, and the mixture extracted into ethyl acetate. The organic phase was washed with saturated sodium chloride solution, dried over anhydrous magnesium sulfate, filtered and stripped to a crystalline solid, 2.77 g (77% yield), mp 135°–142°. After recrystallization from ethyl acetate and methanol, a white solid was obtained, 2.05 g (57% yield), mp 147°–150°. Spectral and elemental analyses confirm the structure as STA-ALA-STA-NHCH₂Ph. $[\alpha]_D^{23} = -57.2°$ (C, 1.18, MeOH).

We claim:

1. A peptide selected from the group consisting of

BOC—PHE[CH=CH]GLY—STA—LEU—NHCH₂Ph,
IVA—PHE[CH=CH]GLY—STA—LEU—NHCH₂Ph,
BOC—PHE[CH=CH]GLY—PHSTA—LEU—NHCH₂Ph,
BOC—PHE[CH=CH]GLY—CYSTA—LEU—NHCH₂Ph,
BOC—TRP[CH=CH]GLY—STA—LEU—NHCH₂Ph,

BOC—PHE[CH=CH]GLY—CYSTA—LEU—

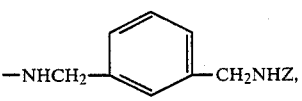

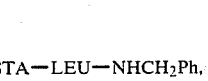

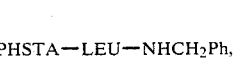

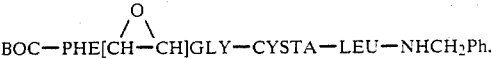

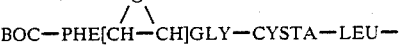

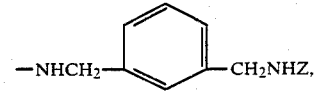

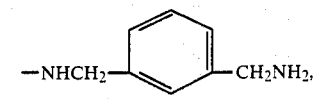

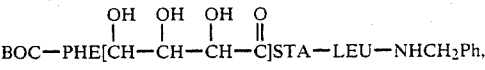

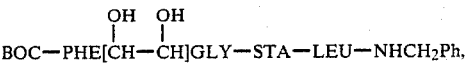

BOC—PHE[CH—CH—CH—C]STA—LEU—NHCH₂Ph, (with OH OH OH O above)

BOC—PHE[CH—CH]GLY—STA—LEU—NHCH₂Ph, (with OH OH above)

BOC—CYCLOHEXALA[CH—CH]GLY—STA—LEU—NHCH₂Ph, (with OH OH above)

BOC—TRP[CH—CH]GLY—STA—LEU—NHCH₂Ph, (with OH OH above)

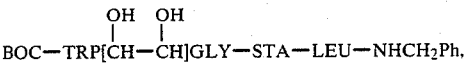

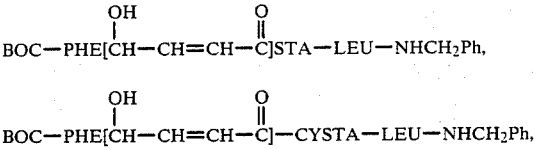

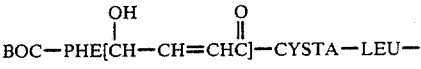

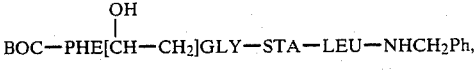

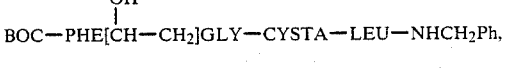

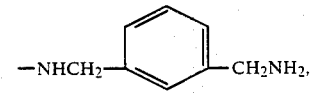

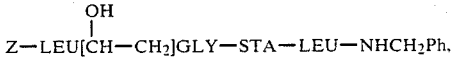

Z—LEU[CH(OH)—CH₂]LEU—STA—LEU—NHCH₂Ph,

IVA—PHE—HIS—CYCLOHEXALA[CH(OH)—CH₂]GLY—NHCH₂Ph,

IVA—PHE—HIS—CYCLOHEXALA[CH(OH)—CH₂]GLY—LEU—NHCH₂Ph,

BOC—PHE[CH(OH)—CH₂]HIS—STA—LEU—NHCH₂Ph,

BOC—PHE[CH(OH)—CH₂]HIS—STA—LEU—NHCH₂Ph, (isomer)

IVA—LEU[C(O)—CH₂]PHE—STA—LEU—NHCH₂Ph,

Z—LEU[CH(OH)—CH₂]PHE—STA—LEU—NHCH₂Ph,

Z—LEU[C(O)—CH₂]PHE—STA—LEU—NHCH₂Ph,

BOC—PHE[CH₂CH₂]GLY—STA—LEU—NHCH₂Ph,

BOC—PHE[CH₂CH₂]GLY—CYSTA—LEU—NHCH₂-C₆H₄-CH₂NH₂,

IVA—PHE[CH₂S]PHE—STA—LEU—NHCH₂Ph,
BOC—PHE[CH₂SO]PHE—STA—LEU—NHCH₂Ph,

HO₂C(CH₂)₃C(O)—PHE[CH₂S]PHE—STA—LEU—NHCH₂Ph,

IVA—PHE[CH₂S]GLY—STA—LEU—NHCH₂Ph,

BOC—PHE[C(O)—CH₂]GLY—STA—LEU—NHCH₂Ph,

IVA—PHE[C(O)—CH₂]GLY—STA—LEU—NHCH₂Ph,

Z—PHE[C(O)—CH₂]PHE—STA—LEU—NHCH₂Ph,

BOC—CYCLOHEXYLALA[C(O)—CH₂]LEU—STA—LEU—NHCH₂Ph,

IVA—VAL[CH₂NH]VAL—STA—OEt,
IVA—VAL[CH₂NH]VAL—STA—NHCH₂Ph,
IVA—VAL[CH₂NH]VAL—STA—LEU—NHCH₂Ph,
BOC—PHE—VAL—STA—LEU[CH₂NZ]CH₂Ph,
IVA—PHE—HIS—STA—LEU[CH₂NZ]CH₂Ph,
IVA—PHE—HIS—STA—LEU[CH₂NH]CH₂Ph,
BOC—PHE[CH₂NH]PHE—STA—LEU—NHCH₂Ph,

BOC—D-PHE(Me⁵)[CH₂NH]HIS—STA—LEU—NH-(4-piperidinyl)-N-CH₂Ph.

BOC—PHE[CH₂NH]HIS(BOM)—STA—LEU—NHCH₂Ph,
BOC—PHE[CH₂NH]HIS—STA—LEU—NHCH₂Ph,
IVA—PHE—HIS—LEU[CH₂NH]LEU—NHCH₂Ph,
IVA—PHE—HIS[CH₂NH]STA—LEU—NHCH₂Ph,
BOC—PHE[CH₂NOH]PHE—STA—LEU—NHCH₂Ph,
BOC—CYCLOHEXYLALA[CH₂NH]HIS—STA—LEU—NHCH₂Ph,
BOC—PHE[CH₂NOH]HIS—STA—LEU—NHCH₂Ph,
IVA—PHE—HIS—CYCLOHEXYLALA[CH₂NH]LEU—NHCH₂Ph,
IVA—ILE[CH₂NH]VAL—STA—LEU—NHCH₂Ph,
IVA—ILE[CH₂NH]VAL—STA—LEU—NHCH₂Ph (isomer),
IVA—ILE[CH₂NH]ILE—STA—LEU—NHCH₂Ph,
BOC—PHE[CH₂NH]HIS—PHSTA—LEU—NHCH₂Ph, IVA—PHE—HIS—LEU[CH(OH)—CH₂]LEU—NHCH₂Ph,

Z—NAPHTHYLALA—HIS—CYCLOHEXYLALA[CHOHCH₂]GLY—NH—CH₂CH(CH₃)CH₂CH₃,

IVA—PHE—HIS—CYCLOHEXYLALA[CH(OH)—CH₂]LEU—NHCH₂Ph,

BOC—CYCLOHEXYLALA[CH(OH)—CH₂]LEU—STA—LEU—NHCH₂Ph,

IVA—PHE—HIS—CYCLOHEXYLALA[CHOHCH₂]GLY—NHCH₂-C₆H₄-CH₂NH₂,

IVA—PHE—HIS—CYCLOHEXYLALA[CHOHCH₂]LEU—NHCH₂-C₆H₄-CH₂NH₂,

IVA—PHE—HIS—CYCLOHEXYLALA[CHOHCH₂]GLY—LEU—NHCH₂-C₆H₄-CH₂NH₂,

BOC—PHE[CH₂NH]HIS—CYSTA—LEU—NHCH₂Ph,

BOC—PHE—HIS—PHE[CH(OH)CH=CHC(O)]NHCH₂CH(CH₃)CH₂CH₃, and

BOC—PHE—HIS—PHE[CHOHCH₂]GLY—NHCH₂CH(CH₃)CH₂CH₃.

2. A pharmaceutical composition comprising a renin-inhibitory effective amount of a compound as claimed in claim 1 together with a pharmaceutically acceptable carrier.

3. A method of treating renin-associated hypertension which comprises administering to a mammal a pharmaceutical composition as claimed in claim 1.

4. A method of treating hyperaldosteronism which comprises administering to a mammal a pharmaceutical composition as claimed in claim 1.

5. A peptide selected from the group consisting of

BOC—PHE[CH=CH]GLY—STA—ALA—STA—NHCH2Ph,
BOC—PHE[CH=CH]PHE—STA—ALA—STA—NHCH2Ph,
IVA—PHE[CH2S]PHE—STA—ALA—STA—NHCH2Ph,
IVA—PHE[CH2SO2]PHE—STA—ALA—STA—NHCH2Ph,
IVA—PHE[CH2SO]PHE—STA—ALA—STA—NHCH2Ph,
BOC—PHE[CH2SO2]PHE—STA—ALA—STA—NHCH2Ph,
BOC—PHE[CH2SO]PHE—STA—ALA—STA—NHCH2Ph,

PhC—PHE[C—CH2]GLY—STA—ALA—STA—NHCH2Ph,

BOC—PHE[C—CH2]GLY—STA—ALA—STA—NHCH2Ph,

IVA—VAL[CH2NH]VAL—STA—ALA—STA—NHCH2Ph,
BOC—PHE[CH2NH]PHE—STA—ALA—STA—NHCH2Ph,
BOC—PHE[CH2NH]HIS—STA—ALA—STA—NHCH2Ph, and
BOC—LEU[CH2O]PHGLY—STA—ALA—STA—NHCH2Ph.

6. A pharmaceutical composition comprising a renin-inhibitory effective amount of a compound as claimed in claim 5 together with a pharmceutically acceptable carrier.

7. A method of treating renin-associated hypertension which comprises administering to a mammal a pharmaceutical composition as claimed in claim 5.

8. A method of treating hyperaldosteronism which comprises administering to a mammal a pharmaceutical composition as claimed in claim 5.

* * * * *